United States Patent

Perkins et al.

[11] Patent Number: 6,106,457
[45] Date of Patent: Aug. 22, 2000

[54] COMPACT IMAGING INSTRUMENT SYSTEM

[75] Inventors: David G. Perkins, Syracuse; Jon R. Salvati, Skaneateles Falls; William M. Wrisley, North Syracuse; Ronald A. Hauptli, Warners; Stephen C. Wilson, E. Syracuse, all of N.Y.; Russ J. Kalil, Amherst, N.H.; Richard A. Monroe, Syracuse, N.Y.

[73] Assignee: Welch Allyn, Inc., Skaneateles Falls, N.Y.

[21] Appl. No.: 09/052,570

[22] Filed: Mar. 31, 1998

Related U.S. Application Data

[60] Provisional application No. 60/043,374, Apr. 4, 1997.

[51] Int. Cl.⁷ .............................. A61B 1/04; G03B 11/00
[52] U.S. Cl. .................... 600/175; 600/109; 600/160; 600/172; 600/200; 396/312; 396/532; 396/544
[58] Field of Search ................ 600/104, 109, 600/112, 127, 136, 172, 178, 175, 179, 200; 348/65, 72, 74, 76; 396/17, 299, 312, 532, 544

[56] References Cited

U.S. PATENT DOCUMENTS

| | | | |
|---|---|---|---|
| 4,323,304 | 4/1982 | Ishii | 600/112 |
| 4,380,998 | 4/1983 | Kieffer, III et al. | |
| 4,742,819 | 5/1988 | George | 600/109 |
| 4,859,032 | 8/1989 | Feinbloom | 359/801 |
| 4,860,094 | 8/1989 | Hibino | 600/109 |
| 4,864,341 | 9/1989 | Maekawa et al. | 396/532 |
| 4,866,516 | 9/1989 | Hibino | 600/109 |
| 4,869,237 | 9/1989 | Eino | 600/109 |
| 4,895,138 | 1/1990 | Yabe | 600/172 |
| 4,905,668 | 3/1990 | Ohsawa | 600/167 |
| 4,924,856 | 5/1990 | Noguchi | 600/109 |
| 4,947,245 | 8/1990 | Ogawa | 600/175 |
| 5,051,824 | 9/1991 | Nishigaki | |
| 5,079,629 | 1/1992 | Oz | |
| 5,239,984 | 8/1993 | Cane et al. | |
| 5,363,839 | 11/1994 | Lankford | |
| 5,527,261 | 6/1996 | Monroe | 600/109 |
| 5,527,262 | 6/1996 | Monroe et al. | |
| 5,541,398 | 7/1996 | Hanson | 235/472 |
| 5,609,561 | 3/1997 | Uehara | 600/112 |
| 5,630,783 | 5/1997 | Steinberg | 600/158 |
| 5,682,199 | 10/1997 | Lankford | 348/72 |
| 5,740,801 | 4/1998 | Branson | 600/407 |
| 5,762,605 | 6/1998 | Cane et al. | 600/112 |
| 5,789,289 | 3/1999 | Yarush et al. | 600/109 |
| 5,859,628 | 11/1995 | Ross | 345/173 |
| 5,873,814 | 2/1999 | Adair | 600/109 |
| 5,877,819 | 3/1999 | Branson | 348/701 |
| 5,885,214 | 3/1999 | Monroe | 600/112 |
| 5,902,230 | 5/1999 | Takahashi et al. | 600/109 |

*Primary Examiner*—John P. Leubecker
*Attorney, Agent, or Firm*—Wall Marjama Billinski & Burr

[57] ABSTRACT

An imaging instrument includes a compact hand-held housing having an electronic imaging element supported within a housing, and a plurality of interchangeable instrument heads separably attachable to the housing. Each of the instrument heads includes an optical system disposed in alignment with the electronic imaging element along an instrument viewing axis. Preferably, the instrument further includes an integral display for displaying at least one captured or real-time video image as viewed through the instrument head of choice. The instrument includes a controller with sufficient programmable logic to capture and store a plurality of imaging images which can be transferred along with audio and/or annotation data relating to a captured image. Corresponding video and audio data can be then transferred using a receiving cradle to a computer which contains software which organizes the stored data for further processing. In a preferred example, the audio files can be transcribed through a network utilizing voice recognition software.

73 Claims, 39 Drawing Sheets

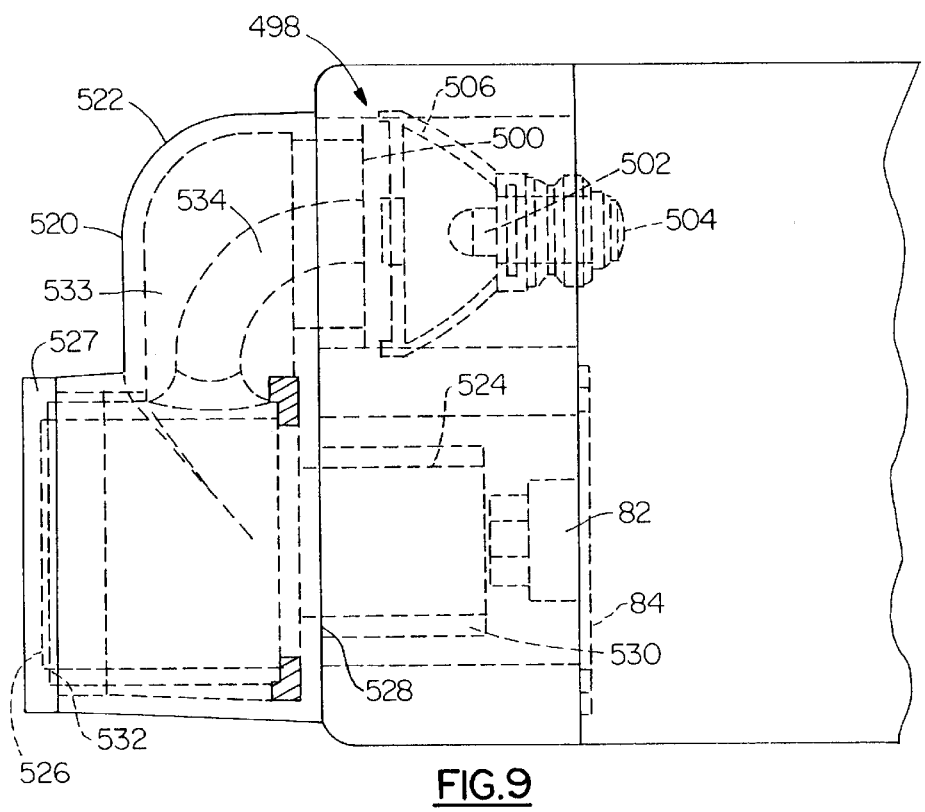
FIG.9
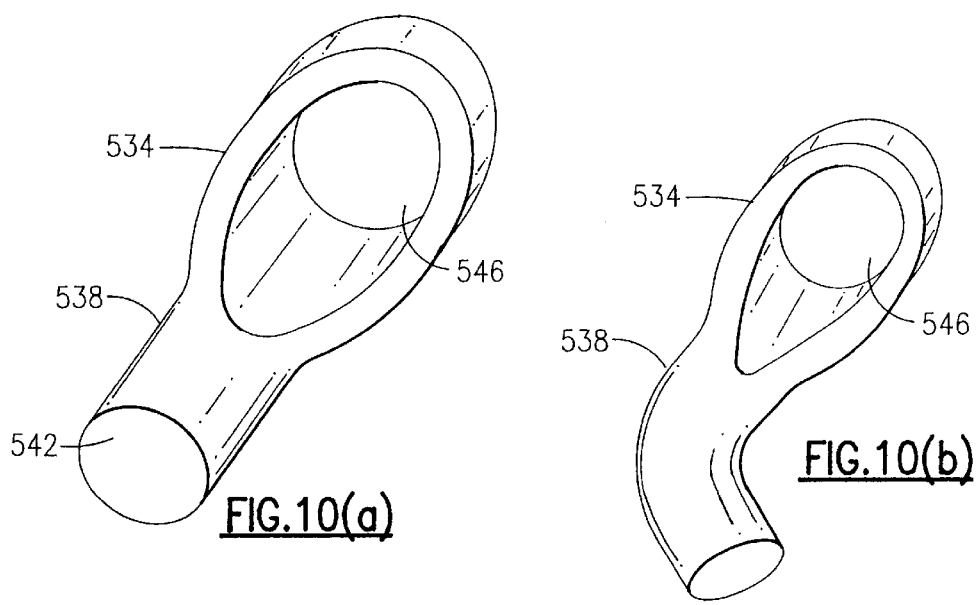
FIG.10(a)
FIG.10(b)

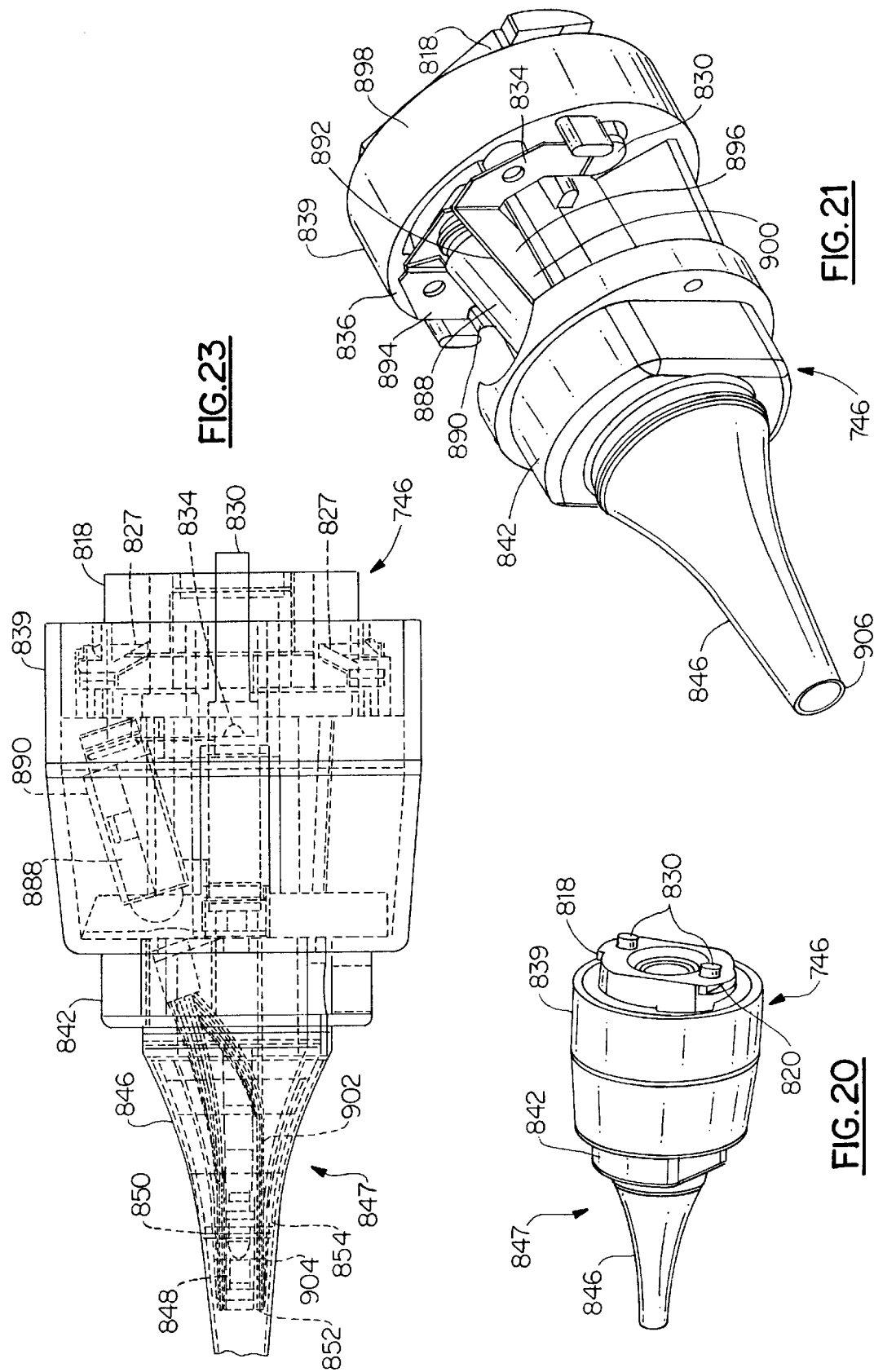

WelchAllyn

| | |
|---|---|
| PATIENT NAME: | MADELEINE PERKINS |
| PATIENT ID: | 314-15-9527 |
| PROVIDER NAME: | DR VITO LOSITO |
| EXAM DATE: | 3 FEBRUARY, 1998 |

DAVE PERKINS 8424

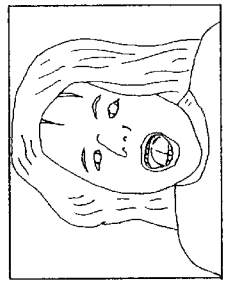

1:15:56 PM  PATIENT COMPLAINED OF UNSIGHTLY BIRTH-MARK ON PALM OF RIGHT HAND. IT APPEARS TO BE A BENIGN HEMANGIOMA. NEWLY FORMED BLOOD VESSELS ARE READILY APPARENT IN THE BRIGHT, PROTRUDING AND SHARPLY DEMARCATED LESION. SINCE THE PATIENT HAS HAD FOR MANY YEARS, WE WILL EVALUATE IN SIX MONTHS.

 WAVE SOUND
AUDIO 1:
2/3/98
1:15:56 PM
47 SECONDS

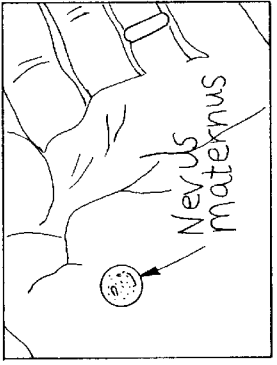

IMAGE 1: NEVUS MATERNUS LEFT HAND

1:43:30 PM  BP 126/86, P 82, Wt 190, HEENT: PERRLA, EOMS INTACT, TMs NL, OROPHARYNX BENIGN. NECK: SUPPLE W/O JVD, BRUITS, OR THYROMEGALY. CHEST: BS CLR TO PERCUSSION AND AUSCULTATION. HEART: WNL W/O GALLOP, MURMUR, RUB, CLICK OR IRREGULARITY. EXT: W/O EDEMA, PULSES INTACT.

 WAVE SOUND
AUDIO 2:
2/3/98
1:15:56 PM
34 SECONDS

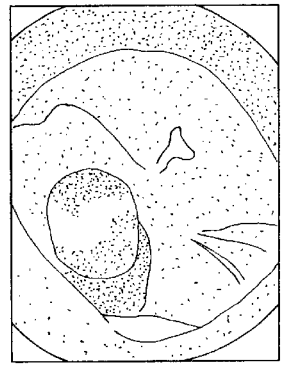

IMAGE 2: RIGHT TM, NORMAL

☒ APPROVED: *Dave Perkins*   VITO LOSITO MD

FIG. 43

COMPACT IMAGING INSTRUMENT SYSTEM

CROSS REFERENCE TO RELATED APPLICATIONS

This application is based on provisional applications U.S. application Ser. No. 60/043,374, filed Apr. 4, 1997.

FIELD OF THE INVENTION

This invention relates to the field of imaging instruments, and particularly to an imaging instrument system having interchangeable instrument heads selectively used with a single instrument body or a family of instrument bodies. The instrument can allow image, audio, and other forms of data (multimedia) to be selectively captured, stored, and utilized.

BACKGROUND OF THE INVENTION

A number of hand-held diagnostic instruments are commonly known in the medical field for examining a patient, such as those which are used during routine physician office visits. These instruments include, among others, skin surface microscopes which are used for diagnosing skin disorders, otoscopes permitting examination of the ear canal and tympanic membrane, and ophthalmoscopes for examining the eyes. Each of the above instruments have uniquely inherent features to allow an effective examination of the area of interest. Skin surface microscopes, for example, include a distal optical element having a relatively large diameter (e.g. approximately 15 mm) for direct placement onto a wart, lesion, or other skin disorder. Otoscopes, on the other hand, include a frusto-conical insertion portion, including a safety speculum, which prevents insertion beyond a predetermined distance into the ear canal.

It has since become desirable for a patient to be able to witness a primary care or other examination along with the physician. Therefore, videoized versions of the above diagnostic instruments have been developed, such as those described in U.S. Pat. No. 5,363,839, issued to Lankford, U.S. Pat. No. 5,239,984, issued to Cane, et al, and U.S. Pat. No. 4,947,245, issued to Ogawa, et al. In each of the referenced instruments a miniature video camera, such as a CCD or other electronic sensor, is positioned either within the interior of the instrument or adjacently coupled thereto. The electronic sensor includes a light receiving surface or substrate which receives a focused optical image of a target of interest through a specifically designed viewing system, such as a rod lens, objective or other form of lens positioned, typically in the distal end of the instrument.

A separately disposed light box or other source of illumination, provides white light through a sheathed cable tethered to the proximal end of the instrument. The cable includes an optical fiber bundle for directing the light specifically to the distal tip of the instrument, as well as electrical conductors for powering the electronic sensor. The electronic sensor, in turn, creates an analog or digital electrical signal which is remotely transmitted to a processor containing appropriate circuitry for converting the transmitted electrical signal into a video monitor-ready (PAL, NTSC) format. The processed video signal is then separately displayed on a remote monitor. The use of videoized systems has become increasingly popular and has since taken on the term "telemedicine".

Videoized diagnostic instrument systems, like those described above, are quite expensive, with each system requiring a separate diagnostic instrument, along with dedicated cabling, light source, signal processor and video peripheral device(s). In addition, each system also requires a significant space allocation, posing a separate problem considering that space is already at a premium in physician's offices and other environments where such systems would be typically be used. It is therefore desirable to provide a diagnostic instrument system which is capable of performing multiple examinations.

It is another perceived desire in the field to make such telemedicine systems sufficiently portable; for example, to allow examinations to take place outside the "normal doctor's office". Along with this need, is a similarly recognized need to allow portions of the system to be compactly arranged without the need for separate peripherals or connecting devices.

Improved organization of patient records is yet another current need in the medical field. To date, creation and maintenance of patient files has been largely a manually managed activity. Data which can form a part of the overall patient record, however, can take on a number of different forms. For example, it has been known that data can be accumulated in a number of forms, particularly with the advent of telemedicine involving image capture, such as using the above described videoized instrument systems.

In addition, physicians, such as family practitioners, surgeons, etc., invariably record notes during a patient visit and examination. In some instances, of course, the physician may write information directly into the patient's file. The course of usual practice, however, is to record events of an examination using a hand-held recording device. The taped notes are then later transcribed and then added to the patient's file. Throughout the course of a single day, however, it is possible that a physician may see as many as 40 patients. This kind of volume makes the task of compiling and transcribing notes difficult, or at a minimum time consuming, either for the physician or for the physician's staff. The creation of patient records incorporating several types of data, including audio and video data, is even more difficult.

To date, though there are a number of transcripting apparatus available, none conveniently combine audio data with other forms of collected data, such as captured images, sketches by the physician, or data obtained from other instruments to be retained and used in compiling and assembling complete examination records which can then be effectively stored and maintained.

SUMMARY OF THE INVENTION

Accordingly, it is a primary object of the present invention is to improve the present state of the art of diagnostic or other suitable instrument systems.

Another primary object of the present invention is to provide a single or family of convertible diagnostic devices which allow varied clinical, as well as industrial uses, to be performed.

It is yet another primary object of the present invention to provide greater flexibility to a physician or other care-giver by providing a video instrument which is versatile, simple to modify, and utilizes less space than other known systems.

It is yet another primary object of the present invention to provide a data management system, for medical or other records, such as inspection, etc, using an instrument which is capable of capturing and storing multiple forms of data input which can be effectively transferred into a central network capable of linking the data into accumulated data records which can be updated and maintained automatically.

Yet another primary object of the present invention is to provide an instrument capable of storing various forms of data (i.e.: multimedia), that can be adaptively interconnected with a plurality of output devices to allow transfer and subsequent processing of a plurality of stored data inputs.

It is yet another primary object of the present invention to provide a data or records management system in which a plurality of captured data files, such as digital audio files, can be subsequently transferred and transcribed, the results of the transcription being transferrable directly into a patient record.

Therefore and according to a preferred aspect of the present invention, there is provided a hand-held video instrument capable of performing multiple examination tasks, said system comprising:

an instrument body including an interior;
a plurality of instrument heads interchangeably mounted to said instrument body, without requiring disassembly thereof;
means for releasably mounting each of said instrument heads to said instrument body;
optical viewing means for viewing a target of interest, said optical viewing means including at least one optical element in at least one of said instrument body and said plurality of instrument heads, said viewing means having a defined viewing axis; and
electronic imaging means including an electronic sensor disposed along said viewing axis for receiving an optical image of said target from said optical viewing means.

According to a preferred embodiment, each of the instrument heads include viewing optics which focus an optical image onto an electronic sensor, the sensor being situated adjacent the front or distal face of the instrument body. The instrument head can similarly, however, be mounted to other interface surfaces of the instrument body.

Each instrument head is releasably attachable to the instrument body using a latch mechanism, wherein the electrical contacts for an illumination assembly and/or imaging assembly are disposed in the mechanism and are not enabled until the latch has secured the instrument head of choice to the front face of the instrument body.

A light source is provided, either in the instrument head or in the instrument body, to illuminate the target of interest. According to one preferred embodiment, the instrument heads include the illumination source, while in another embodiment, a lamp assembly or other light source is provided in the instrument body.

In yet another preferred embodiment, the CCD or other electronic sensor can be retained with the instrument body to be mainly used with the family of instrument heads. In another embodiment, the imager can be positioned directly within at least one instrument head, with the instrument body having suitable electrical contacts for powering the imager, as well as the illumination source.

Other instrument bodies can additionally be provided which serve as camera platforms to provide additional versatility for clinical and/or industrial applications, such as for borescopes and the like.

According to another preferred aspect of the present invention, there is provided a hand-held imaging instrument comprising:
a compact housing including an interior;
at least one instrument head mounted to said housing;
means for viewing a target of interest, said viewing means including at least one optical element in at least one of said instrument body and said at least one instrument head, said viewing means having a defined viewing axis;
image capture means including an electronic sensor disposed along said viewing axis for receiving an optical image of said target from said viewing means; and
display means integral with said instrument housing for displaying at least one image of the target of interest captured by said image capture means.

Preferably, the instrument body further includes means for storing at least one image and for capturing, storing and playback of audio data corresponding to at least one captured and stored image. Alternately, a particular instrument can include means for selectively utilizing data other than videoized data, such as obtained from stethoscopes, etc., and/or other forms of data, wherein the data can selectively be linked to other data input, including but not limited to video data.

More preferably, the described instrument can include a plurality of interchangeable instrument heads which are releasably mountable to the instrument, each of the instrument heads having a unique viewing system for allowing multiple types of examination to be performed using the same instrument.

More preferably, the instrument is part of an overall data or records management system in which the instrument is interconnected with a receiving cradle. The receiving cradle acts as a docking station having means for allowing data transfer between the instrument and an external source to allow transfer of audio, video and other data files stored in the instrument or the external source which can, for example, be part of a single computer or computer network. In this manner, protocols, operating instructions, etc., as well as data can be transferred directly to the instrument according to one embodiment or data and the like can be transferred from the instrument.

Preferably, the data is transferred, according to a particular aspect of the present invention, to an immediate or local computer or PC utilizing software which arranges the data into a script template, such as a patient chart of convenient architecture, including allocation for voice, video and annotation data; for example, as part of a local database. The local database, would for example, contain patient files for a specific physician's office.

In addition, the transferred voice or WAV files can be further transferred into a central data network (e.g. a server) utilizing a global database for tying in a plurality of similar diagnostic or other suitable instruments. The central database, for example, can handle raw voice data from a particular instrument communicated remotely and transfer a transcribed report back to the local physician.

According to a preferred feature of the described data management system includes software which is capable of discriminating a captured video image for known 1D or 2D barcode symbology or for pattern recognizable data. This allows the instrument to tag data files automatically without requiring separate manual input from the user.

According to a preferred embodiment, each of the instrument heads include separate and unique viewing optics which focus an optical image onto an electronic sensor, the sensor being preferably situated adjacent the front face of the instrument body.

Preferably, each instrument head is releasably attachable to the instrument housing using a latching mechanism, in which attachment automatically transmits power to the instrument head, such as for activating a contained illuminating lamp, for example. According to one preferred embodiment, the instrument heads include a source of illumination though alternately the illumination source can also be a contained part of the instrument.

Preferably, the instrument heads are removably attachable to a single and compact instrument housing having both image capture means as well as an integral display element for allowing the operator to uniquely view a target of interest as perceived through the instrument head. More preferably, the instrument includes other features, such as allowing annotation data to be added to a displayed image of interest as well the capability of storing and transmitting stored forms of data, including audio data.

According to yet another preferred aspect of the present invention, there is described a record management system comprising:

a diagnostic instrument including a plurality of instrument heads, each of said instrument heads having an optical system for directing an image onto an electronic sensor disposed in said instrument and display means for displaying at least one directed image and data capture means for capturing audio and video data;

means for transferring data files from said instrument and for moving said files to a processing means, said processing means including means for transcribing notes from said audio files; and for accumulating data from said instrument into a record format.

According to a preferred aspect, there is described a method for transcribing a plurality of record notes, comprising the steps of:

storing data using a diagnostic instrument, said instrument having digital camera means and display means contained therein, as well as means for taking audio data corresponding to a displayed video image;

placing the instrument into a docking station, said docking station being capable of extracting audio data files from the diagnostic instrument moving the audio data files to a central processing station; and using voice recognition software to process the transcription notes, the program preferably being able to recognize and utilize learn technology based on a given voice being recognized for processing;

creating transcriptions which can be associated with a patient file having at least one video image attributed thereto.

An advantage of the present invention is that an examination room videoized system is provided which allows multiple types of examination to be performed in a simple and efficient manner using a single instrument body and interchangeable instrument heads.

Another advantage of the present invention is that multiple instrument heads can be selectively and simply interchanged with a single instrument body to provide versatility and to provide the advantages of multiple videoized systems without a significant impact beyond that of a dedicated videoized diagnostic system.

Another advantage of the present invention is that a system as described allows multiple videoized examinations to be performed in the space envelope used by a single videoized system, allowing the physician to more efficiently improve the capabilities of the office.

Yet another advantage of the present invention is that a system as described can be easily expanded, is easier to replace in the case of breakage of one of the instrument heads, and is much more inexpensive than furnishing multiple diagnostic systems.

Still another advantage of the present invention is that an examination room videoized system is provided allowing multiple types of examinations to be efficiently performed using a single instrument body having a plurality of interchangeable instrument heads.

More advantageous is that a multiple of instrument heads, each having capability of performing a different type of examination, can be selectively and simply interchanged on a single instrument for use. The system, therefore, dramatically increases versatility while maximizing use of space. Moreover, the instrument is portable, meaning that examinations are not confined to a dedicated location, such as a doctor's office.

Still another advantage of the present invention is that the described system allows multiple examinations to be performed in a space envelope which is smaller than conventionally known videoized systems. The instrument also includes an integral display and means for compactly storing a series of images, or of displaying real or stored images and playback of captured audio-related data. This capability allows the physician to more efficiently improve the capabilities of the office. In addition, the instrument is preferably linkable to a PC, a PC network or other peripherals capable of using data retrieved from the instrument. Yet, the physician or other user of the instrument can use the videoized instrument from literally any location without restriction, for example, to an office setting.

Yet another advantage is that the described instrument includes an integral display element. More preferably, annotation notes relating to at least one captured videoized image can be made using the display, the annotation data being stored along with corresponding video and/or audio data relating to a patient.

Yet another advantage of the present invention is that the described system can be easily expanded, allows simple replacement or updating of components, and is much more inexpensive than furnishing multiple diagnostic or other systems.

Still another advantage of the present system is that numerous types of data including imaging data, audio data, and annotation data can be easily stored, transferred, and utilized. This storage allows the creation of a "multi-media" data file and allows efficient creation and maintenance of records provided in a useful format which incorporates each data type within the confines of a specific record.

Yet another advantage is that the above described system can be easily adapted into a multimedia data management system. According to one specific example, a transcription service can be created allowing audio data captured and stored by the instrument(s) to be added into a central network having voice processing software using a cradle or dictating station which is tied to a local PC and the PC network. In a preferred embodiment, transcribed data can then be processed and returned to the physician without tedious review of previous data records, providing improved reliability and accuracy of records, and time saving for the physician. As will become apparent, however, local use of the audio data provides a more efficient means for locally performing transcription as well, such as by a member of a physician's staff.

Yet another advantage of the described data management system is that overall transcription time can be reduced in that the doctor can immediately place the patient, physiology, notes, and transcription.

These and other objects, advantages, and features will be described in the following Detailed Description of the Invention which should be read in conjunction with accompanying drawings.

BRIEF DESCRIPTION OF THE DRAWINGS

FIG. 9 is a partial side sectional view of the instrument body of FIG. 8, including an attached surface microscope head in accordance with a separate embodiment of the present invention;

FIGS. 10(a) and 10(b) are perspective views of an illumination light pipe used in accordance with the surface microscope head of FIG. 9;

FIG. 20 is a side view of the otoscopic instrument head shown in FIG. 14;

FIG. 21 is a front isometric partially cutaway view (enlarged) of the otoscopic instrument head of FIG. 20;

FIG. 23 is a sectional view of the otoscopic instrument head of FIGS. 20–22;

FIG. 43 is a sample data sheet created using the data management system shown in FIGS. 34, 35 and 38–42.

DETAILED DESCRIPTION OF THE INVENTION

The following discussion describes the present invention according to a number of specific embodiments. As will be apparent from the following discussion, however, there are many other modifications and variations which can be employed by those of skill in the field embodying the concepts which are described herein. In addition, though the presently described embodiments relate specifically to the medical field, it should be readily apparent that other applications utilizing numerous forms of data input including manufacturing, quality control, inspection, engineering, and inventory, among others, can effectively utilize the concepts presented herein.

Figure 1:
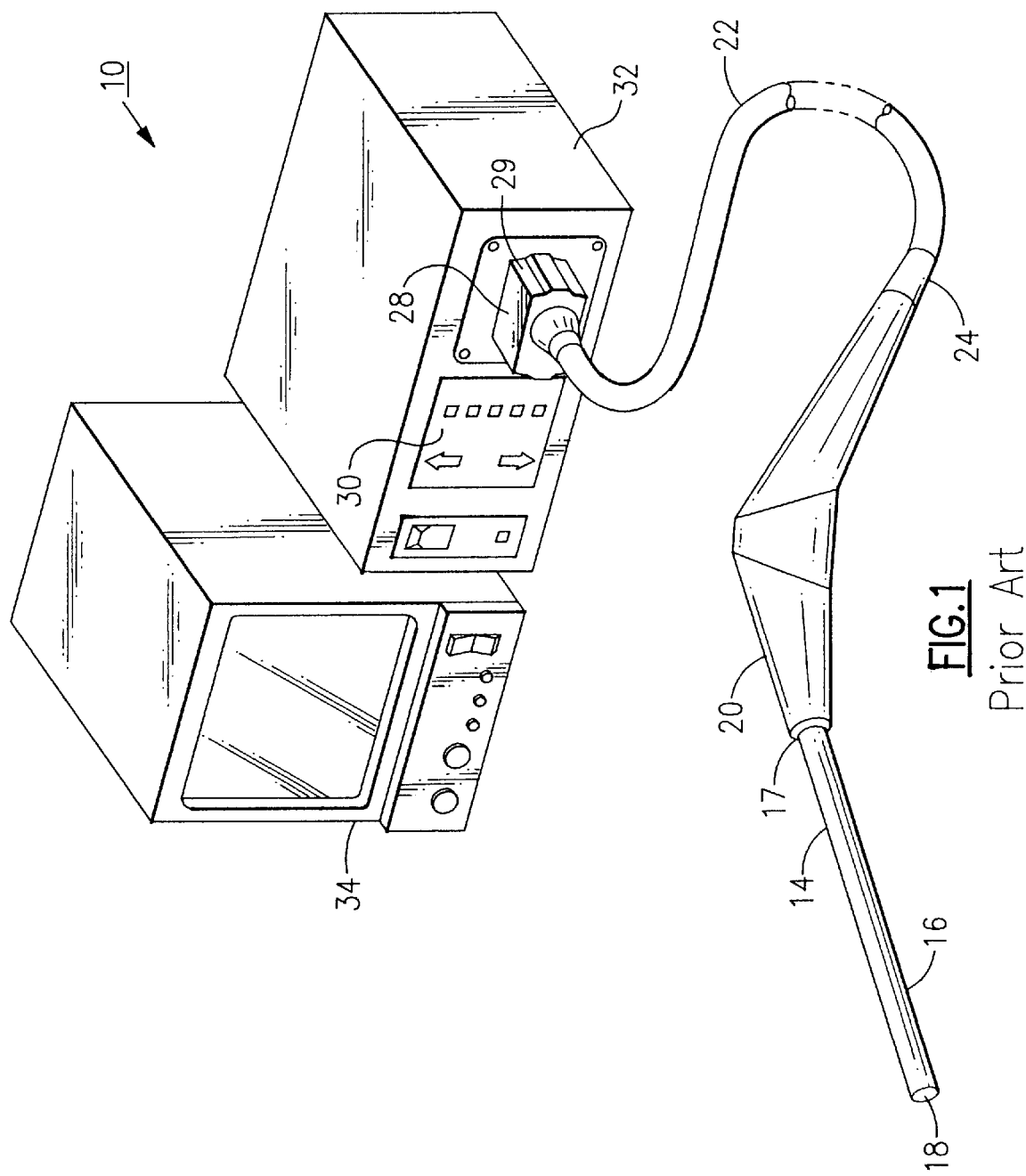
FIG. 1 is a front isometric view of a known medical diagnostic instrument system in accordance with the prior art.

Turning to FIG. 1, there is shown a video medical diagnostic instrument system in accordance with the prior art. The instrument system 10 includes a medical diagnostic instrument 14, an endoscope (ie: a video laparoscope) being shown, defined by an elongate instrument body 16 having a distal end 18 and an opposite proximal end 17 attached to a handle section 20. An electronic sensor or element (not shown), such as a CCD (charge coupled device), is disposed within the instrument body 16 and receives an optical image of a target of interest through an imaging system, such as a relay lens system (not shown) or other known arrangement, in a conventional manner. The electronic sensor includes support electronics which convert the optical signal into an electrical signal which is transmitted along a sheathed cable 22 depending from the proximal end 24 of the handle section 20.

According to the above-described system, a video processing module 28 forms the proximal end of the sheathed cable 22, the module containing processing electronics for converting the transmitted electrical signal into a video monitor-ready (PAL, NTSC, etc.) signal. The video processing module 28 is attached into a receiving cavity 29 of a light/power box 32 containing a high output light source, such as an arc lamp (not shown) or other source of white light. The light from the high-intensity light source is transmitted from the light box 32 through an optical fiber bundle (not shown) contained within the sheathed cable 22, and guided into the diagnostic instrument body 16 to the distal end 18 thereof. The light/power box 32 also serves to furnish power to the diagnostic instrument 14 through electrical connectors, also contained within the sheathed cable 22, the power/light box being operated by a control panel 30.

In use, a processed video signal of the target of interest is displayed by an interconnected video monitor 34 which is connected to the light/power box 32 to allow viewing, by a physician and patient(s). Other peripheral devices, (not shown) such as a video printer, a video tape recorder, a PC, etc., can also be substituted into the above described instrument system.

As recognized, the above diagnostic instrument system 10 introduces a number of discrete components and requires a significant spatial footprint typically restricting the use of the system to a dedicated area, such as a physician's office, an emergency room, etc. Though the above laparoscopic system is dedicated to a particular target of surgical interest, in this case, the abdominal cavity, other types of diagnostic instruments, such as otoscopes, colposcopes, and dermatoscopes, among others, are required for performing other types of examinations that are typically done during a patient visit. That is, it is not uncommon that a variety of different examinations, (ear, eye, throat, skin) could be performed in a single family practitioner visit. The ability to electronically capture and archive images for each type of examination would be desirable, allowing the patient and the physician to both view a target of interest, but as noted above, typically a separate dedicated system is required for each instrument.

Figure 2:
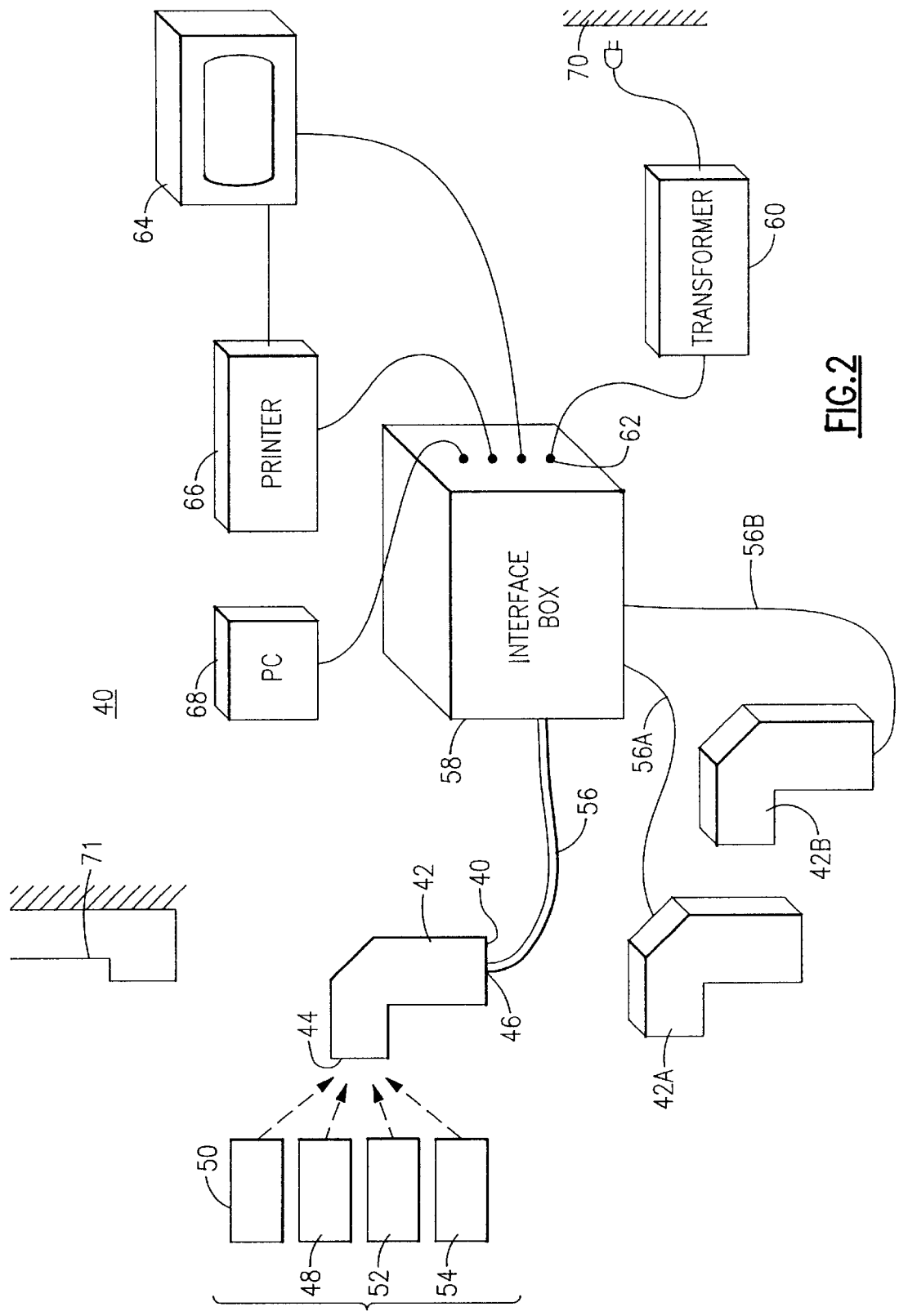
FIG. 2 is a perspective view of a video instrument system in accordance with a preferred embodiment of the present invention.

According to FIG. 2, there is provided a diagrammatic view of a medical diagnostic instrument system 40 according to a first preferred embodiment of the present invention including a primary instrument body or housing 42 having a front or distal face 44 and a proximal end 46. A plurality of instrument heads 48, 50, 52 and 54 are interchangeably and releasably mountable to the front face 44, the details of which will be described in greater detail below.

The instrument body 42 according to this embodiment is tethered by known means at the proximal end 46 to one end of an umbilical cable 56, the remaining end of which is attached to an interface box 58. The interface box 58, in general, acts as a conduit to supply electric power to the described system 40 from a transformer 60 connected to a conventional wall outlet 70, though it is conceivable that other electric power sources, such as batteries and the like, could be alternately utilized. A battery powered instrument is described in a succeeding embodiment of this invention.

The interface box 58 includes a number of attachment ports 62 to enable interconnection to a number of video peripheral devices. For purposes of this embodiment, a video monitor 64, a video printer 66, and a personal computer 68 are shown, each of which is capable of receiving a processed video signal from the diagnostic instrument, as is described in greater detail below. Preferably, the interface box 58 includes additional ports (not shown), allowing a plurality of instrument bodies 42A, 42B to be similarly interconnected by umbilical cables 56A, 56B. Details relating to the method of interconnection are well known in the field and require no further discussion for purposes of the present invention.

According to this embodiment, a conventional wall mount 71 is preferably provided for receiving and retaining an instrument body 42 or bodies 42A, 42B when the instrument is not in use. The wall mount 71 may also be suitably equipped to provide a signal to turn the illumination and video mechanism off upon engagement therewith; that is, to shut the unit off automatically when the instrument is no longer in use.

Figure 3A:
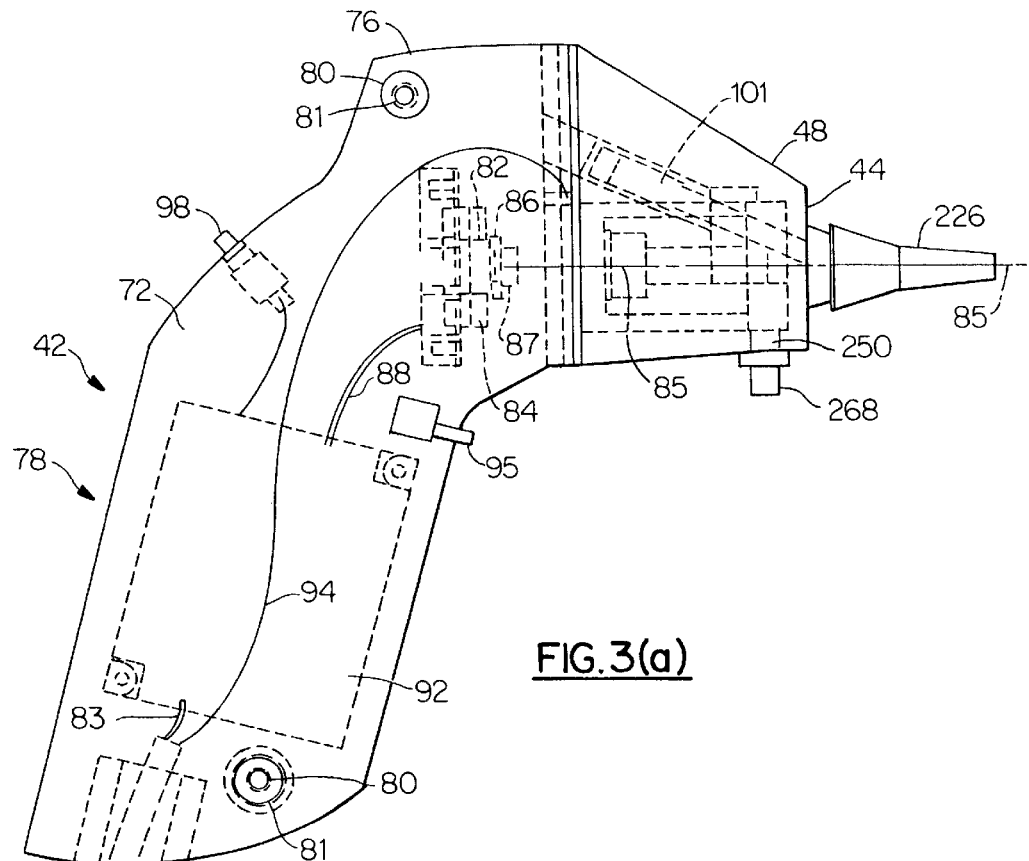
FIG. 3(a) is a cross sectional view of the instrument body and an attached instrument head used in the system of FIG. 2, according to a preferred embodiment.

Referring now to FIG. 3(a), the instrument body 42 according to this embodiment includes a substantially hollow interior 72 defined by a hand-holdable section 74 and an instrument section 76. The hand-holdable section 74 assumes the shape of a pistol grip, though other convenient shapes or designs can alternately be used. Each of the two sections 74, 76 are integral, the instrument body 42 having a separable two-part housing 78 which is attached using threaded fasteners 80 through holes 81 provided at either end. The interior 72 of the instrument section 76 is sized for containing a miniature video camera, such as a charge coupled device (CCD), CMOS, or other electronic sensor 82, having a substrate 84 defining an image plane for receiving an optical signal along a viewing axis 85, extending to the front face 44, FIG. 2, of the instrument body 42. For purposes of this specifically described embodiment, a compact Hitachi VK-C25A color video camera is provided. An infrared filter 86 and plano lens 87, each shown in phantom, are disposed in front of the electronic sensor 82, and aligned with the viewing axis 85.

A series of transmission lines 88 are soldered or otherwise connected to a series of connector pins (not shown) extending from the rear of the electronic sensor 82, by known means, to an integrated circuit board 92 disposed in the hand-holdable portion 74. The circuit board 92 contains video processing circuitry (not shown) for converting the electrical signal from the electronic sensor 82 into a video signal which is then transmitted from the circuit board along the transmission lines 83 extending through the umbilical cable 56 to the video peripheral devices 64, 66, 68, FIG. 2, through the interface box 58, FIG. 2. The umbilical cable 56, as partially shown in FIG. 3(a), includes a flexible covering 90 and is sized for also containing additional transmission lines 94 for transmitting electric power from the transformer 60, FIG. 2, to the instrument section 76.

The instrument body 42 also contains a power ON/OFF switch 95 comprising a depressible portion extending through a slot (not shown) in the two-part housing 78, as well as a similarly disposed white balance button 98, the purpose of which will be described below.

Still referring to FIG. 3(a), one of the instrument heads; in this instance an otoscopic instrument head 48, is shown which is releasably attachable to the front face 44 of the instrument body 42. The instrument head 48 has an illumination assembly including a supported halogen lamp or other suitable light source, and an imaging system retained therein. A major feature of the present invention relates to the powering of the illuminating assembly using a latching mechanism described in detail below. Additional details also follow pertaining to features of each interchangeable instrument head 48, 50, 52, 54, as well as the operation of the diagnostic system 40 of this embodiment.

Figure 3B:
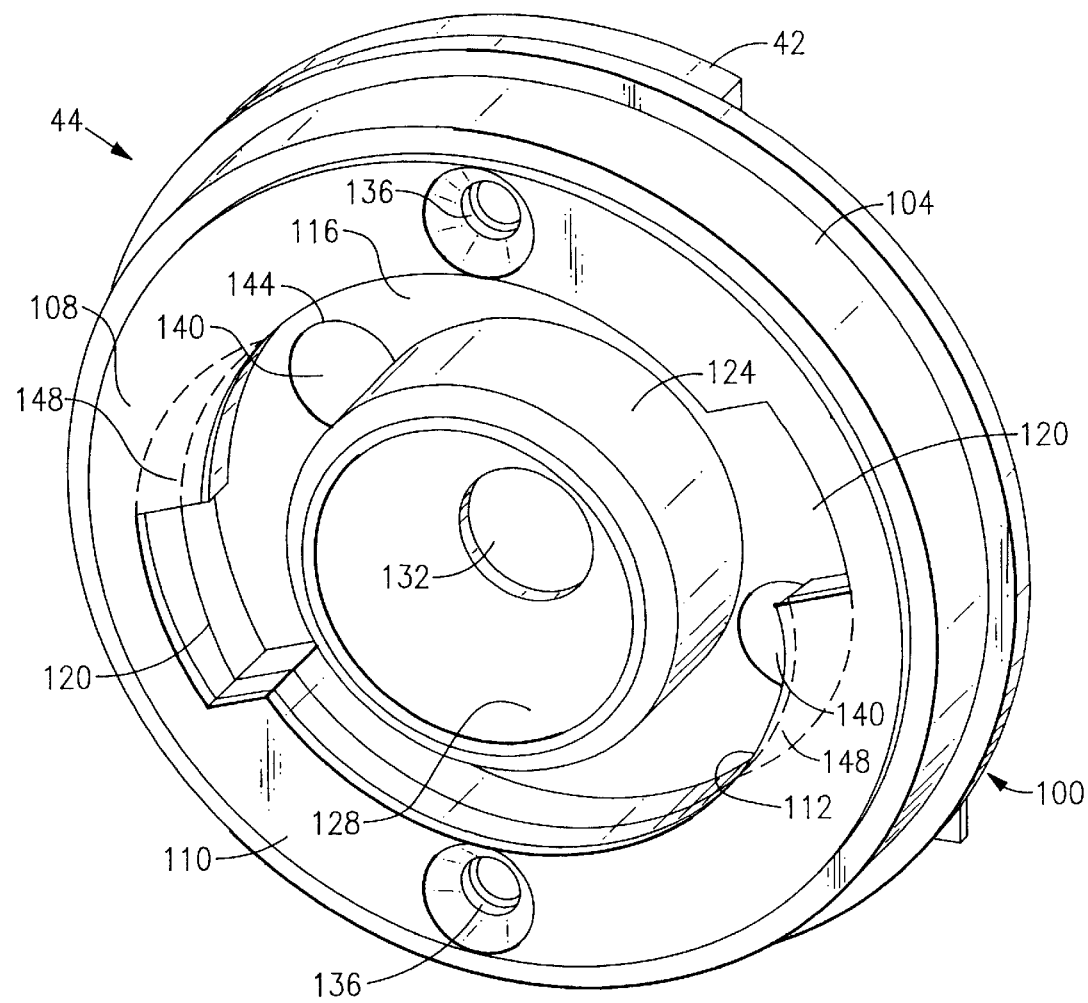
FIG. 3(b) is a partial front perspective view of the front face of the instrument body of FIG. 3(a), illustrating one half of a releasable latching mechanism.

Referring now to FIG. 3(b), the front face 44 of the instrument body 42 includes a base portion 100 defined by an open ended distally extending section 104 having a circular metal alignment plate 108 mounted therein, the plate having a substantially flat contact surface 110. The alignment plate 108 also includes a centrally disposed and substantially circular cavity 112 having a defined bottom planar surface 116. As noted, the cavity 112 is substantially circular, with the exception of a pair of diametrically opposed tab sections 120.

A cylindrical pilot section 124 projects distally from the planar surface 116, the section comprising a circular cross section and an open end 128 centrally disposed about a center aperture 132. The center aperture 132 is centrally disposed on the front face 44 of the instrument body 42 and communicates with the interior of the instrument section 76, FIG. 3(a). Furthermore, the center aperture 132 is aligned with the viewing axis 85, FIG. 3(a).

The metal alignment plate 108 is securely fastened to the base portion 100 by engagement of a pair of threaded fasteners (not shown) into corresponding diametrically opposed holes 136. The holes 136 are preferably countersunk to ensure the planarity of the contact surface 110.

A pair of electrical contacts 140 connected to the power transmission lines 83, FIG. 3(a), are provided in a pair of openings 144 provided on the planar recessed surface 116. According to this embodiment, the openings 144 are also diametrically opposed, and are disposed adjacent the tab sections 120. The contacts 140 are preferably flush with the planar surface 116. A pair of stops (not shown) are provided within respective annular slots 148, shown in phantom, extending radially from the tab sections 120, the purpose of which is described below.

As noted above, and depicted in FIG. 2, a number of instrument heads 48, 50, 52, and 54 are releasably attachable to the front face 44 of the instrument body 42, the description of which is now attended to. Each of the above instrument heads include an identical latching mechanism for releasable attachment to the front face 44 of the instrument body 42. The following discussion specifically refers to the latch mechanism related to the otoscopic instrument head 48. Similar features are present in the attachment of the remaining instrument heads 50, 52, 54.

LATCHING MECHANISM

In passing and prior to describing the present latching mechanism, it should be noted that though the front facing surface of the instrument and the rear surface of the instrument heads, respectively, are the interfacing surfaces, mechanisms embodying the concepts prescribed herein can be provided using other surfaces thereof. For example, and though not shown, the instrument heads could be attached to the top of a suitable instrument body for use (e.g. a side-viewing instrument head, etc).

Figure 4A:
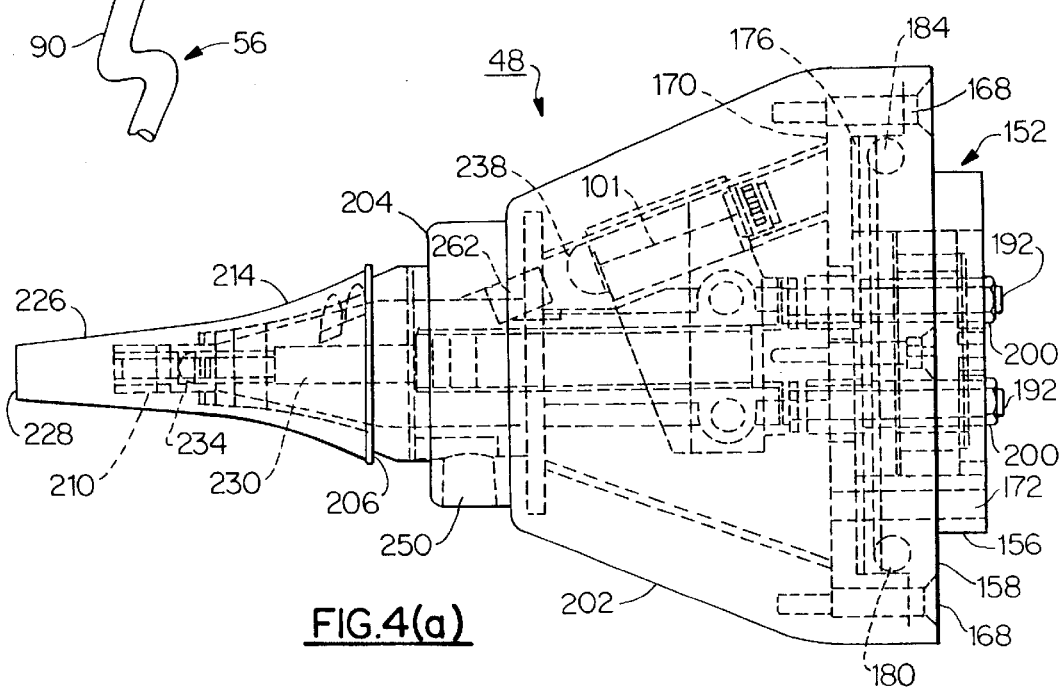
FIG. 4(a) is a side-sectional view of an otoscopic instrument head interchangeably used with the instrument body shown in FIG. 3.
Figure 4B:
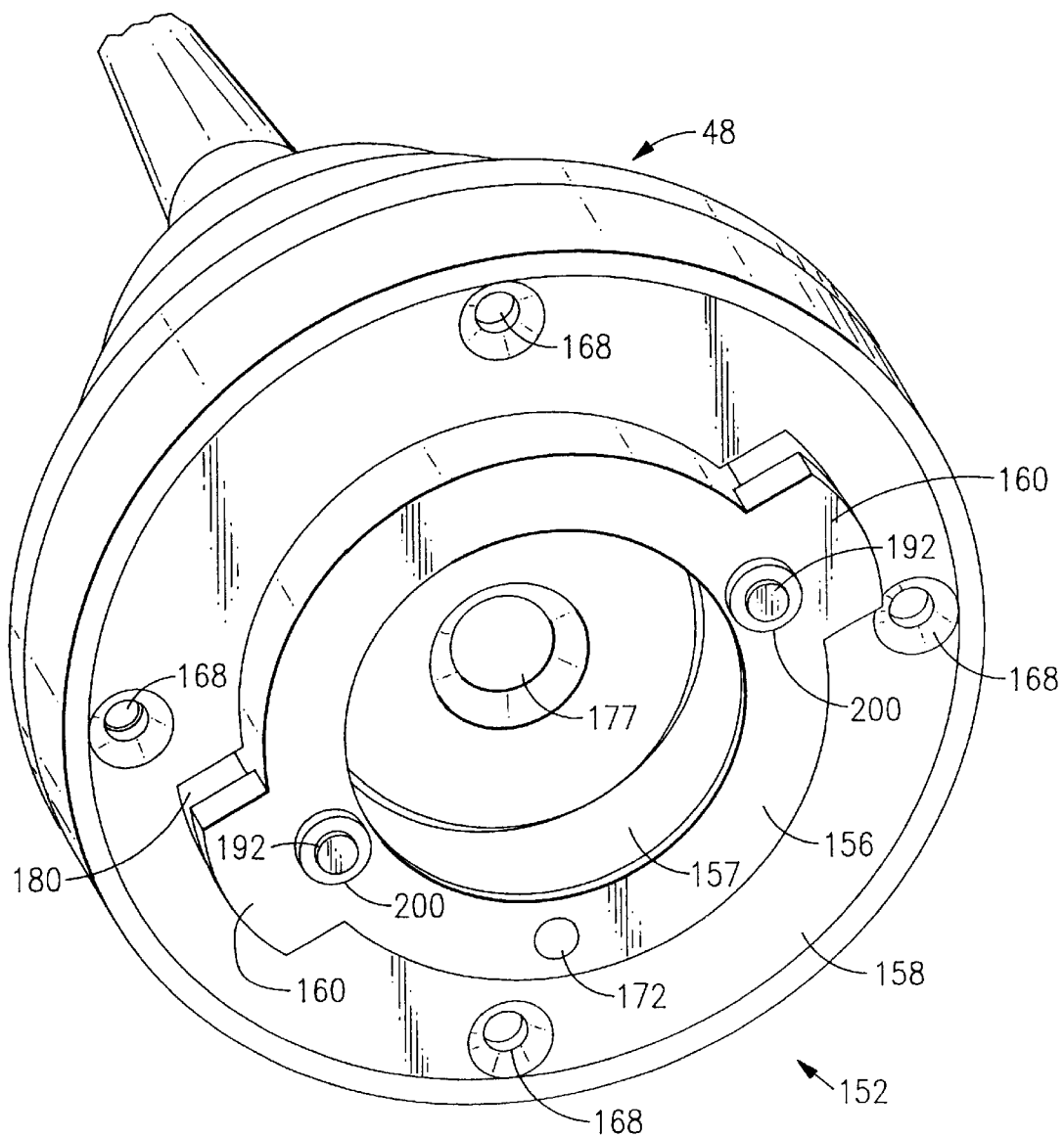
FIG. 4(b) is a rear perspective view of the otoscopic instrument head of FIG. 4(a), emphasizing the remaining portion of the preferred latching mechanism.

Referring to FIG. 4(b), the rear or proximal face 152 of the otoscopic instrument head 48 includes a ring-shaped latching member 156 having a substantially circular configuration with the exception of a pair of diametrically opposite ear portions 160. The latching member 156 is disposed within a correspondingly shaped cavity 164 provided in a flat ring 158 which is fixedly secured to the rear face 152 using a plurality of evenly spaced threaded holes 168. The threaded holes 168 are sized for receiving a corresponding number of threaded fasteners (not shown). As shown in FIG. 4(a), each of the fastener holes 168 extend into an interior wall 170 of the instrument head 48. A single pin hole 172 similarly extends into the latching member 156 and into the interior wall 170. A pin (not shown) inserted into the pin hole 172 prevents rotation of the latching member 156.

Still referring to FIG. 4(b), the latching member 156 is a cylindrical member having a pair of open ends 157 centrally disposed relative to a center opening or aperture 177 communicating with the interior of the instrument head 48. A pair of diametrically opposed cylindrical electrical contact elements 192 are slidingly attached to the latching member 156 through openings extending therethrough into the interior of the instrument head 48 for allowing axial movement thereof. A plastic insulator 200 surrounds each the contact element 192, as shown in FIG. 4(a).

As more clearly shown in FIG. 4(a), the latching member 156 is preferably made from a stainless steel and includes an inner annular shoulder portion 176 disposed within a cavity 180 formed in the interior of the rear face 152. An O-ring 184 is also disposed within the cavity 180 between the annular shoulder portion 176 and the interior surface of the flat ring 158.

Figure 4C:
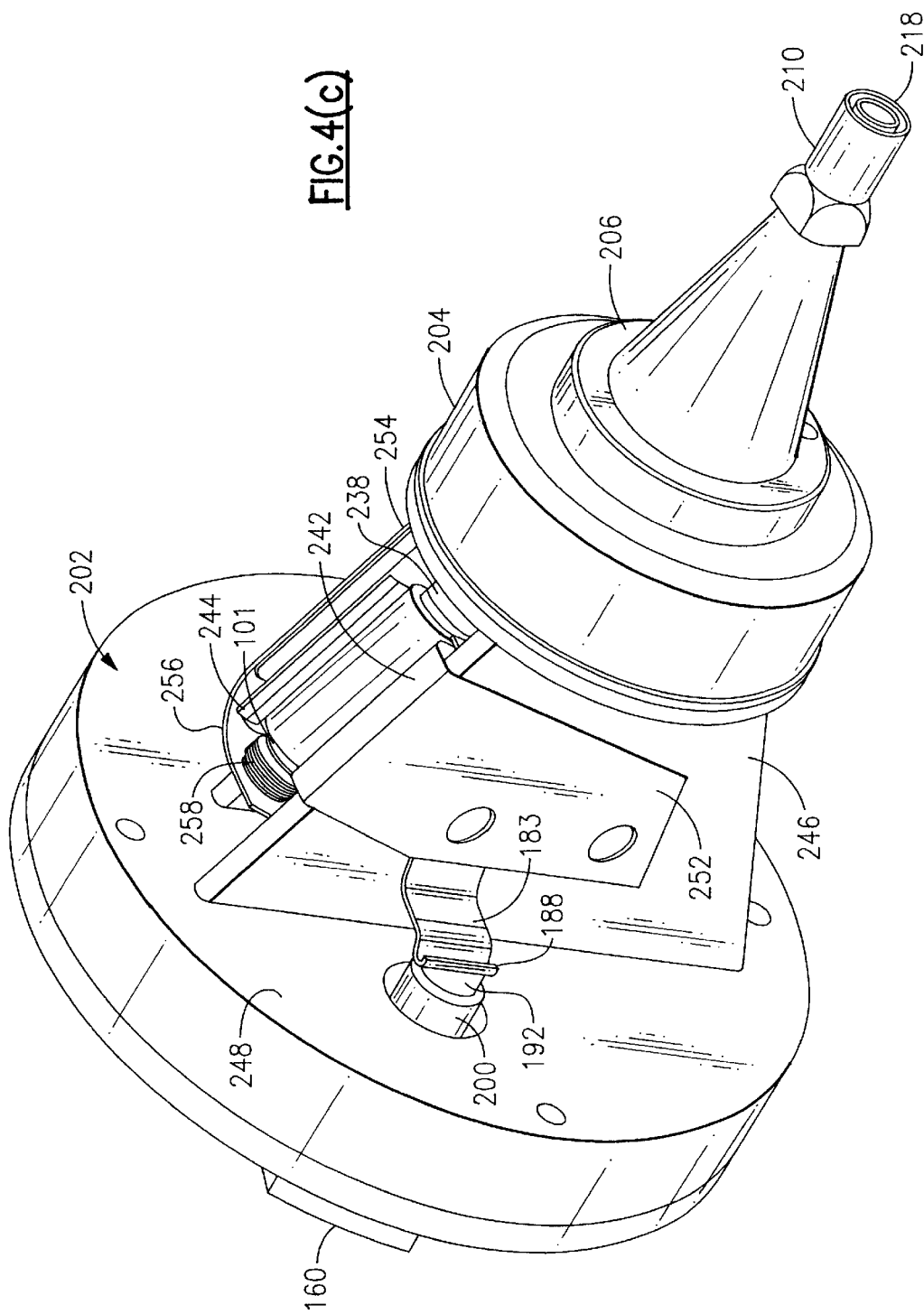
FIG. 4(c) is a partial front perspective view of the otoscopic instrument head of FIGS. 4(a)–4(b), depicting a retained lamp assembly and corresponding electrical contacts.

Referring to FIGS. 4(a), 4(b), and 4(c), the latching member 156 is intentionally biased rearwardly relative to the rear face 152 by the O-ring 184 to a first axial position. This position is most clearly shown in FIG. 4(a). The leaf springs 183 each include an engagement portion 188 at one end which is aligned with the inwardly extending end of a contact member 192 so as to supply a bearing force thereupon.

In use, the rear side 152 of the instrument head 48 is brought into engagement with the front face 44 of the instrument body 42, FIG. 3(b). The latching member 156 is aligned with the cavity 112, and more specifically the ear portions 160 are aligned with the tab portions 120. Preferably, the cavity 112, including the tab portions 120 closely match the profile or contour of the latching member 156. The engagement of the cylindrical pilot portion 124 causes the latching member 156 to be directed forwardly toward the interior of the instrument head 48 against the bias of the O-ring 184, ensuring significant contact between the flat ring 158 and the contact surface 110.

Rotation of the entirety of the instrument head 48 in a clockwise manner; that is, clockwise as perceived looking at the front face 44 of the instrument body 42, advances the ear portions 160 into the annular slots 148 until engagement with the stops (not shown). The described rotational movement causes the contact members 192 to align with and engage with the corresponding electrical contacts 140 in the instrument body 42, thereby supplying electric power to the supported lamp assembly 101.

To initiate release, a user reverses the above procedure by grasping and rotating the instrument head in the opposite (counterclockwise) direction until the ear portions 160 are aligned with the tab portions 120 in the instrument body 42. The instrument head 48 is then pulled axially away from the front face 44 of the instrument body 42, causing the latching member 156, as biased by the O-ring 184, to be moved back into the initial axial position.

As noted above and as depicted in the accompanying FIGS. 5(a), 6(a), 6(b), 6(c), 7(a), and 7(c), each of the remaining instrument heads 50, 52, and 54 according to the present embodiment include an identical latching mechanism for releasable engagement with the front face 44 of the instrument body 42. An actual engagement therebetween is also illustrated in FIG. 6(c).

OTOSCOPIC INSTRUMENT HEAD

Referring now to FIGS. 4(a)–4(d), a number of additional details pertaining to the otoscopic instrument head 42 of this embodiment are herein described. The instant instrument head 42 is defined by a substantially frusto-conical configuration including a rear housing portion 202, an intermediate housing portion 204, and an front housing or insertion portion 206 distally arranged therefrom. The insertion portion 206 includes overlapping and conically shaped inner and outer tip housings, 210, 214, each having a respective distal tip opening 218, 222. A safety speculum 226 made from a plastic material and having a distal tip opening 228 is mounted onto the conical periphery of the outer tip housing 214, also in overlapping relation thereto. A linear lens tube 230 is retained within the interior of the inner tip housing 210 extending rearwardly from the tip opening 218. A series of objective lens assemblies 234 are retained within each of the lens tubes 230.

As most clearly seen in FIGS. 4(a) and 4(c), the illumination assembly 101 includes a miniature halogen lamp 238 which is disposed within the rear housing portion 202 and press-fitted within a spring-metal receptacle 242 placed in a spaced enclosure 244 formed by a pair of supporting plates 246 mounted to a rear wall 248. The spring metal receptacle 242 forms a pocket sized for retaining the lamp 238 from one of a pair of flat sections 252, which are mounted to the exterior of the supporting plates 246.

The remaining flat spring-metal section 254 includes a curved section 256 which is disposed behind the lamp 238 and into engagement with the lamp contacts 258. Each of the flat spring metal sections 252, 254 support the leaf springs 183 such that when the contacts 192 engage the contacts 140 in the instrument body 42, FIG. 3(a), that the electrical circuit is completed, allowing the lamp 238 to be powered.

Figure 4D:
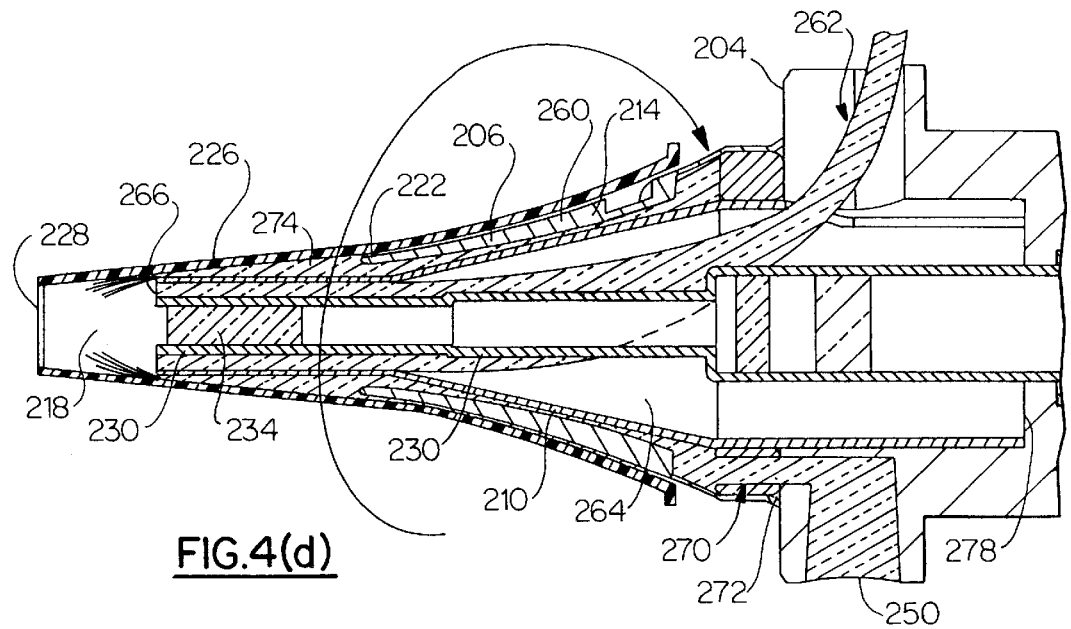
FIG. 4(d) is a partial side pictorial view of the otoscopic instrument head of FIGS. 4(a)–4(c), illustrating the respective paths of insufflating air and illumination.

Referring to FIGS. 4(a) and 4(d), light from the halogen lamp 238 is directed to one end of a bundle of optical fibers 262 (partially shown in FIG. 4(a)) which are fanned out into an annular space 264 formed between the lens tube 230 and the interior wall of the inner tip housing 210. The bundle of fibers 262 terminate at the distal tip opening 218 of the inner tip housing 210 as a polished light emitting end 266.

Still referring to FIGS. 4(a) and 4(d), an insufflation port 250 is provided in the intermediate housing portion 204 and sized to receive a fitting 268, shown only in FIGS. 3(a) and 4(a). The insufflation port 250 defines one end of a passageway extending into the interior of the insertion section 206. The fitting 268 allows a known depressible pneumatic bulb (not shown) to be connected thereto for directing air (or creating a vacuum) through the path 270 which is defined through an opening in an interior wall 272 into an annular space 260 between the inner and outer tip housings 210, 214. The air then passes out the distal tip opening 222 of the outer tip housing 214 and into another annular space 274 defined between the inner tip housing 210 and the interior of the safety speculum 226. The directed air exits through the distal tip opening 228 of the safety speculum 226. A rear wall 278 seals the assembly, along with the mounted safety speculum 226 from air leakage other than through the distal tip opening 228, as shown in FIG. 4(d).

The safety speculum 226 is releasably attached to the outer tip housing 214 using a bayonet attachment as described in commonly owned U.S. Pat. No. 4,380,998 issued to Kieffer, et al, the entire contents of which are herein incorporated by reference. In use, the otoscopic instrument head 48 is attached as previously described and as shown in FIG. 3(a). The described latching mechanism allows the instrument head 48 to be locked into engagement with the front side 44 of the instrument body 42.

Referring to FIG. 4(a), this engagement allows the proper electrical interconnection to power the lamp assembly 101 which directs light through the optical fiber bundle 262 to the distal tip opening of the insertion portion 206. In addition, insufflation capability is provided through the port 250 to allow stimulation of the tympanic membrane.

The target of interest (the interior of the ear canal) is viewed by the objective lens assembly 234 through the aligned tip opening 226, 218 which then projects the optical image along the viewing axis 85, FIG. 3(a), focusing the image onto the electronic sensor 82, FIG. 3(a). Though described as an otoscope embodiment, it is conceivable that an instrument head of the above or similar design could be used in cavities having narrow or shaped openings in-addition to the ear canal.

SURFACE MICROSCOPE HEAD

Figure 5A:
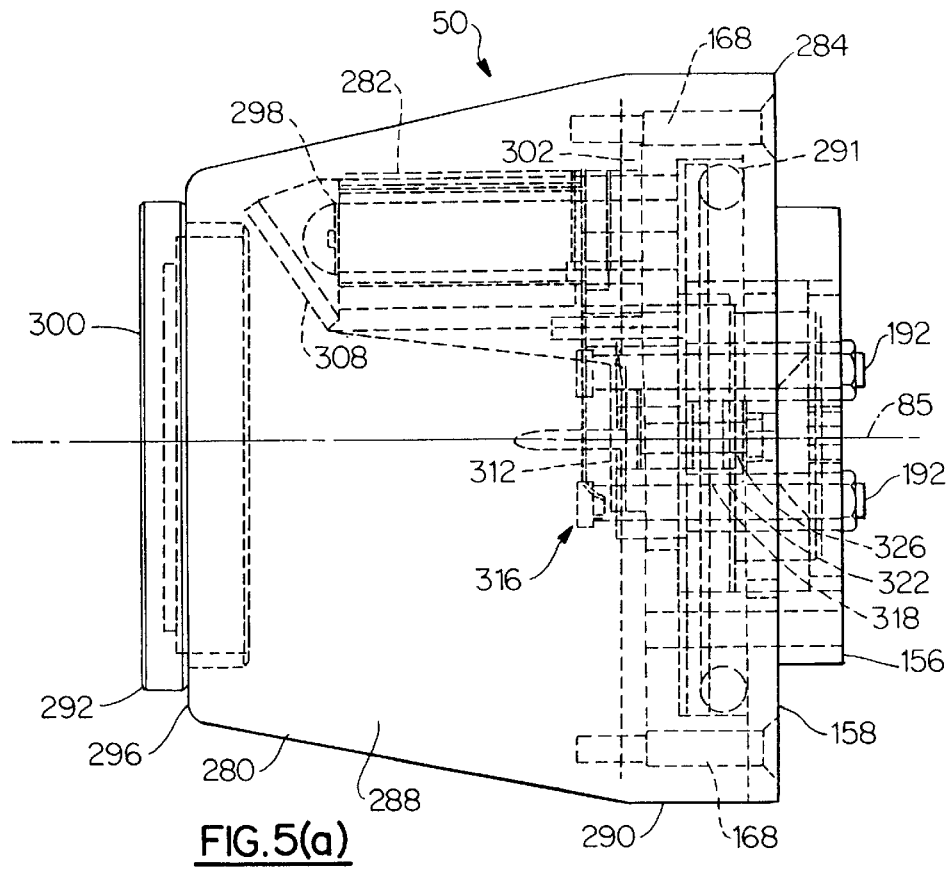
FIG. 5(a) is a cross-sectional view of a surface microscope head used with the instrument body of FIG. 3(a)
Figure 5B:
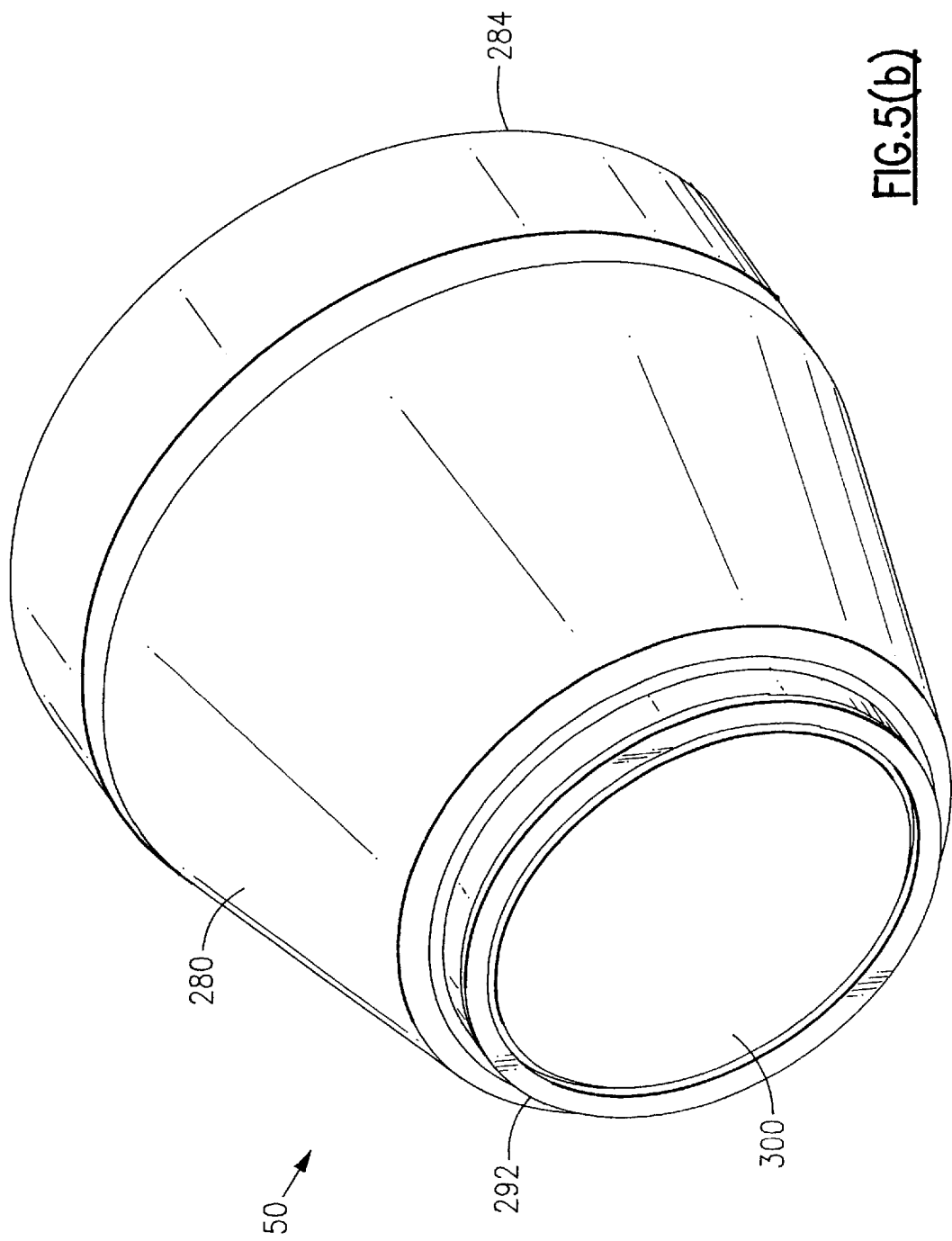
FIG. 5(b) is a front perspective view of the surface microscope head of FIG. 5(a)
Figure 5C:
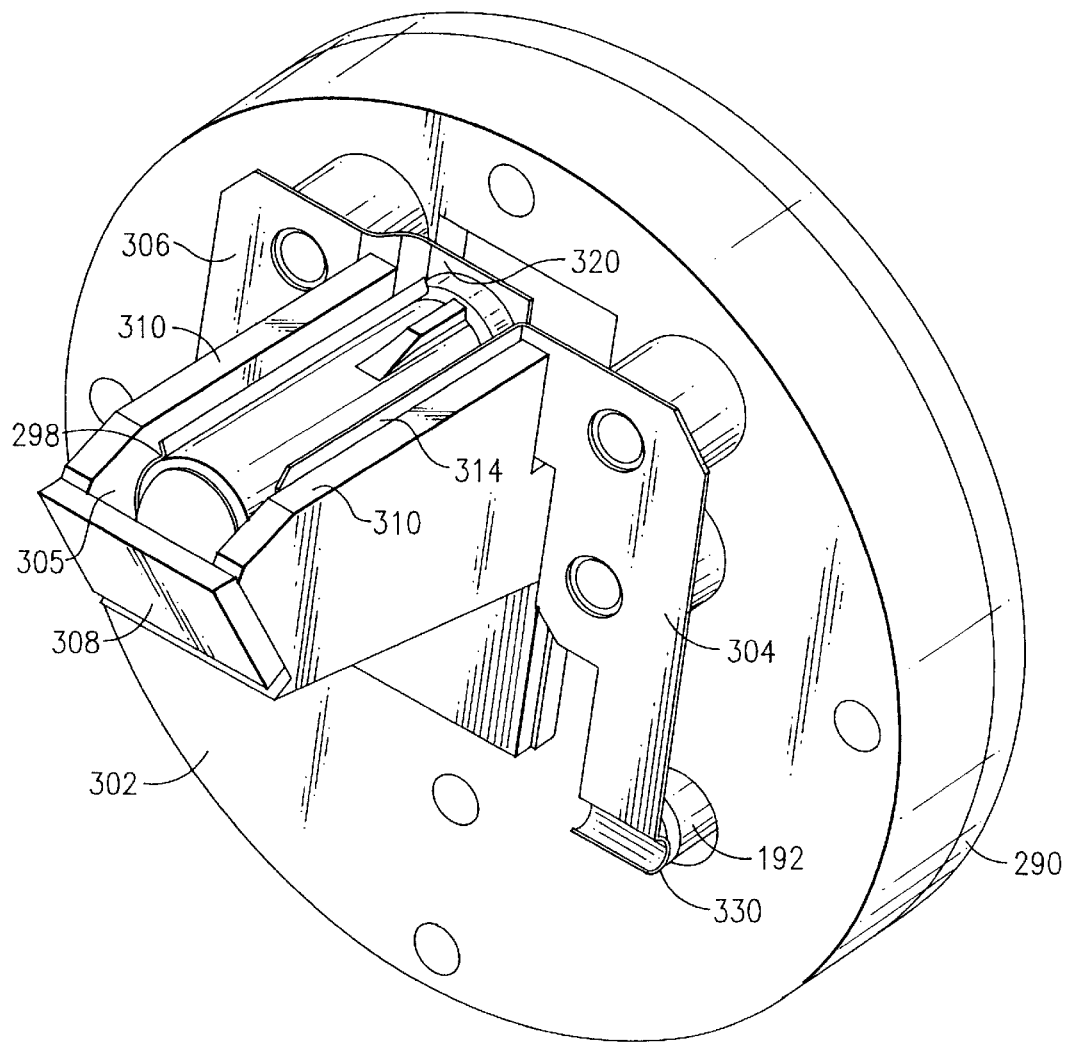
FIG. 5(c) is a partial front perspective view of the surface microscope head of FIGS. 5(a) and 5(b), illustrating the interconnection between the electrical contacts of a retained lamp assembly and the latching mechanism.

Referring to FIGS. 5(a)–5(c), a surface microscope head 50 according to the instant embodiment includes an elongated housing 280 having a hollow interior 288 and respective proximal and distal ends 284, 296. The housing 280 has a substantially frusto-conical configuration with the proximal end 284 being wider than the distal end 296 to provide adequate space allocation for an illumination assembly 282 disposed therein.

The proximal end 284 of the instrument head 50 is defined by a cylindrical base portion 290 having a cavity 291 sized for retaining a shoulder portion 177 of a latching member 156. The cavity 291 is formed between a flat ring 158 mounted by threaded fasteners (not shown) through countersunk holes 168 to an interior wall 302. The remainder of the latching member 156 extends through an opening 164, FIG. 4(b), on the flat ring 158, and is biased into a first axial position by a pair of leaf springs 304, 306 mounted to the inside surface of the interior wall 302 and engaged into biasing contact with a pair of contact members 192, only one being shown in FIG. 5(c), extending through the latching member 156 and the interior wall 302 into the hollow interior 288 of the housing 280. For purposes of discussion, the latching member 156 is identical to that previously described which releasably engages the front face 44, FIG. 3(a), of the instrument body 42, FIG. 3(a). Therefore, no further discussion is required except as needed.

A releasably attachable lens holder 292 is disposed at the distal end 296 thereof The lens holder 292 accommodates a viewing window 300 having a measuring reticle (not shown) for providing a frame of reference or means of measuring a target of interest. For purposes of this embodiment, the viewing window 300 provides a field of view of approximately 15 mm, and is releasably attachable to allow cleaning and/or sterilization. The viewing window 300 according to this embodiment is made from a plate glass, though any optical grade material including light plastics such as acrylic, or polycarbonate are suitable.

As most clearly seen in FIGS. 5(a) and 5(c), the illumination assembly 282 includes a light source, such as a miniature halogen lamp 298, which is retained within a spaced enclosure 305 formed by a pair of parallel supporting plates 310 extending from the interior of the wall 302. As with the other illumination assemblies described herein, other suitable light sources, such as low-power surface-mounted or bulb-type white LEDs, can also be substituted. The spaced enclosure 305 further includes a spring metal receptacle 314 into which the lamp 298 is press-fitted, the receptacle being formed from one of a pair of leaf springs 304 having a substantially flat portion attached to the interior of the wall 302. The remaining leaf spring 306 includes a flat extending portion 320 for contacting the rear electrical contacts (not shown) of the halogen lamp 298 when fitted into the spaced enclosure 305. A first polarizer 308 is provided at the light emitting end of the lamp 298 and attached to the corresponding end of the supporting plates 310. The first polarizer 308 is angled relative to the axis formed between the viewing window 300 and a lens assembly 316 including a plano lens 318, an aperture plate 322, and an objective lens 326 respectively disposed within the interior of the base portion 290. According to this embodiment, a second polarizer 312 is also provided between the viewing window 300 and the lens assembly 316, to assist in minimizing glare presented by the illumination assembly 282. The polarizer 308, 312 also combine to minimize specular glare from the target (e.g. skin) surface.

In use, the instrument head 50 is mounted in the previously described manner such that the latching member 156 inwardly deflects when engaged with the front face 44, FIG. 3(a), of the instrument body 42. This deflection causes the cylindrical contact members 192 to bear against respective engagement portions 330 of the leaf springs 304, 306, as illustrated in FIGS. 5(a) and 5(c). Subsequent twisting of the instrument head 50 as described above, also aligns the contacts 192 with the corresponding contacts 140, FIG. 3(b), provided in the instrument body 42, FIG. 3(b), and completes an electrical connection causing the lamp 298 to illuminate upon locking of the instrument head 50 in place.

The illumination assembly 282, and particularly the first polarizer lens 308, being angled relative to the viewing axis 85 causes light to indirectly strike the viewing window 300 in order to minimize reflective glare from the inside surface thereof, and to prevent an image of the illuminating assembly to be reflected optically through the lens assembly 316. When assembled, the lens assembly 316, including the second polarizer 312, and the viewing window 300 are each aligned along the viewing axis 85, FIG. 3(a), to allow a focused optical image to be transmitted to the electronic sensor 82, FIG. 3(a). The lens assembly 316 allows focusing of an optical image of the target (a wart, lesion, or other skin disorder) when the viewing window 300 is placed in direct contact therewith.

The preceding embodiment relates specifically to skin-surface examinations. It will be readily apparent, however, to one of sufficient skill in the field, that other non-medical applications requiring similar analysis can utilize instruments suitably configured.

GENERAL VIEWING INSTRUMENT HEAD

Figure 6A:
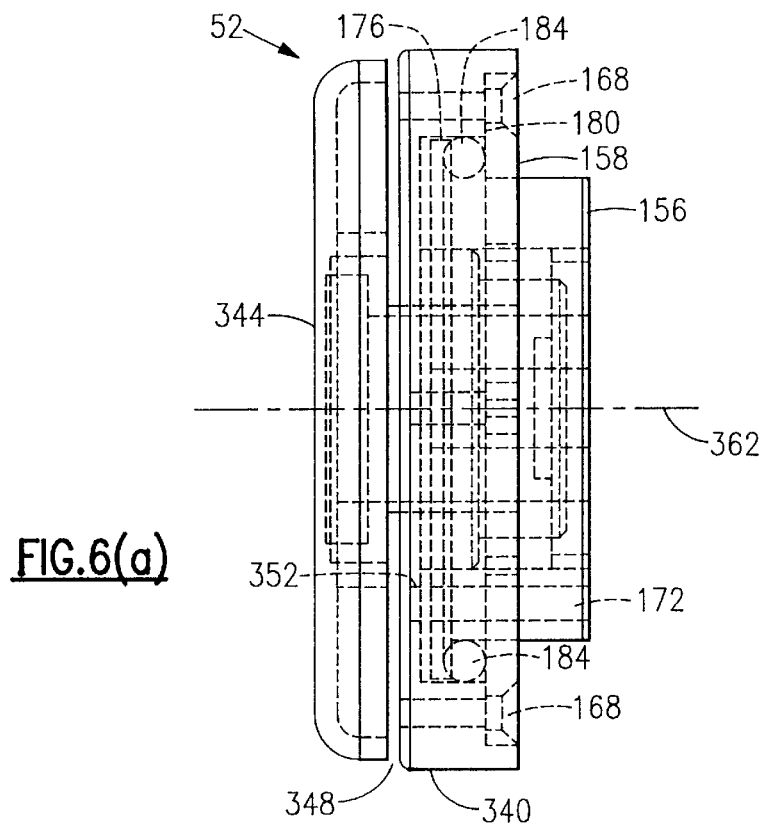
FIG. 6(a) is a side-sectional view of a general-viewing instrument head interchangeably used with the instrument body of FIG. 3(a)
Figure 6B:
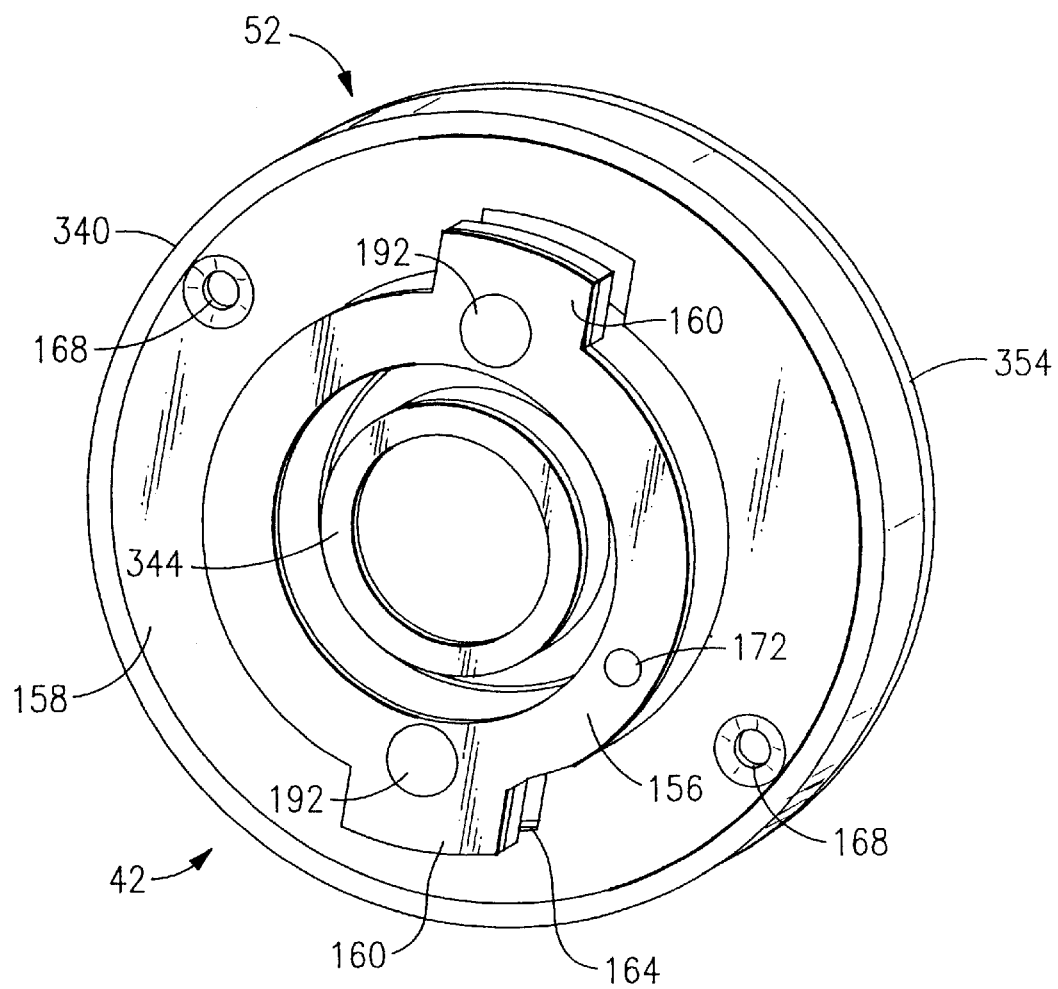
FIG. 6(b) is a partial rear perspective view of the general-viewing instrument head of FIG. 6(a)
Figure 6C:
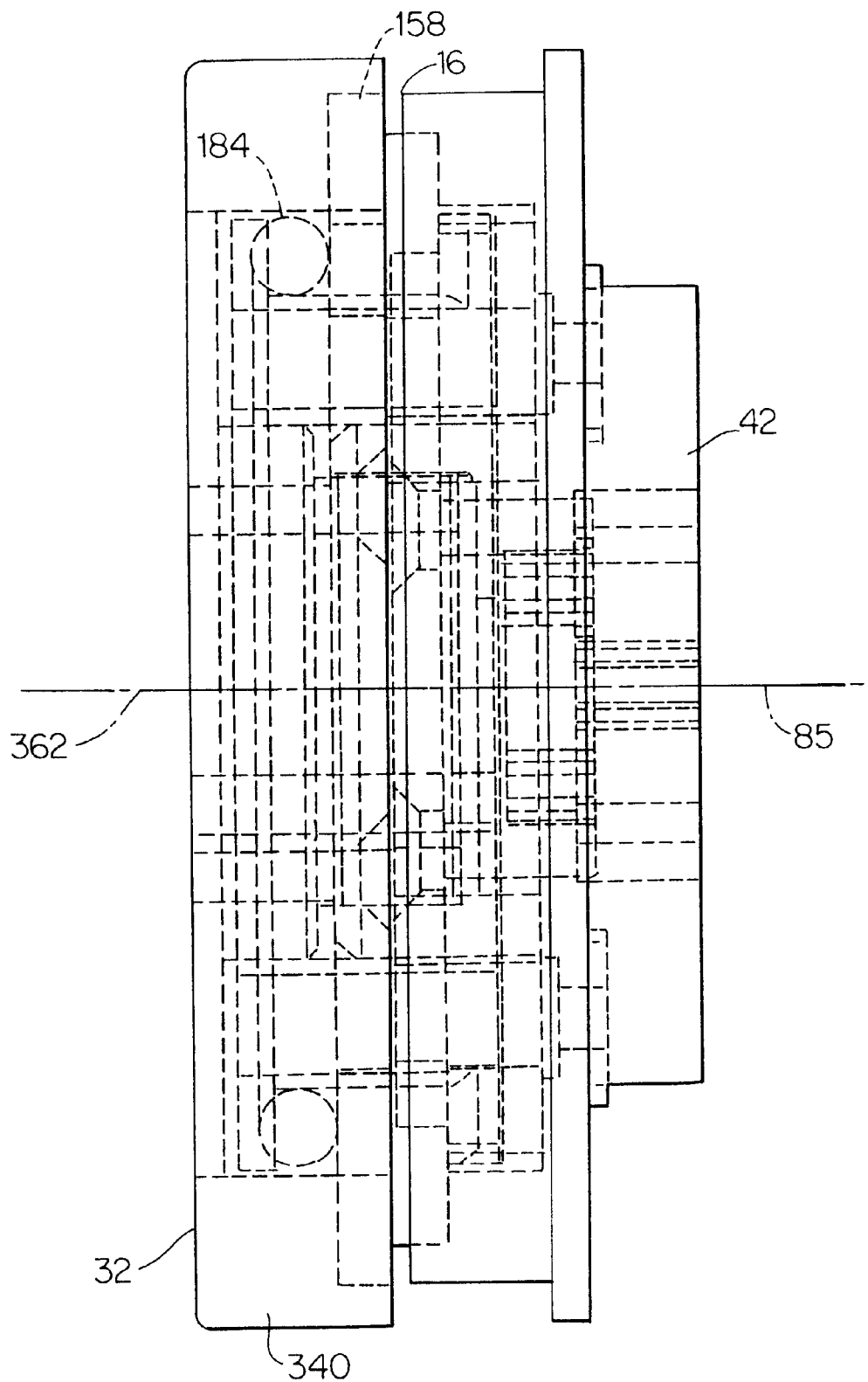
FIG. 6(c) is a partial side sectional view of the latching mechanism of the general-viewing instrument head of FIGS. 6(a) and 6(b), as engaged with the instrument body of FIGS. 3(a) and 3(b)

Referring now to FIGS. 6(a)–6(c), the general viewing instrument head 52 according to the present embodiment includes a cylindrical base section 340 similar in construction to the dermatological instrument head 50 previously described. An adjustable lens assembly 344 is securely mounted within a lens holder 354 which is threaded or otherwise attached through an opening 352 provided in a distal end 348 thereof. The adjustable lens assembly 344 includes at least one objective lens (not shown) and an aperture plate (not shown), wherein the objective lens has sufficient power to provide an enhanced field of view. The lens assembly 344 is movable along a defined axis 362 and allows an optical image to be focused onto the electronic sensor 82, FIG. 3(a). The optical axis 362 is aligned with viewing axis 85, as shown in FIG. 6(c).

The instant instrument head 52 includes a latching member 156 as previously described for releasably engaging the front face 44, FIG. 2, of the instrument body 42, as shown in FIG. 6(b). Because an illumination assembly is not present, however, the described instrument head can have a compact construction.

MAGNIFYING INSTRUMENT HEAD

Figure 7A:
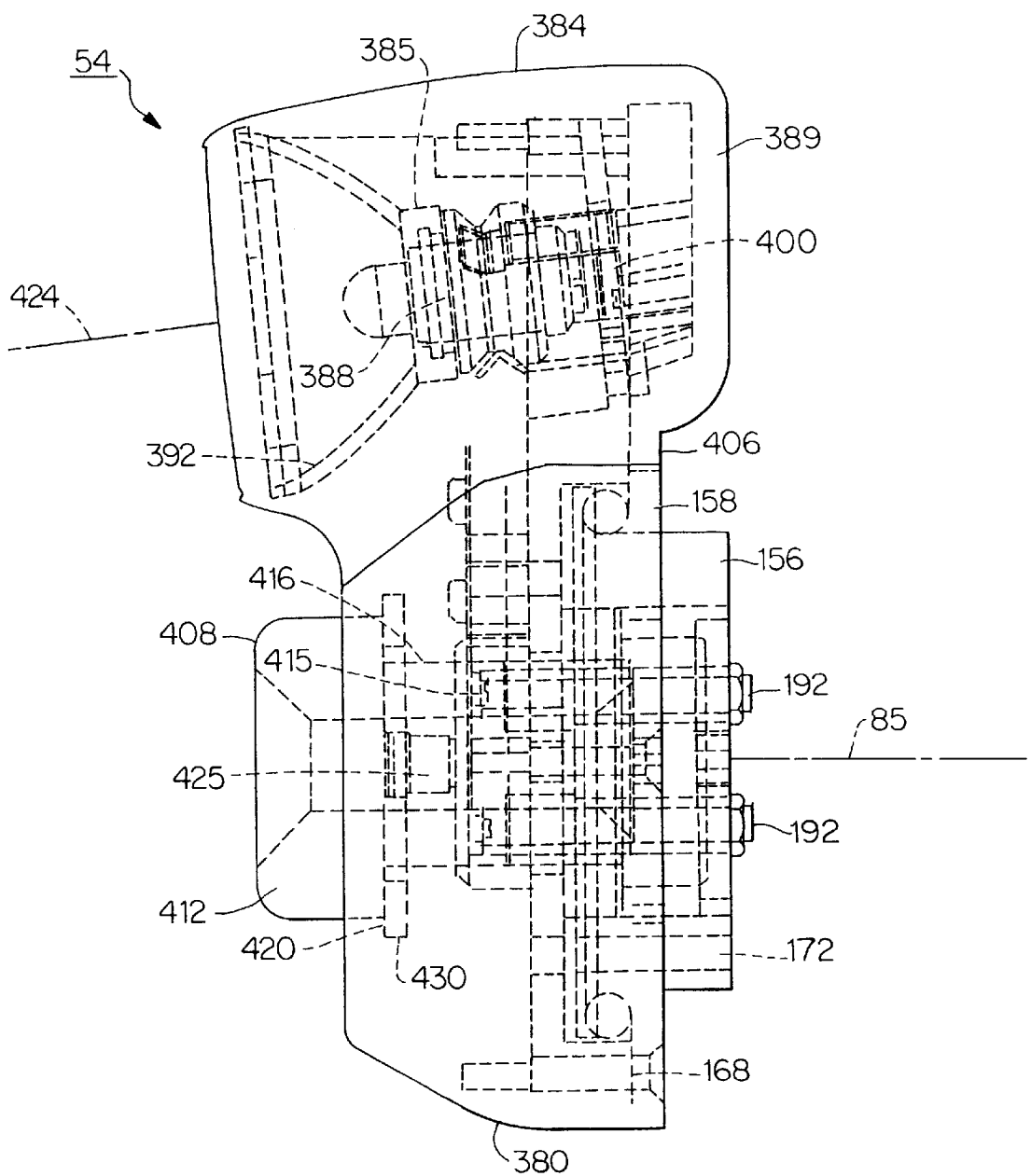
FIG. 7(a) is a side-sectional view of a magnifying instrument head interchangeably used with the instrument head of FIG. 3(a)
Figure 7B:
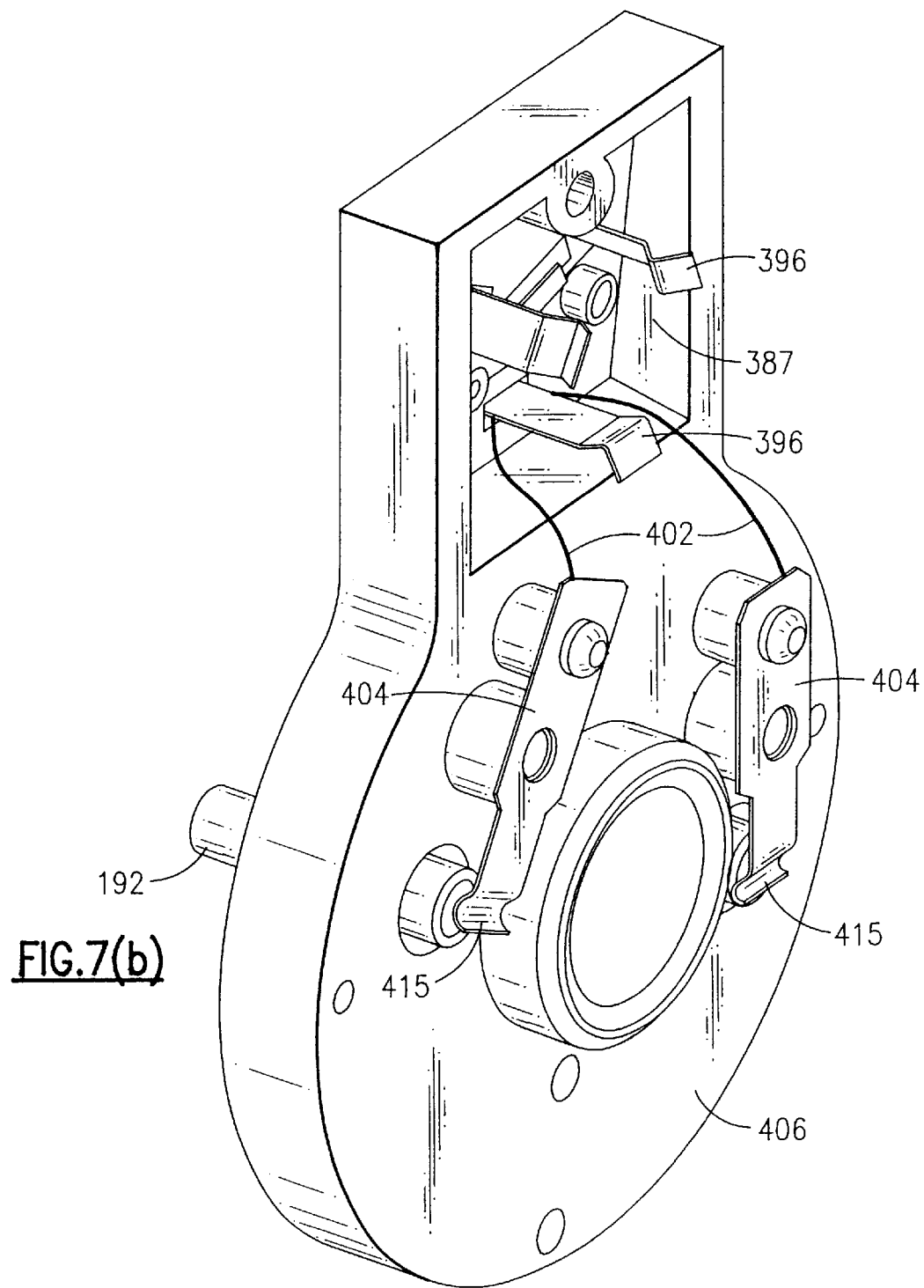
FIG. 7(b) is a partial front perspective view of the magnifying instrument head of FIG. 7(a), illustrating the interconnection between the latching mechanism and the lamp electrical contacts.
Figure 7C:
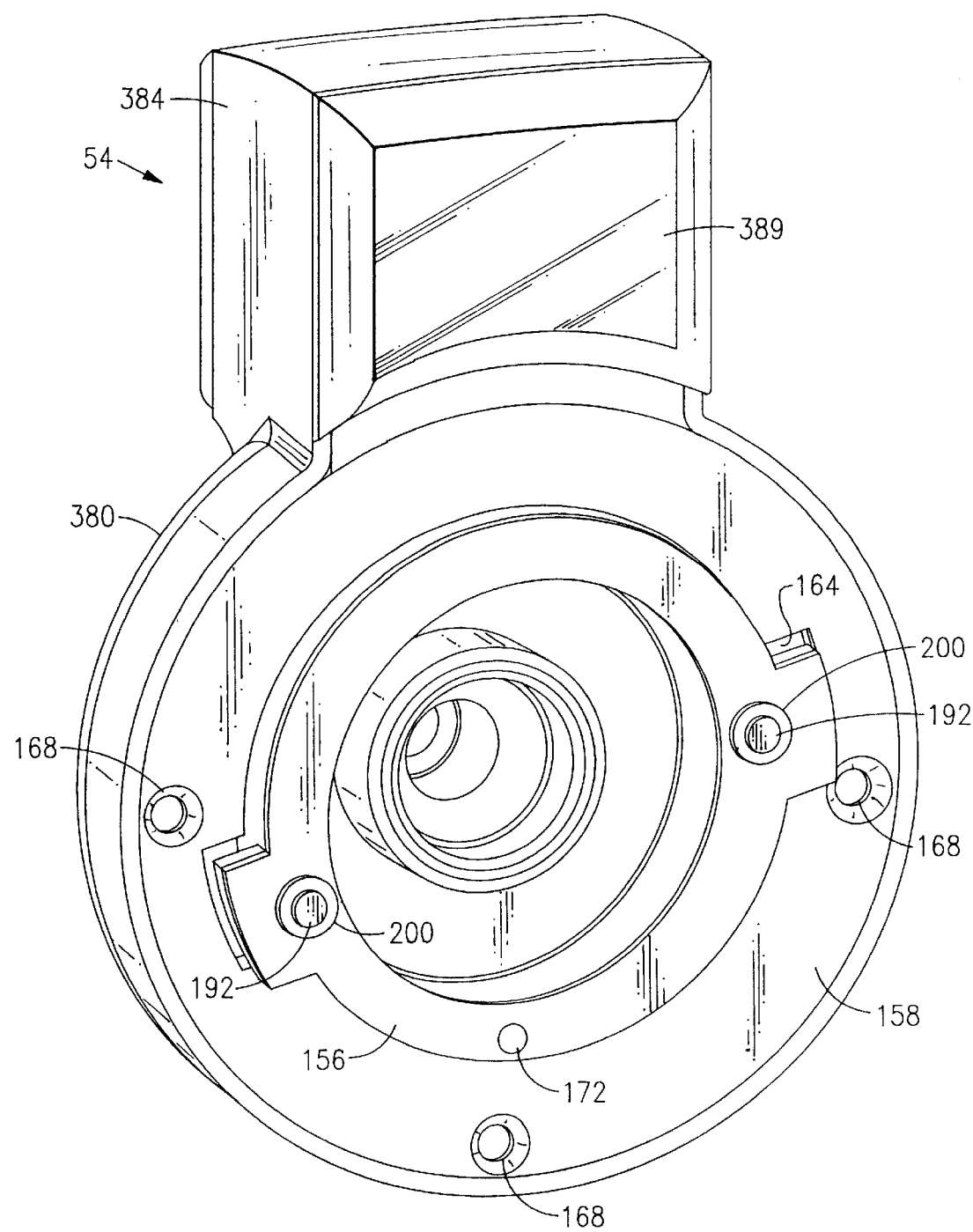
FIG. 7(c) is a rear perspective view of the magnifying instrument head of FIGS. 7(a) and 7(b)

Referring to FIGS. 7(a)–7(c), the magnifying instrument head 54 is defined by a cylindrical housing 380 including an integral depending portion 384 used to retain an illumination assembly 385. The illumination assembly 385 includes a halogen lamp 388, or as noted above, another suitable light source, and a reflector 392 which are retained within a pocket 387 formed by a triad of spring fingers 396 extending from a rear wall 389, as most clearly shown in FIG. 7(b).

The halogen lamp 388 includes a rear electrical contact 400 which engages a sheet metal plate (not shown) when the lamp is press-fitted into the spring fingers 396. A set of wires 402 extend from the metal plate and the spring fingers 396 to respective leaf springs 404 mounted at one end to a rear interior wall 406 of the housing 380. The remaining end 415 of the leaf springs 404 is cantilevered for movement and is aligned with the ends of cylindrical contact members 192 passing through the latching member 156 and the rear interior wall 406. For purposes of this embodiment, the latching member 156 is identical to that described above. To avoid redundancy, a recitation of these features, shown in FIGS. 7(a)–7(c), is not repeated. Therefore, when the latching member 156 is engaged, the electrical connection is completed and the lamp 388 is illuminated.

The housing 380 also includes an adjustable lens assembly 408 defined by a mushroom-shaped housing 412 having a necked portion 416 which is fitted into an opening 420 in the front side of the housing. At least one objective lens assembly 425 and an adjacent aperture plate (not shown) are contained therein. The lens assembly 408, according to this embodiment, is received within the opening 420 and is rotatably and axially movable therein to permit focal adjustment. A shoulder portion 430 having a width dimension which is wider than the opening in the front side of the housing 380 provides an adjustment limit.

In use, and when the instrument head 54 is assembled to the front side 44, FIG. 3(b), of the instrument body 42, FIG. 3(a), in the manner previously described above, an image perceived by the optics contained in the adjustable lens assembly 408 is transmitted along the viewing axis 85, FIG. 3(a), to the electronic sensor 82.

As noted, the depending portion 384 of the housing 380 is built in two pieces. Removal of the rear wall 389 allows the lamp 388 to be removed for replacement as needed. Finally, the lamp 388 is oriented such that the defined illumination axis 424 is angled relative to the viewing axis 85.

A second embodiment of a video diagnostic instrument system according to the present invention is herein described with reference to FIGS. 8–10(b). Similar parts are herein labeled with the same reference numerals for the sake of convenience.

Figure 8:
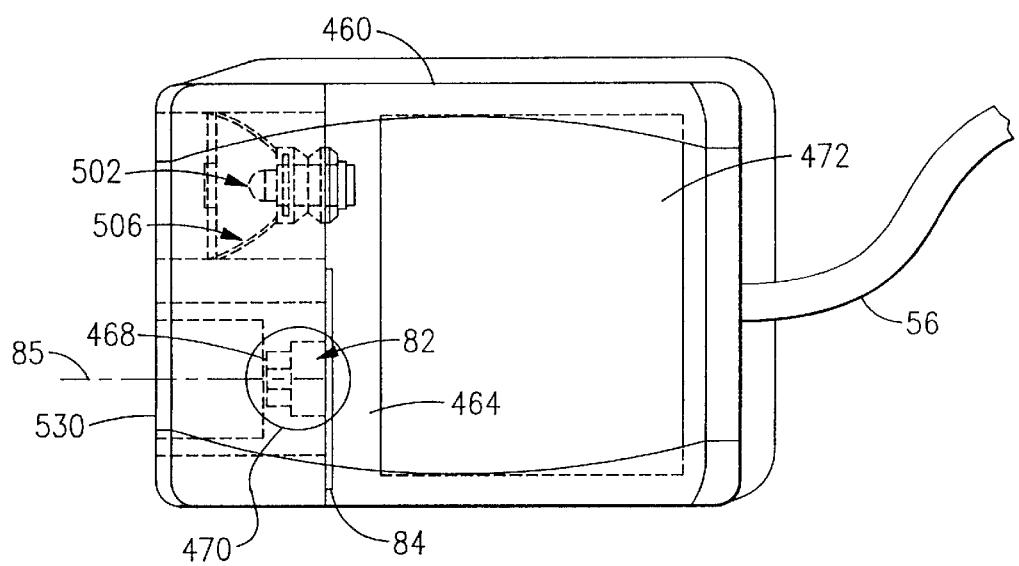
FIG. 8 is a partial side sectional view of an instrument body according to a second preferred embodiment of the present invention.

As shown in the cross-sectional view of FIG. 8, an instrument base unit 460 is illustrated having a hollow interior 464 and within which an imaging assembly 470 and an illumination assembly 498 are each provided. The imaging assembly 470, as in the preceding embodiment, includes a CCD or other electronic sensor 82 having an image plane or substrate 84 which is aligned with a viewing opening 468 of the base unit 460, thereby defining a viewing axis 85. A video processing board 472 having circuitry for converting an electronic signal from the electronic sensor 82 to a monitor-ready video signal is also disposed within the interior 464 of the base unit 460 and is interconnected by transmission lines (not shown) through an umbilical cable 56 partially shown). The illumination assembly 498 includes a halogen lamp 502 positioned within a reflector 506, the lamp having electrical contacts (not shown) which are interconnected to the transmission in the umbilical cable 56.

As in the preceding embodiment, a plurality of instrument heads (not shown) can be releasably mounted to the front face of the instrument base unit 460, in a manner similar to that described above. For purposes of the present embodiment, an exemplary instrument head is shown in FIG. 9, which is a surface microscope head 520 similar to that described as 50 above, having a housing 522, including an engagement or locking member 524 projecting from the rear side 528 for attachment within a defined cavity 530 of the distal face of the instrument base unit 460.

The instrument head housing 522 includes a viewing window 526 mounted in a releasably attachable circular lens holder 527 which is mounted on the distal end 532 of the housing oppositely disposed from the locking member 524.

The housing 522 further includes an expanded interior 533 sized for retaining a light pipe 534 for transmitting light from the illumination assembly 498 to the viewing window 526.

Referring to FIGS. 9, 10(a) and 10(b), the light pipe 534 is made from a transparent (light-transmissive) material, such as acrylic or polycarbonate, including a light receiving end 542 which is positioned in alignment with the light emitting end 500 of the illumination assembly 498, which as noted earlier, is disposed above the imaging assembly 470. The light receiving end 542 is part of a cylindrical light emitting portion 538 which is curved to allow the light pipe 534 to extend into the expanded portion of the interior 533. The pipe 534 includes a cylindrical light emitting portion 538 at the remaining end having a through opening 546 to enable an optical image from the viewing window 526 to be transmitted along the viewing axis 85 without interference. In the meantime, light from the illumination assembly 498 is transmitted through the length of the light pipe 534 where the light is transmitted in a circular area through the viewing window 526 from the cylindrical light emitting portion 538.

Figure 11:
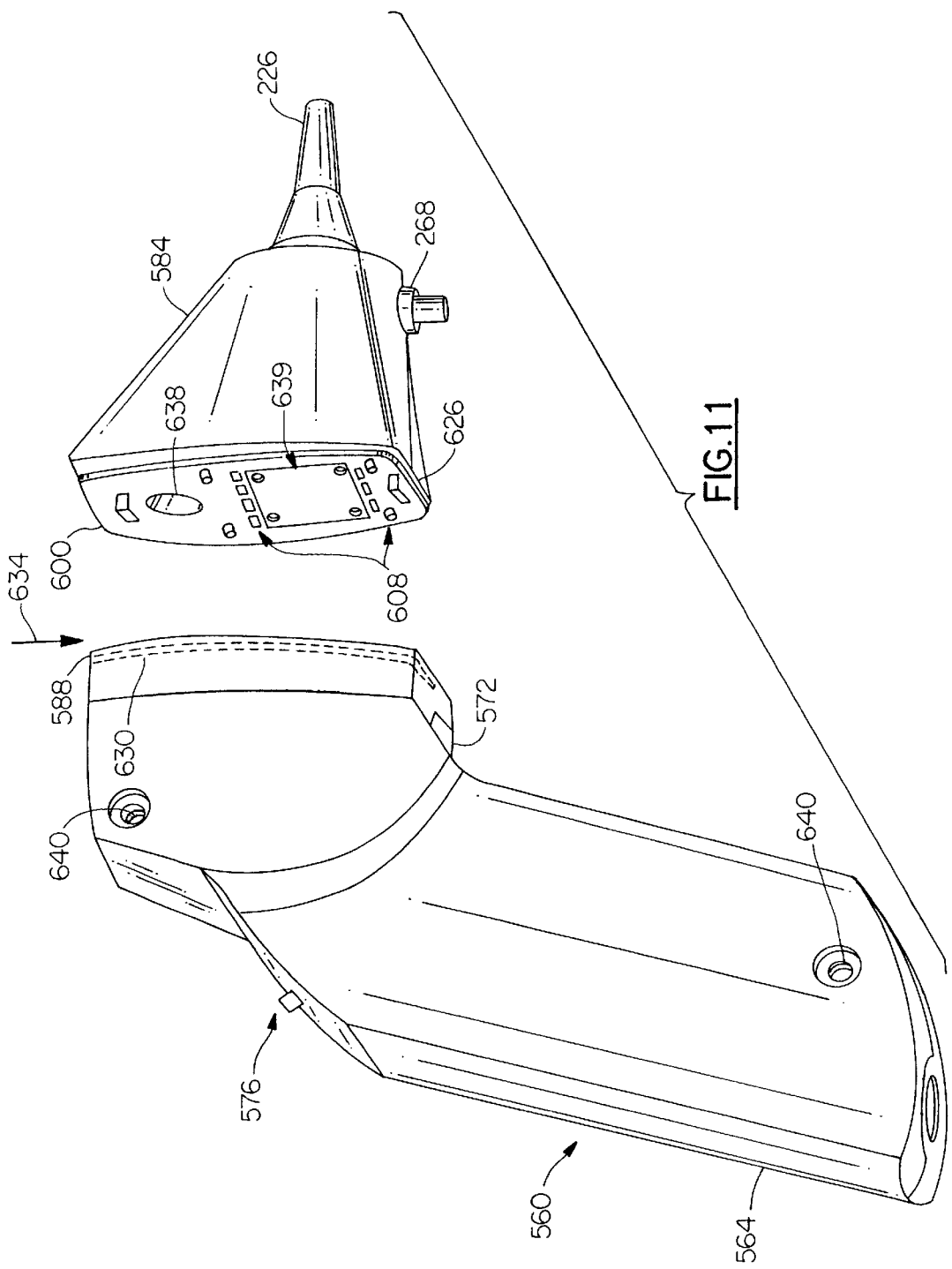
FIG. 11 is a partial side assembly view of an imaging instrument system according to a third embodiment of the present invention.
Figure 12:
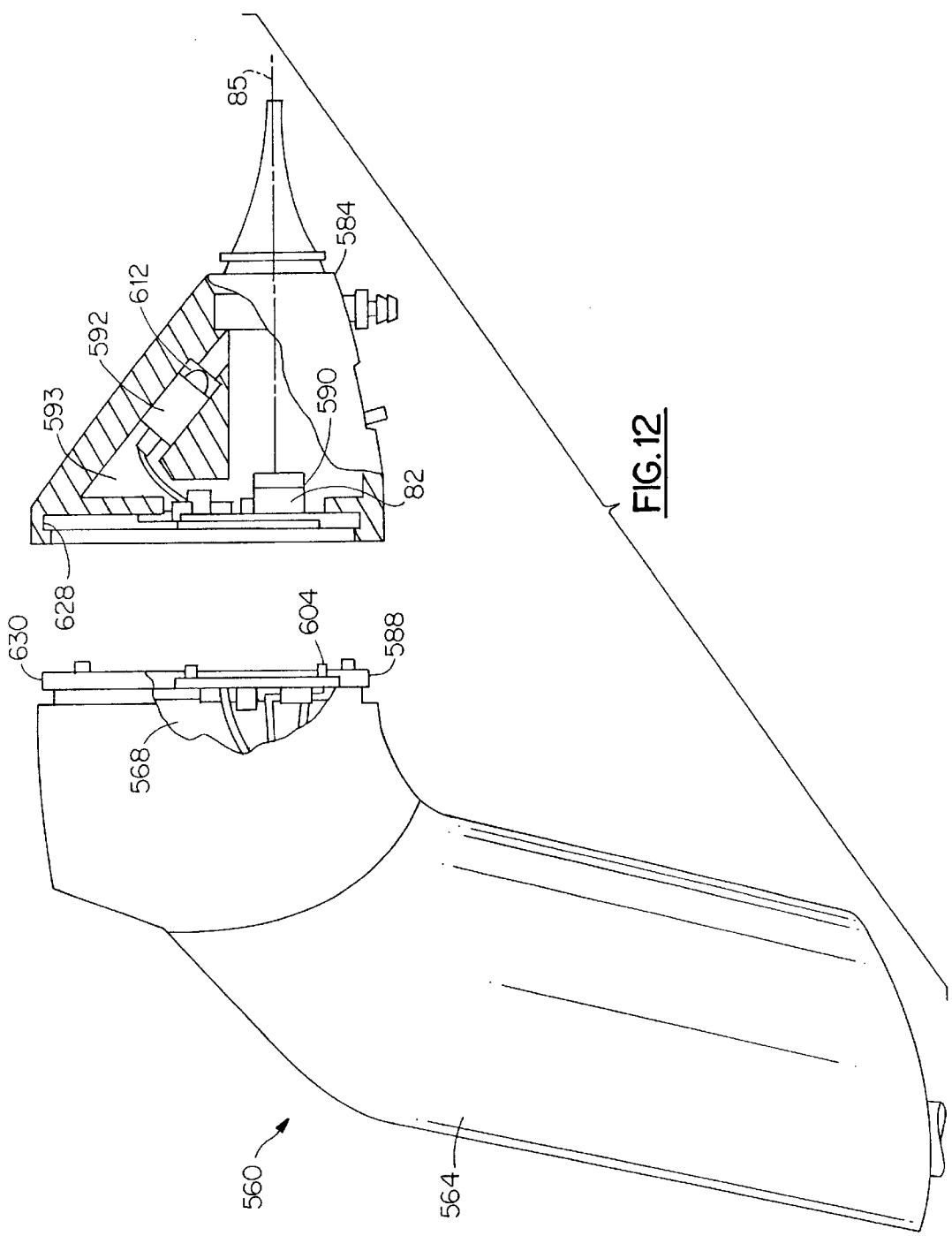
FIG. 12 is a side sectional view of the assembled imaging instrument of FIG. 11.

The location of the electronic imager 82 in the described system is not limited to the interior of the instrument body. Referring to FIGS. 11 and 12, a diagnostic instrument system in accordance with a third embodiment of the present invention is herein described.

An instrument body 560 includes a hand-holdable portion 564 shaped similarly like a pistol grip which includes a hollow interior 568 sized to retain a number of components. Preferably, the body 560 is a two-part housing connected by fasteners inserted through spaced holes 640. A number of depressible buttons and/or switches (not shown) are included on the exterior of the body 560 to control a number of functions including an ON/OFF power switch 572, a white balance switch 576, and an electronic zoom control switch (not shown).

At least one instrument head 584 is mountable to the front face 588 of the instrument body 560, the instrument head including an electronic imager assembly 590 and an illumination assembly 592 disposed within a substantially hollow interior 593. The imager assembly 590 includes an electronic sensor 82 disposed adjacent to a rear wall 600 and includes a number of spring-loaded contacts 608 on the exterior of the rear wall 600, which can be subsequently brought into engagement with corresponding contacts 604 provided on the front face surface 588 of the instrument body 560.

The illumination assembly 592 includes a halogen lamp 612 positioned above the imager assembly. An opening 638 in the rear wall 600 allows the lamp to be accessed for replacement, while the imager assembly 590 is accessible by means of a removable cover 639.

The engagement interface between the instrument head 584 and the instrument body 560 is structurally different than the latching mechanisms previously described. In this embodiment, the rear wall 600 of the instrument head 584 includes a peripheral slot 628 covering at least three sides of the periphery for engaging a correspondingly sized annular shoulder 630 provided in the front face 588 of the instrument body 560.

The instrument head 588 is fitted by sliding the head onto the body 560 in the direction of arrow 634, as shown in FIG. 11.

Figure 13:
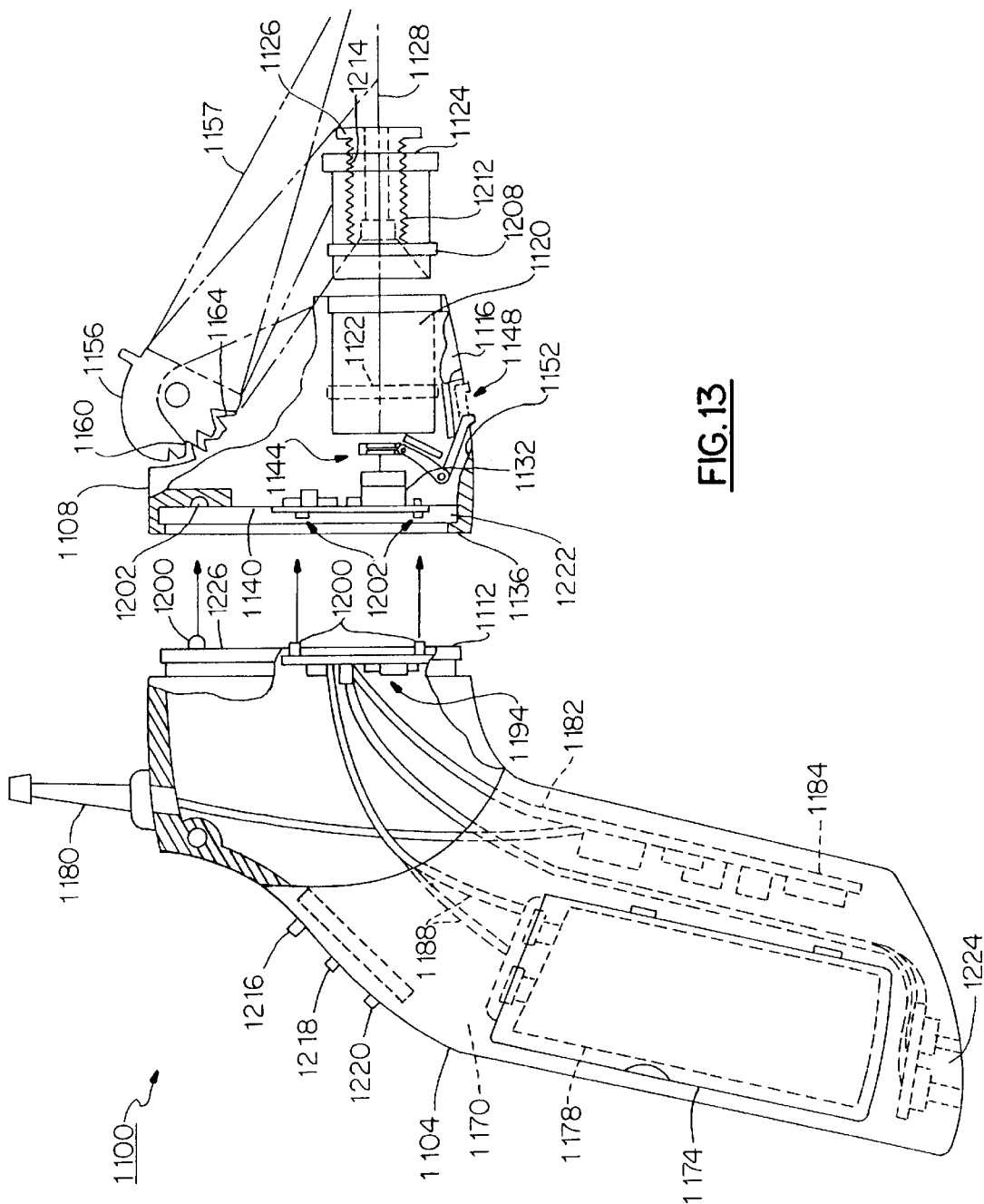
FIG. 13 is a side sectional view of a video instrument according to a fourth embodiment of the present invention.

Referring to the sectional view of FIG. 13, there is shown a diagnostic or other suitable instrument 1100 according to a fourth embodiment of the present invention. The instrument 1100 includes a body section 1104 and an instrument head 1108 which is releasably attachable to a distal face 1112 thereof.

The instrument head 1108 according to the present embodiment includes a housing 1116 having a distal receptacle 1120 sized for accommodating a lens assembly 1124 having a series of linearly arranged optical elements disposed along an optical axis 1128 in an adjustable lens cell 1126.

An electronic imager 1132, such as a miniature CCD or CMOS vide camera, is attached to an interior surface 1140 of a rear wall 1136 of the instrument head 1108. The imager 1132 includes a light receiving surface (not shown) which is aligned with the optical axis 1128 to receive any focused image of a target of interest from the adjustable lens cell 1126.

A polarizer element 1 144 is disposed between the electronic imager 1132 and the receptacle 1120. The polarizer element 1144 is preferably attached to a slide mechanism 1148 externally connected to the housing 1116 through a slot 1152, allowing selective positioning of the polarizer element relative to the optical axis 1128.

An adjustable lamp assembly 1156 includes a low-power miniature halogen lamp or other suitable light source to an external portion of the instrument head housing 1116. According to the present embodiment, the lamp assembly 1156 is pivotally attached to the housing 1116, the housing having a series of circumferentially disposed detents 1160 for accommodating toothed sections 1164 of the lamp assembly 1156 so as to orient the lamp until the illumination axis 1157 is aligned with and intersects the optical axis 1128. Other suitable automatic or manual assembly mechanisms (not shown) for rotating or otherwise shifting the location of the lamp assembly 1156 can easily be imagined.

The body section 1104 of the instrument 1100 includes a handle configuration having an interior sized for accommodating a number of components. The interior 1170 includes a battery compartment 1174 for at least one contained rechargeable battery 1178.

An RF (radio frequency) antenna 1180 is attached by conventional means and extends from an upper part of the body section 1104. Electrical connectors 1182 extending from the RF antenna 1180 are connected to a conventional RF circuit board 1184. Another set of electrical connectors 1188 extend from opposite sides of the battery compartment 1174 in alignment with the terminals of the battery 1178 to a power modifying printed circuit board 1194 disposed adjacent the distal face 1112 of the instrument head and having appropriate regulators and drivers for setting the voltage and wattage for powering the imager 1132 and the adjustable lamp assembly 1156 of the instrument head 1108.

A series of spring loaded contacts 1200 extend from the front of the power modifying printed circuit board 1194 for engaging female contacts 1202 located on the exterior side of the rear wall 1136 of the instrument head 1108.

The circuit board 1194 is interconnected by known means to a set of switches located on the exterior of the body section 1104 of the instrument 1100. More particularly, these switches include an ON/OFF power switch 1216, an electronic zoom switch 1218, and a white balance switch 1220, wherein the power modifying circuit board 1194 is connected in a known manner order to support the above switches.

As noted, the lens cell 1126 is adjustable via a threaded portion 1212 which engages a threaded opening 1214 of the lens assembly 1124. In assembly, the distal receptacle 1120 includes a groove 1122 for accommodating an O-ring 1208 on the lens assembly 1124 used to seal the lens assembly into position.

In operation, engagement of the corresponding contacts 1200, 1202 during attachment of the instrument head 1108 to the distal face 1112 of the body section 1104 powers the adjustable lamp assembly 1156 and the electronic imager 1132 by connection with the power modifying printed circuit board 1194, as powered by the battery 1178.

Selective depression of the power ON/OFF switch 1216 can also be used to control the lamp assembly 1156 and imager 1132 after the instrument head 1108 has been attached.

Preferably, and according to this embodiment, the latching mechanism used to retain the instrument head 1108 is similar to that described in FIG. 12 in which the rear wall 1136 of the instrument head 1108 includes a peripheral slot 1222 for engaging a corresponding annular shoulder 1226 of the distal face 1112 of the body section 1104, though other means could similarly be employed. When engaged, the output of the electronic imager 1132 can be transmitted using the RF circuitry and antenna 1180 to a video processor, video printer or other peripheral device (not shown) having suitable means for receiving and decoding the RF signal and obviating the need for cabling.

A charger port 1224 extends from the bottom of the body section 1104 to allow recharging of the battery 1178 without having to remove the battery from the compartment 1174.

MULTIMEDIA DIAGNOSTIC INSTRUMENT

Figure 14:
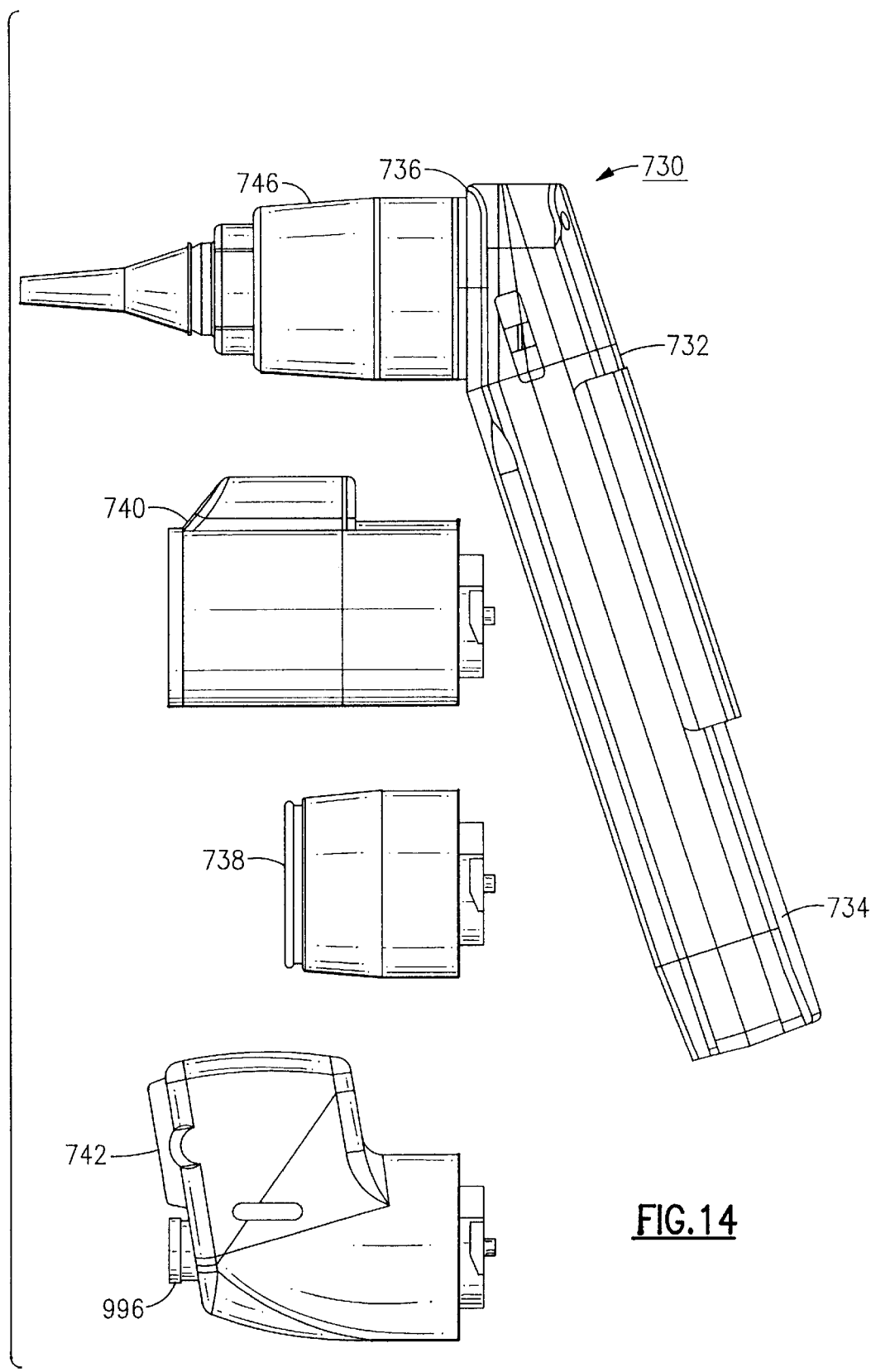
FIG. 14 is a side partial view of a multimedia instrument made in accordance with a preferred embodiment of the present invention.

Referring now to FIG. 14, a diagnostic instrument system 730 according to a further preferred embodiment of the present invention comprises a compact diagnostic instrument 732 including a housing or body 734 having a front interface 736 with means for allowing selective releasable attachment thereto of a plurality of instrument heads. According to this embodiment, the instrument heads include a general purpose instrument head 738, a dermatological instrument head 740, a high magnification instrument head 742, and an otological instrument head 746. Other instrument heads such for ophthalmoscopes employing optical systems such as described in commonly assigned U.S. Pat. Nos. 4,526,449 and 4,998,818, for example, incorporated by reference herein, can also be utilized. Details relating to each of the instrument heads 738, 740, 742, 746 and the attachment of each to the diagnostic instrument 732 are described in greater detail below. In passing, however, it should be noted that the instrument heads described in the first embodiment could be substituted for those about to be described and vice versa. Still further, other suitable heads for the same or other purposes, e.g. ophthalmoscopic could be envisioned.

Figure 15:
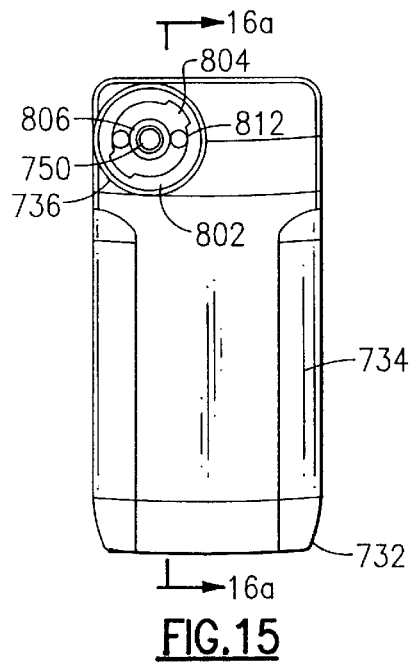
FIG. 15 is a front elevational view of the multimedia instrument of FIG. 14.

Referring to FIGS. 15 and 16, the diagnostic instrument 732 for purposes of the described system 730, FIG. 14, is a compact digital camera having a defined interior 748. The interior 748 is appropriately sized to retain a plurality of components including an electronic imaging element 750, such as a charge coupled device (CCD), disposed adjacent a window 752 or clear covering at the front interface 736. The digital camera used in the described embodiment is a "COOLPIX 300" sold by the Nikon Corporation, though it will be apparent that other known compact digital cameras having similar or other features can be similarly configured for use in the described diagnostic instrument system.

Figure 34:
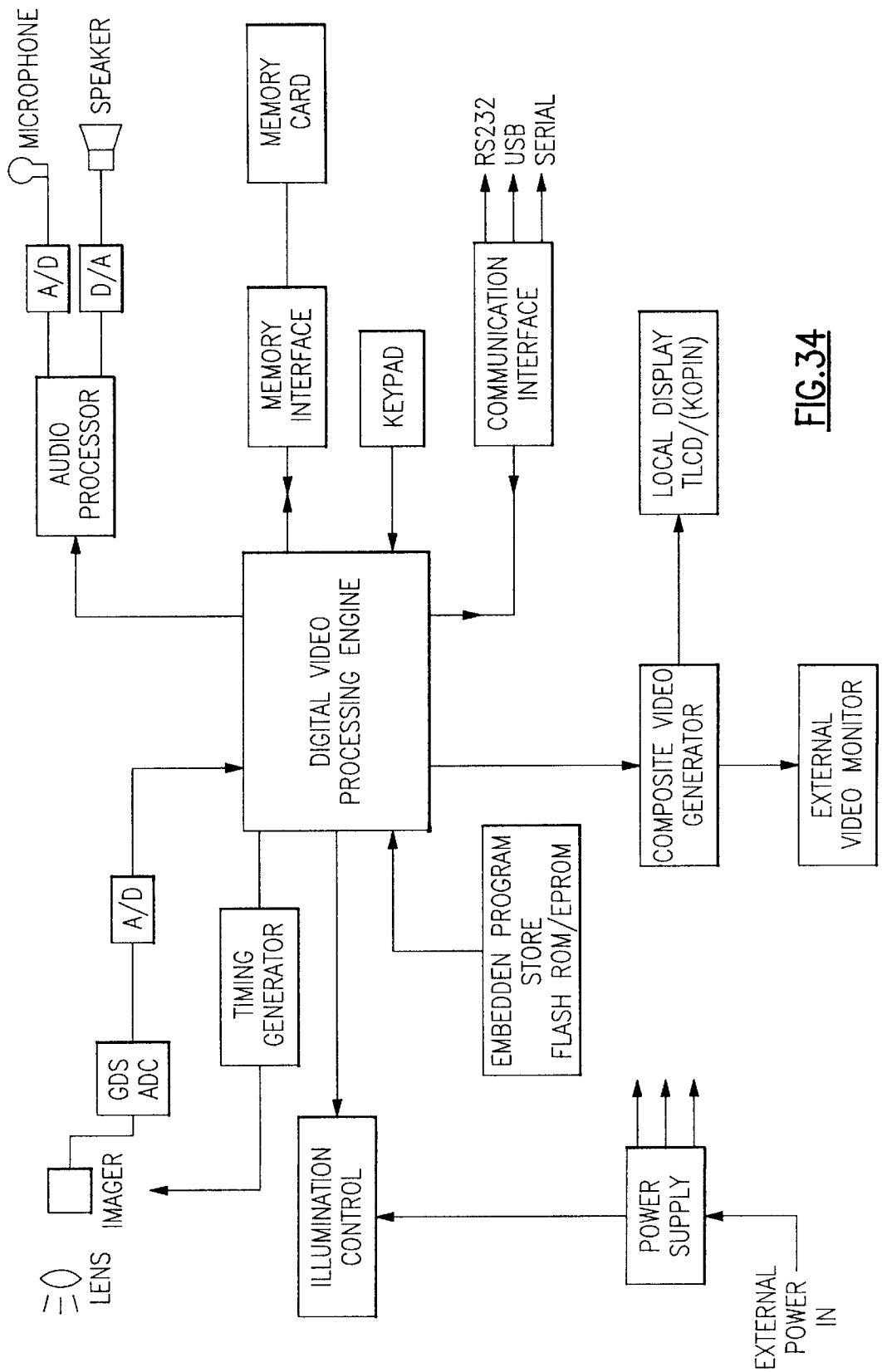
FIG. 34 is a block diagram of a preferred system architecture for a multimedia instrument according to the present invention.

The electronic imaging element 750, as is known to those of skill in the field, includes a light receiving surface having a two dimensional array of pixels (not shown), for receiving an optical image along a viewing axis 753 from a target of interest. Processing electronics (not shown) also retained within the interior 748 allow the optical image to be converted into an electrical signal and subsequently converted into a digital signal. According to the present embodiment, the electronic imaging element 750 is a progressive scanning CCD color camera with a ⅓" 330,000 square-pixel array having a resolution of 640 (horizontal) ×480 (vertical) dots. Other types of imaging elements, such as CMOS imager including those manufactured by Omnivision, Inc., among others, having other processing circuitry (not shown) could alternately be utilized. Reference is made here to FIG. 34 which illustrates an architecture for the described embodiment.

Still referring to FIGS. 15 and 16, a controller, such as a microprocessor with sufficient memory and programmable logic is contained within the interior of the instrument housing 734 and is interconnected to the retained components, including an integral touch-sensitive TFT liquid crystal display (LED) 754, provided at the rear side 756 of the instrument housing 734. Alternately, an eyepiece (Kopin) type of display (not shown) could be used. The processed digital video signal is outputted to the display 754 by the microprocessor for viewing by the user. A protective cover 755, slidingly attached to the rear side 756 of the housing 734 by known means, allows selective access to the display 754. Preferably, the rear side 756 of the instrument housing 764 is angled, as shown in FIG. 15 by reference numeral 760, relative to the vertical axis 762 and orthogonal to the viewing axis 753 of the instrument 732 to facilitate viewing of the display 754 for the user. According to the embodiment, an angle, represented in FIG. 16 as —A—, of approximately 15 degrees is suitable.

Referring to FIGS. 14–18, the programmable logic and internal memory of the microprocessor allows various forms of data to be captured and stored in conjunction with image (video) information. An internal condenser microphone 764 disposed on the top exterior of the instrument housing 734 allows audio information to be captured and stored selectively into the memory of the microcontroller (not shown), while an integral speaker 766 disposed on the rear side 756 of the housing allows playback of the stored audio information in conjunction with a stored video image.

A plurality of control switches located on the exterior of the instrument housing 734 includes a POWER ON/OFF switch 768, as well as a RECORD/PLAYBACK switch 770 controlling the audio recording and playback features of the camera. A series of indicating lamps are also provided, more specifically a power lamp 772, a ready lamp 773, and a recording lamp 774.

The described digital camera used as the diagnostic instrument 732 includes other salient and specific features relating to image capture, such as programmed auto-exposure control, including an electronic single-frame shutter and automatic gain control. The specific teachings of these features do not specifically form a part of the present invention. Therefore, no further discussion is required.

Activation of the diagnostic instrument 732 using POWER ON switch 768 activates the imager and processing circuitry so as to allow a real time video image to be viewed on the TFT display 754. The viewed image can be selectively captured using a shutter release button provided on the instrument housing 734 (not shown), causing the image to be stored into the internal memory of the controller. Activation of the switch 770 allows the microphone 764 to be enabled to allow audio data to be captured corresponding to the video image which is being currently displayed. The camera includes a MENU feature controlled by the programmable logic of the controller which allows the length of the sound clip to be controlled. Alternately, other modes are provided for recording sound without use of the video capture mechanisms, if desired. Audio data is stored in a WAV format, though other formats with varying degrees of compression may also be used. In the present embodiment, approximately 17 minutes of sound data memory are provided though this quantity can easily be varied.

Figure 18:
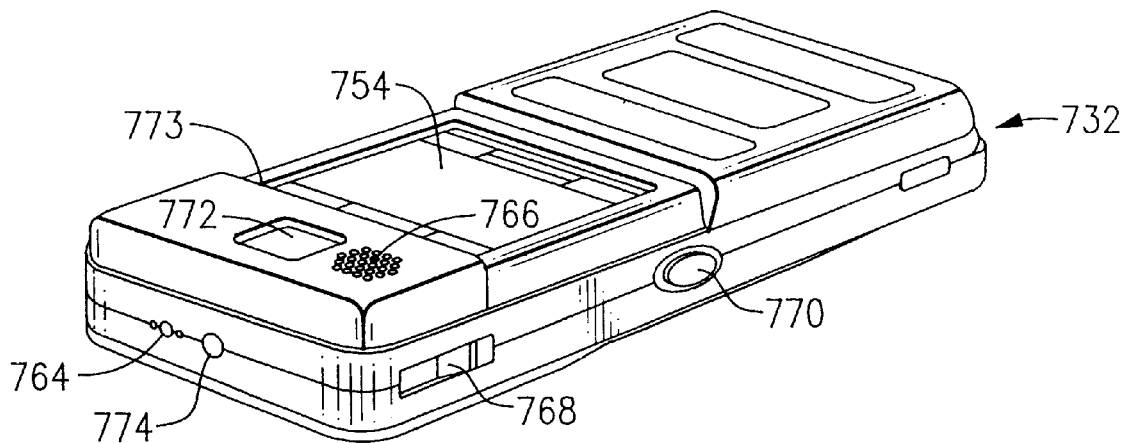
FIG. 18 is a side perspective view of the instrument of FIG. 17, with the sliding cover being moved to an open position to allow access to a touch sensitive display.
Figure 19:
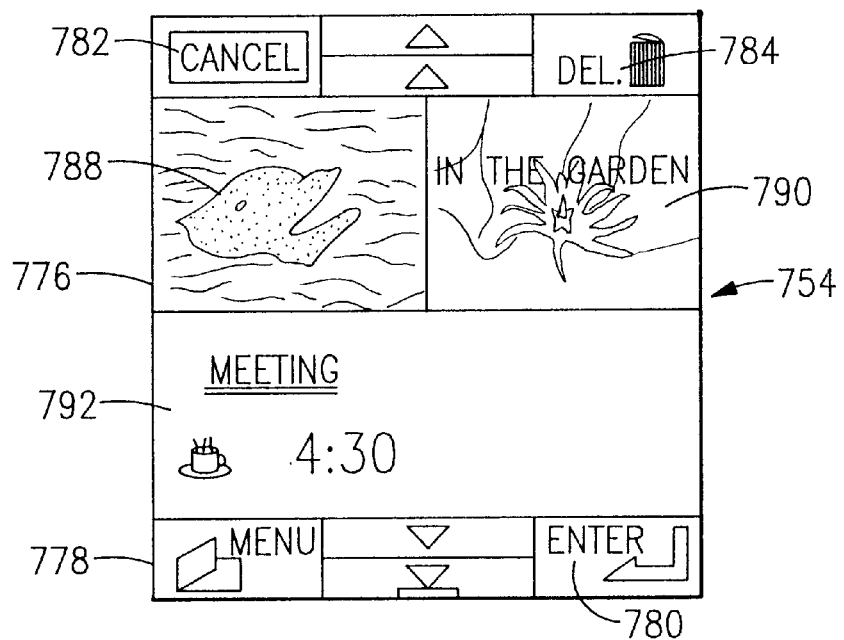
FIG. 19 is a partial rear view of the instrument of FIGS. 14–18, showing video display and annotation features of the touch sensitive display.

Referring briefly to FIGS. 18 and 19, the TFT display 754 according to the present embodiment includes a main window 776 and a plurality of selectable keys disposed about the periphery thereof, including a key for accessing a main menu 778, an ENTER key 780, a CANCEL key 782, and a DELETE key 784. Keys 786 are also provided to allow scrolling in either vertical direction. The main window 776 can be selectively divided into separate image fields for allowing multiple stored digital images to be displayed simultaneously, and to allow annotation relating to a displayed image(s). Exemplary image fields 788 and 790 and an annotation field 792 are shown in FIG. 19, though preferably the microprocessor allows literally any number of separate fields to be made available. For example, a plurality of miniature captured images (not shown) can be displayed in a sequential manner as a slide show presentation on the main window 776. A stylus pen (not shown) selectively allows notes to be added in the illustrated annotation field 792. The notes are also stored into the internal memory of the instrument 432.

For reasons which are apparent below, the programmable logic of the controller of the described instrument 732 also includes an internal calendar, including a date and time stamp which automatically provides an entry which is stored with each corresponding video and/or audio image captured by the camera. In an alternate embodiment, not shown, the multimedia instrument could conceivably link forms of data input selectively or not at all. For example, video may not be required for certain applications which may require only annotation and audio data, etc.

Image data in internal memory are stored in the presently described instrument using JPEG compression to reduce the amount of memory they consume. Image quality can be enhanced by adjusting of a menu setting in order to produce either high quality photographs or normal (compressed) photographs which increases the compression ratio and reduces the amount of memory needed to store each photograph. In the described camera, the high quality mode allows 66 images to be stored using a compression ratio of 10:1 and 132 photographs to be stored using a compression of 20:1 in the normal mode.

Additional detail relating to certain specific features, including use of the menus of the display of the herein described digital camera are provided in the COOLPIX 300 User's Manual, the entire contents of which are incorporated by reference. The theory of operation relating to each of these features, except as indicated, do not form an inventive part of the present invention. Therefore, no further discussion is required, except as pertinent to the present invention.

Figure 17:
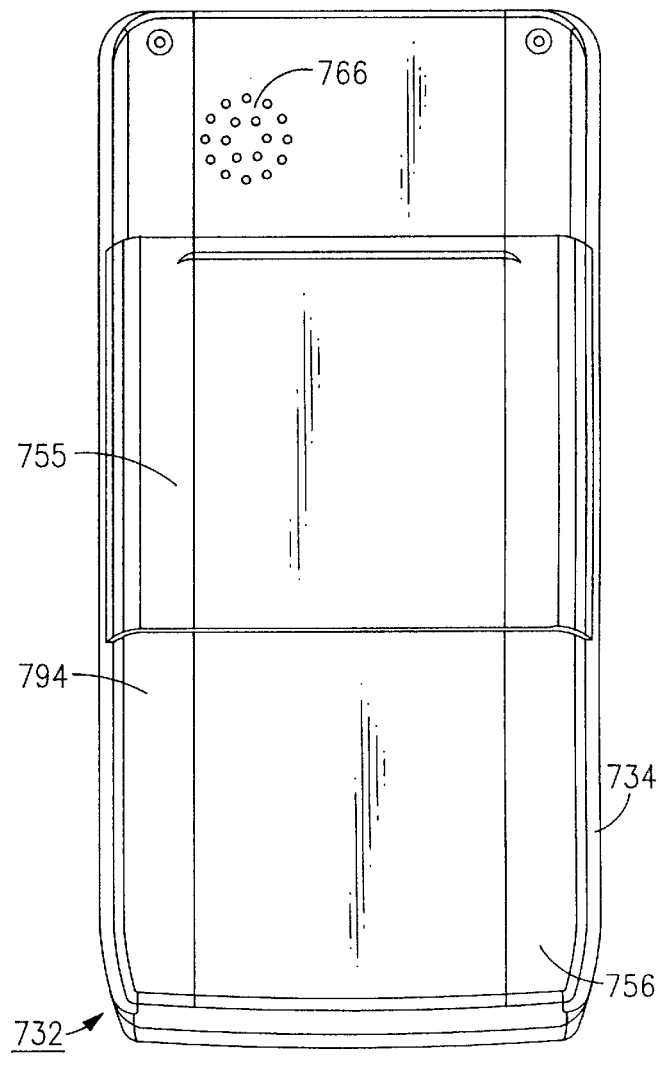
FIG. 17 is a rear elevational view of the multimedia instrument of FIGS. 14–16(a)

Preferably, the instrument housing 734 includes a compartment 794, FIG. 17, accessible from the rear side 756 thereof for retaining a set of rechargeable batteries (not shown) for powering the instrument 732. Alternately, a separate adapter cord (not shown) can supply power from a suitable AC outlet (not shown).

The instrument 732 further includes a serial port (not shown) and an SCSI port (also not shown in this embodiment) allows selective interconnection to a computer (not shown) or to a docking station or cradle 796, FIG. 34, which is similarly linked to a PC or PC network, according to a preferred embodiment described in greater detail below. Alternately, the stored audio and video data can also be transmitted to a video printer, or other suitable peripheral device(s) (not shown).

LATCHING MECHANISM

Figure 16A:
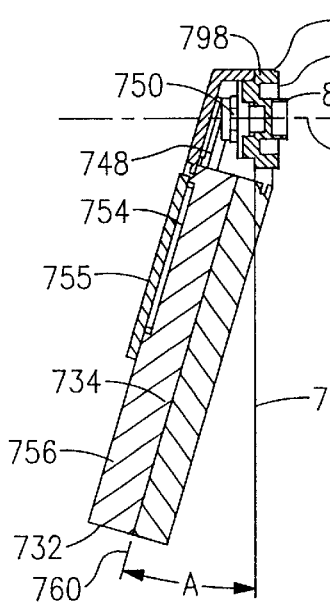
FIG. 16(a) is a side sectional view of the multimedia instrument as taken through line 16—16 of FIG. 15.
Figure 16B:
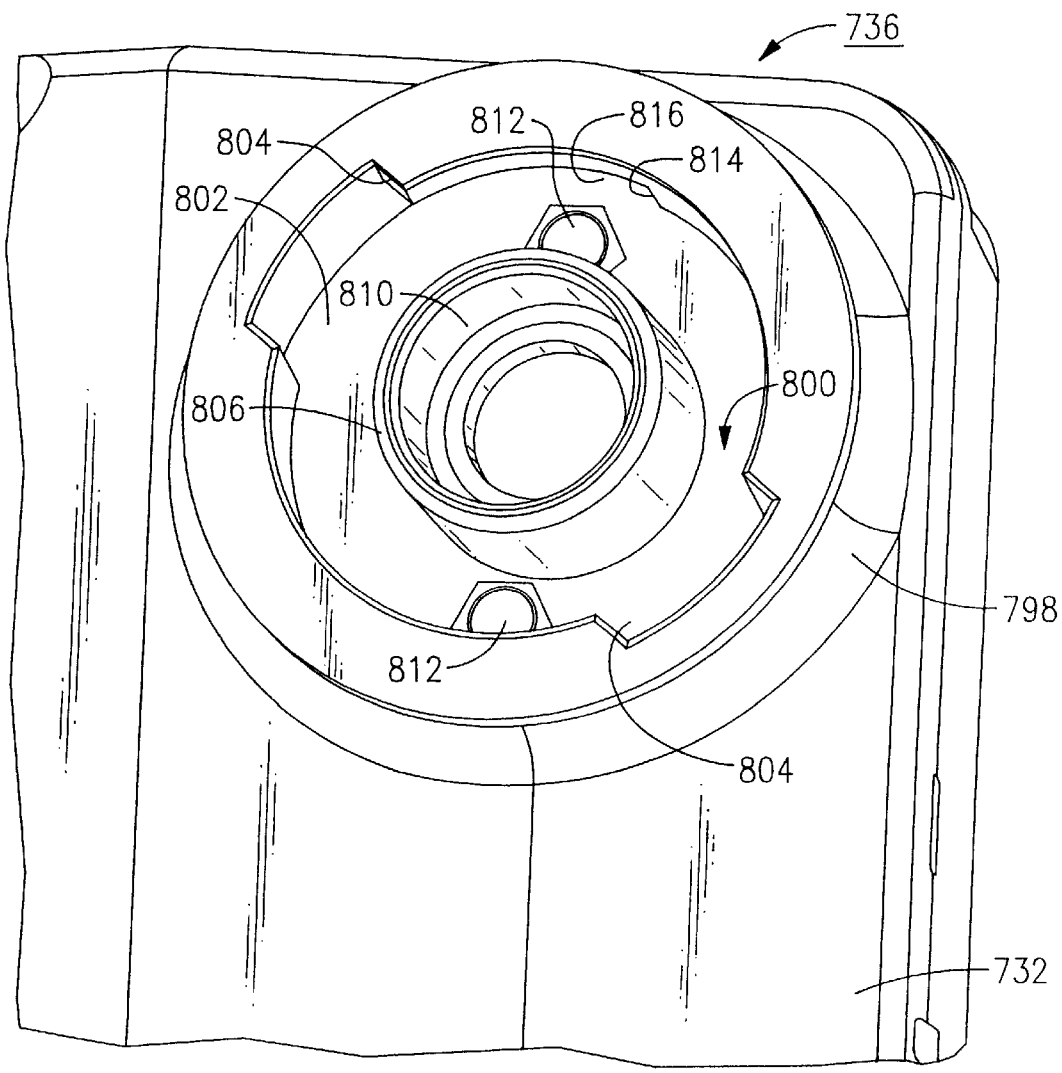
FIG. 16(b) is an enlarged front isometric view of a front interface of the multimedia instrument of FIGS. 14–16(a)

With reference to FIGS. 15, 16(a) and 16(b), the front interface 736 of the herein referred to multimedia diagnostic instrument 732 provides releasable but locking engagement with latching members provided on the rear side of each of the instrument heads 738, 740, 742, 746, FIG. 14. Furthermore, engagement also allows electrical contact to be made with illumination sources (if any) provided in the attached instrument head of choice, without interfering with the optical path to the electronic imaging element 750. Attachment of an instrument head of choice using the described latching mechanism also aligns the optical components of the instrument head with the instrument viewing axis 753.

The latching mechanism is nearly identical to that described in the first embodiment above. In brief, the front interface 736 includes an open-ended distally extending section 798 having a centrally disposed and substantially circular cavity 800 with a defined planar mounting surface 802. As noted, the cavity 800 is substantially circular, with the exception of a pair of diametrically opposed tab sections 804.

A cylindrical pilot section 806 projects distally from the planar surface 802, the section comprising a circular cross section and an open end 808 centrally disposed about an aperture 810 which directly communicates with the interior 748, FIG. 16(a), of the diagnostic instrument 732. Specifically, the aperture 810 is coaxial with the viewing axis 753, FIG. 16(a), and extends directly into the instrument 732 to the imaging substrate (light receiving surface) of the electronic imaging element 750, FIG. 16(a), as supported within the housing 734, FIG. 16(a). Though not shown in this embodiment, a lens element could be supplied within the pilot section and aligned with the imaging element 750 in lieu of or in combination with any of the instrument heads. That is to say, a general or other optical system can be alternately supplied in the instrument interface.

A pair of electrical contacts 812 connected at an interior end thereof (not shown) to a series of power transmission lines (not shown), each include an opposite exposed end, which is preferably flush with the planar mounting surface 802. According to this embodiment, the electrical contacts 812 are diametrically opposed from one another, and are disposed adjacent the tab sections 804. A pair of stops 814 (only one being shown in FIG. 16(b)) is provided within respective annular slots 816, each extending radially from one side of each tab section 804.

The front interface 736 engages the rear or proximal face of a corresponding instrument head of choice. For purposes of explanation, the following description relates to the otoscopic instrument head 746, though each instrument head includes similar features for releasable attachment to the diagnostic instrument 732.

Referring to FIGS. 20–23, the otoscopic instrument head 746 of this embodiment includes a latching member 818 similar to that described in FIGS. 4(a)–4(d) above, the member having a rounded configuration, with the exception of a pair of diametrically opposite ear portions 820 and a pair of flat edges 822. The latching member 818 is disposed within a correspondingly shaped cavity 824 provided in a flat ring 826 fixedly secured to the rear face of the instrument head 746 by known means.

The latching member 818 is a cylindrical member having a pair of open ends centrally disposed relative to a center opening or aperture 828 communicating with the interior of the instrument head 746. A pair of diametrically opposed cylindrical electrical contact elements 830 are slidingly attached to the latching member 818 for axial movement thereof adjacent the ear portions 820 through openings extending into the interior of the instrument head 746. According to this embodiment, the contact elements 830 are made from metal, though other materials may be substituted.

Preferably, the latching member 818 is made from plastic (although other non conducting materials can be used), and includes an inner annular shoulder (not shown) disposed within a cavity formed in the interior of the rear face thereof.

Still referring to FIGS. 20–23, the latching member 818 is intentionally biased rearwardly of the flat ring 826 by a pair of internal spring fingers 827 to a first or home axial position. A pair of contact springs 834 are fixedly attached to the interior facing side 836 of a rear support 839 and includes a depending spring end portion aligned with the inwardly extending end of a contact member 830 so as to supply a bearing force thereupon.

In use, the rear support 839 of the otoscopic instrument head 746 is brought into engagement with the front interface 736 of the instrument body 734. The latching member 818 is aligned with the cavity 800, and more specifically the ear portions 820 are aligned with the tab portions 804. Preferably, the cavity 800, including the tab portions 804 closely match the profile or contour of the latching member 818. The engagement of the cylindrical pilot portion 806 causes the latching member 818 to be directed forwardly toward the interior of the instrument head 746 against the bias of the internal spring fingers 827.

Rotation of the entirety of the instrument head 746 in a clockwise manner; as perceived looking at the front interface 736, advances the ear portions 820 into the annular slots 816 until engagement with the stops 814. The described rotational movement causes the contact members 830 to align with and engage with the corresponding electrical contacts 812 in the interface 736, thereby supplying electric power to a supported lamp assembly 840, as described below.

To initiate release, a user reverses the above procedure by grasping and rotating the instrument head 746 in the opposite (counterclockwise) direction until the ear portions 820 are aligned with the tab portions 804 in the interface 736. The instrument head 746 is then pulled axially away from the interface 736, causing the latching member 818, as biased by the internal spring fingers 827, to be moved back into the initial axial position.

As noted, each of the instrument heads are similarly attached and detached from the front interface 736 of the instrument 732. Other salient features of each of the instrument heads used in the present embodiment will now be described.

OTOSCOPIC INSTRUMENT HEAD

Referring first to FIGS. 14 and 20–24, the otoscopic instrument head 746 of this specific embodiment includes a substantially cylindrically shaped rear or proximal housing portion 839, an intermediate portion 842, and a frusto-conical front or distal insertion portion 847. The distal insertion portion 847 includes an interior which includes overlapping and conically shaped inner and outer tip housings, 848, 850, each having a respective distal tip opening 852, 854. As clearly illustrated in FIG. 23, the inner tip housing 848 extends distally from the tip opening 854 of the outer tip housing 850. A hollow safety speculum 846, made from a plastic material and having a distal tip opening 906, is mounted onto the conical periphery of the front insertion portion 847, also in overlapping relation thereto. Each of the tip openings 850, 848, 906 are coaxial with one another along a defined optical axis 856, the tip openings of the mounted speculum 846 and the front insertion portion 847 being slightly displaced from the tip opening 852 of the inner tip housing 848.

Figure 24:
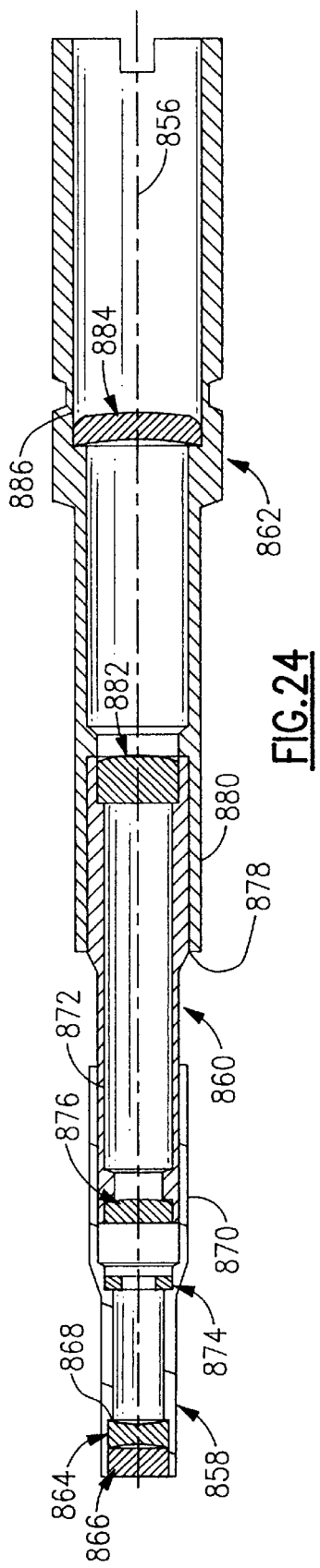
FIG. 24 is an enlarged sectional view of the optical system of the otoscopic instrument head of FIGS. 20–23.
Figure 22:
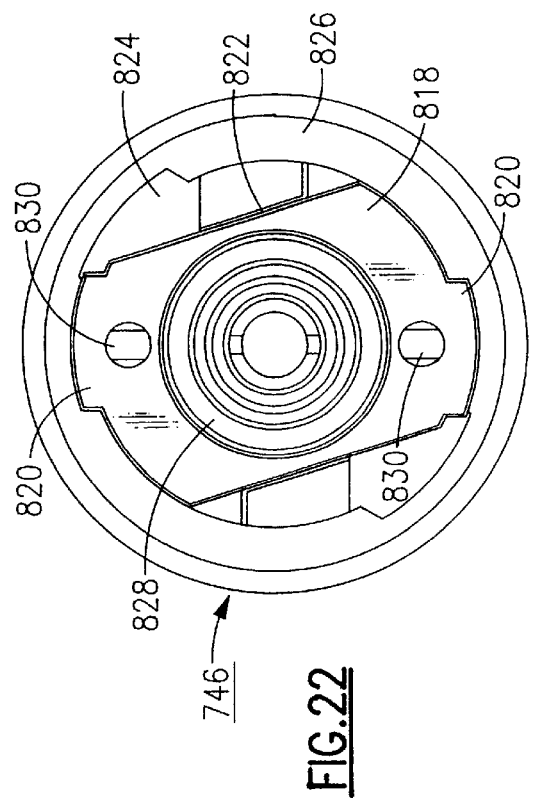
FIG. 22 is a rear view of the otoscopic instrument head of FIGS. 20 and 21.

Referring to FIGS. 23 and 24, the optical system of the otoscopic instrument head 746 is comprised of a series of axially interconnected lens tubes 858, 860, 862 arranged within the interior of the instrument head 746 along an optical axis 856. A negative lens element 864 is disposed in a first lens tube 858 adjacent the distal opening 852 of the inner tip housing 848, FIG. 23. A plano glass section 866 is disposed directly in front of the negative lens 864. Preferably, the interior wall of the first lens tube 858 defines a shoulder 868 for supporting and positioning the two optical elements 864, 866. The proximal end 870 of the first lens tube 856 is wider than that of the remainder of the tube and is sized for receiving the distal end 872 of the attached second lens tube 860. An aperture plate 874 and a second lens element 876, are retained within the widened proximal end 870 of the first lens tube 858 prior to the distal end 872 of the second lens tube 860. The second lens element 876 is a positive lens of sufficient power. A proximal end of the second lens tube 860 is retained within a cavity 878 of the distal end 880 of a third lens tube 862, wherein a third lens element 882 is attached at the proximal end of the second lens tube 860. The third lens element 882 is a doublet containing a concave and convex lens of an appropriate size. Finally, a fourth singlet lens element 884 is disposed in a cavity 886 at approximately the midpoint of the length of the third lens tube 862. In use, an optical signal is channeled through the above disposed lens elements and is ultimately focused at the imaging substrate of the electronic sensor of the diagnostic instrument upon assembly. It should be readily evident that the fourth lens element 884 could alternately be disposed within the pilot section 806, FIG. 16(*b*), of the instrument 732.

When attached, the optical axis 856 of the otoscopic instrument head 746 is coaxial with the viewing axis 753, FIG. 16(*a*), of the instrument 732, each of the above described lens elements being spaced to allow the optical signal to be focused onto the imaging substrate (not shown) of the electronic imaging element 750.

As most clearly seen in FIGS. 21 and 23, the otoscopic instrument head 746 includes a miniature halogen lamp 888 disposed conveniently within the rear housing portion 839 and press-fitted within a spring-metal receptacle 890. The receptacle 890 is defined by a spaced enclosure 892 which is preferably formed by a pair of metal supporting ribs 894, 896 mounted to the interior side of a rear support 898. The spring metal receptacle 890 forms a pocket sized for retaining the halogen lamp 888, which is preferably angled relative to the optical axis 856.

One of the metal supporting ribs 894 extends behind the lamp 888 while the second supporting rib 896 extends to the front and sides thereof Each of the supporting ribs 894, 896 include sections 900 (only one being shown) extending along the rear support 898, and thereby defining the previously described flat springs 834, such that when the contacts 830 engage the contacts 812 in the instrument body 734, an electrical circuit is completed, allowing the lamp 888 to be powered automatically.

Referring to FIG. 23, light from the halogen lamp 888 is directed to one end of a bundle 902 of optical fibers. The bundle of fibers 902 are fanned out into an annular space 904 formed between the exterior of the lens tubes 858, 860, 862 of the optical system and the interior wall of the inner tip housing 848 so as not to interfere with the transmission of optical data. The bundle of fibers 902 terminate at the distal tip opening 852 as a polished light emitting end.

As noted, the safety speculum 846 is preferably attached in a releasable manner to the exterior of the front insertion portion 847 using a bayonet attachment as described in commonly owned U.S. Pat. No. 4,380,998 issued to Kieffer, et al, the entire contents of which are herein incorporated by reference. In use, the previously described latching mechanism allows the instrument head 746 to be locked into engagement with the front interface 736 of the instrument body 734. This engagement allows a proper electrical interconnection to power the lamp 888 which directs light through the optical fiber bundle 902 to the distal tip opening 906 of the insertion portion 846. In addition, insufflation capability can be provided through a separate port (not shown) to allow stimulation of the tympanic membrane.

The target of interest (the interior of the ear canal) is viewed through the aligned tip openings, allowing an optical image along the aligned axes 856,753. The lens elements of the optical system are preferably spaced so as to focus the image directly onto the electronic imaging element 750.

GENERAL PURPOSE INSTRUMENT HEAD

Figure 25:
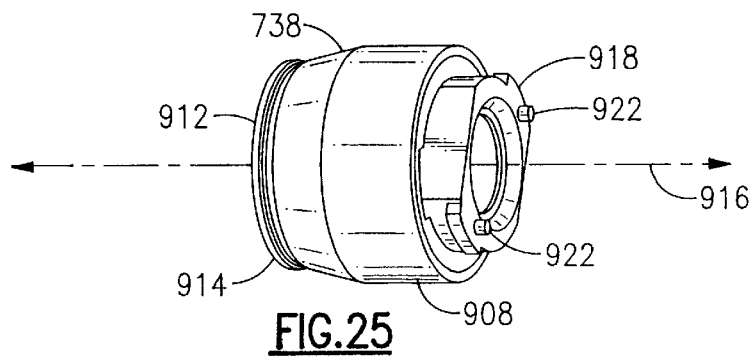
FIG. 25 is a front perspective view of the general viewing instrument head illustrated in FIG. 14.
Figure 26:
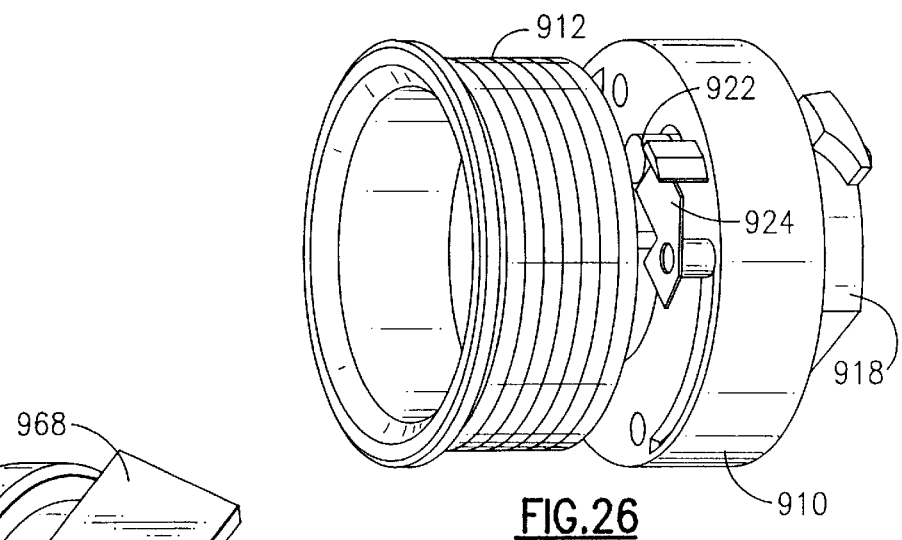
FIG. 26 is an enlarged partially cutaway isometric view of the general viewing instrument head of FIG. 23, rotated approximately 45 degrees.

Referring now to FIGS. 14, 25 and 26, the general purpose or general-viewing instrument head 738 according to the present multimedia instrument embodiment includes a cylindrical housing 908 having a rear plate 910 and a defined hollow interior. An adjustable lens assembly 912 is securely mounted within a lens holder which is threaded or otherwise attached through an opening provided in a distal end 914 thereof. The adjustable lens assembly 912 includes at least one objective lens and an aperture plate of sufficient size to provide an enhanced field of view for the diagnostic instrument 732 when assembled thereto. According to the present embodiment, a field of view of approximately 40 degrees is provided, but this parameter can be easily varied depending on the application. The lens assembly 912 of the present embodiment is movable along a defined axis 916 so as to focus at a wide range of distances, allowing a formed optical image to be focused onto the electronic imaging element 750, FIG. 15, while varying the object distance. As noted, the instrument head 738 is attached to the front interface 736 of the instrument 732, in the manner previously described above.

This particular instrument head design does not include an illumination assembly although one could be added, depending on the application. However, the latching member 918 includes a pair of non-electrical contact members 922 extending through the rear plate 910. Each contact member 922 includes an interior end for separately engaging a pair of flat springs 924 fixedly attached to the interior side of the rear plate 910. The springs 924 provide a bias for engaging and locking the instrument head 738 in place with the front interface 736 of the instrument 732.

In use, the optical path proceeds in an uninterrupted manner through the interior of the instrument head 738 and the opening defined in the latching member 918, which is focused at the electronic imaging element 750, FIG. 15.

SURFACE MICROSCOPE HEAD

Referring to FIGS. 27–30, the surface microscope head 740 of the instant embodiment includes a two-piece construction comprising a cylindrical housing shell 930 having a hollow interior 932 with open distal and proximal ends 934, 936. A second section 938 is fitted into the interior 932 of the housing 930. As most clearly shown in FIG. 28, the second section 938 includes a base portion 940 and a curved side wall 942 which is sized to fit within the interior 932 of the housing 930, the curved side wall being fitted within an axial slot 944. A protruding portion 946 of the side wall 942 adjacent the distal end 934 of the instrument head 740 is used for retaining a miniature halogen lamp 948.

The base portion 940 includes a cavity 950 sized for retaining a latching member 952. The latching member 952 operates nearly identically in principle to those previously described above. The miniature halogen lamp 948 is retained in a pocket 949 formed by a spring metal receptacle 956 located within the protruding portion 946 of the side wall 942. As noted previously, such lamps are well known in the field and do not form an essential part of the present invention. That is to say, other suitable light sources can be substituted, as noted previously herein.

Figure 28:
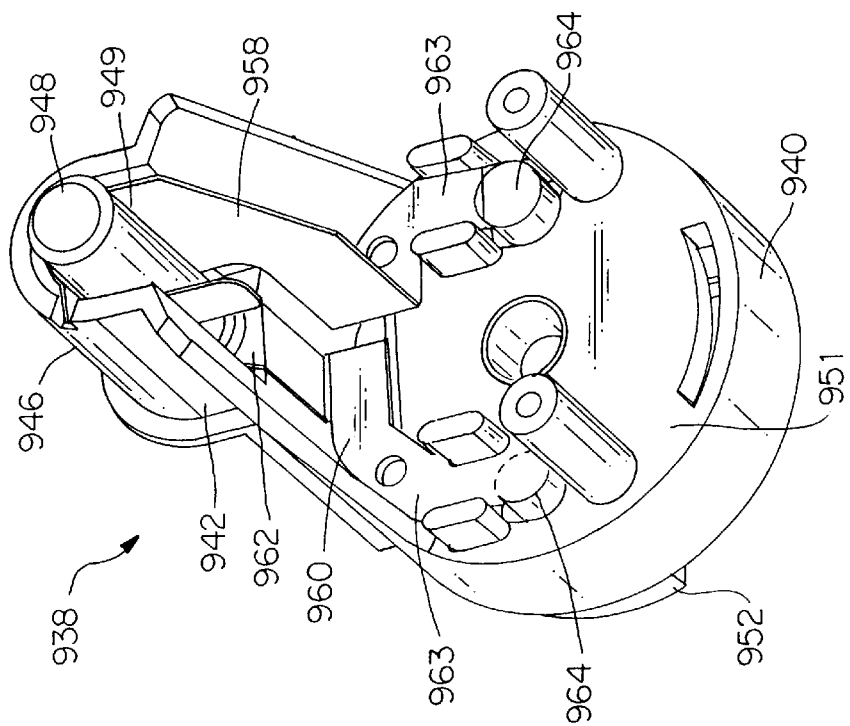
FIG. 28 is a cut-away partial rear perspective view of the surface microscope head of FIGS. 26 and 27.

The receptacle 956 is defined by one of a pair of contacting plates 958, 960. The first plate 958, as shown in FIG. 28, forms a spring loaded sleeve for the miniature lamp 948 while the second plate 960 includes a flat portion 962 in contact with the rear portion of the lamp and the electrical contacts (not shown) thereof. Each of the contacting plates 958, 960 is manufactured from a spring metal extending in parallel configurations along the interior side or wall 956 of the rear portion 940. A portion of each plate 958, 960 is fixedly attached with a depending spring end 963 of each being cantilevered into biasing contact with axially movable contact members 964 extending through the rear portion 940.

Figure 27:
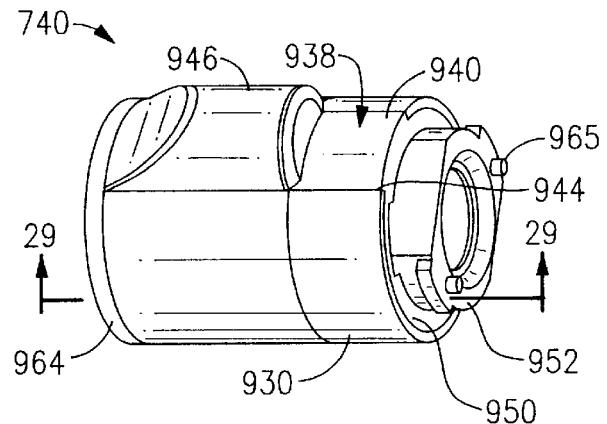
FIG. 27 is a side view of the surface microscope head of FIG. 26.
Figure 29:
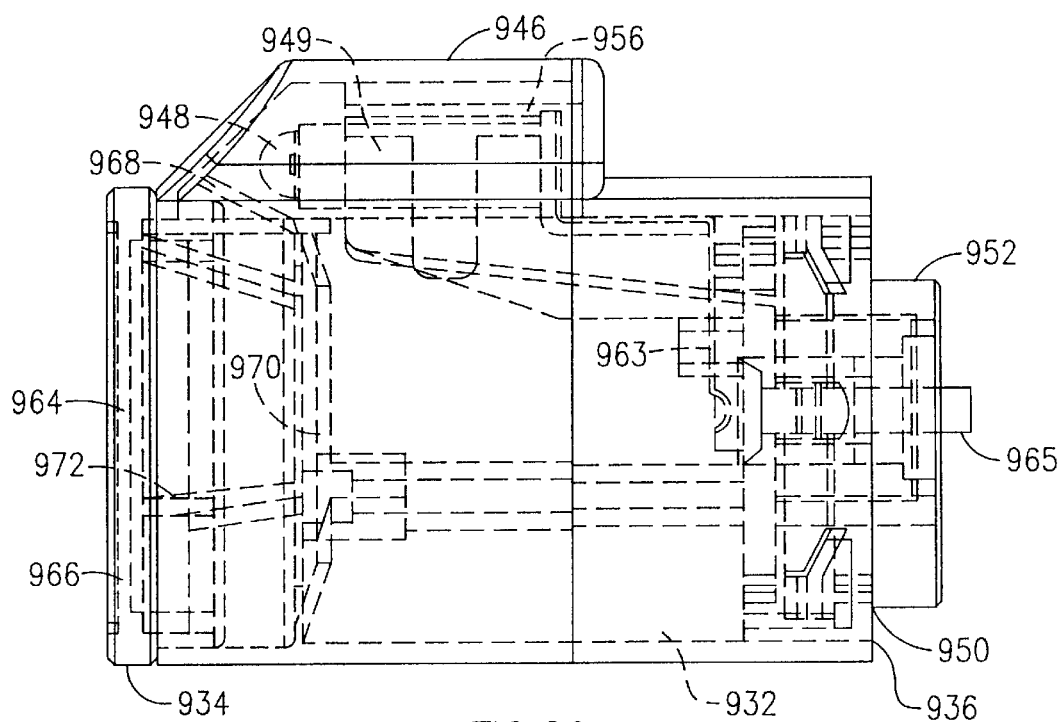
FIG. 29 is a sectional view of the surface microscope head of FIG. 27, as taken through the line 29—29.
Figure 32:
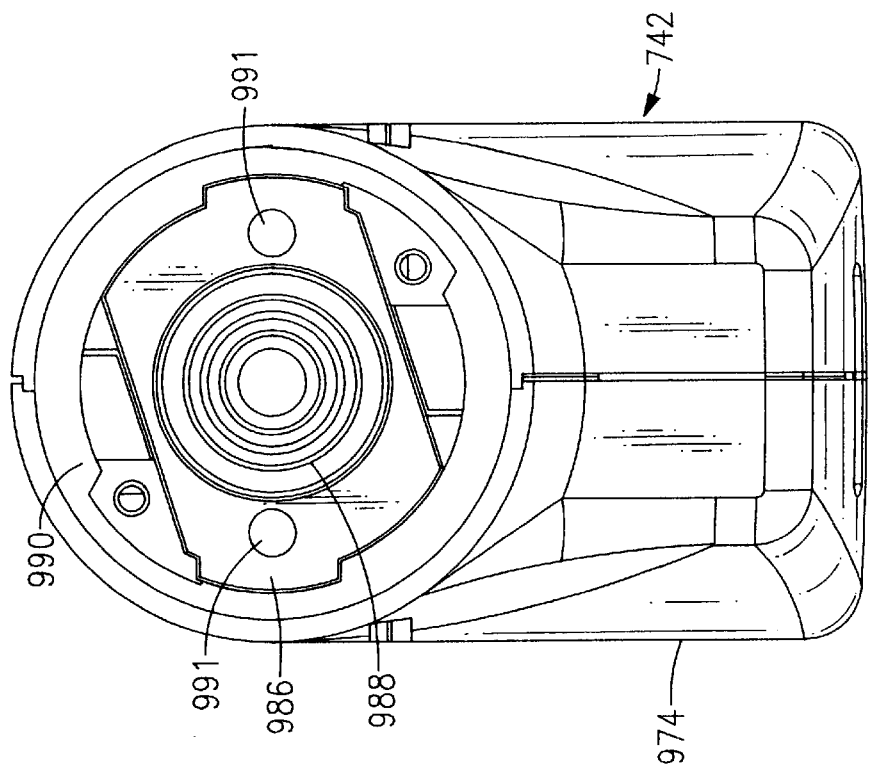
FIG. 32 is an enlarged rear view of the instrument head of FIG. 31.

In an unattached condition, the latching member 952 is biased by the depending spring ends 962 into a first axial position directed outward or rearward of the proximal end 936, as shown most particularly in FIGS. 27 and 29.

As in the preceding, attachment of the instrument head 740 to the front interface 736 of the instrument body 734 causes the latching member 952 to overcome the bias of the springs 962 and causes intimate contact, completing an electrical circuit with the miniature lamp 948 and causing illumination thereof.

Referring to FIG. 29, a releasably attachable lens holder 964 is disposed at the distal end 934 thereof. The lens holder 964 accommodates a direct skin contacting window 966 having a measuring reticle (not shown) for providing a frame of reference of a target of interest. For purposes of this embodiment, the skin contacting window 966 provides a field of view of approximately 15 mm, and is releasably attachable to allow cleaning and/or sterilization. The skin contacting window 212 according to this embodiment is made from a plate glass, though any optical grade material including light plastics such as acrylic, or polycarbonate are suitable.

Figure 30:
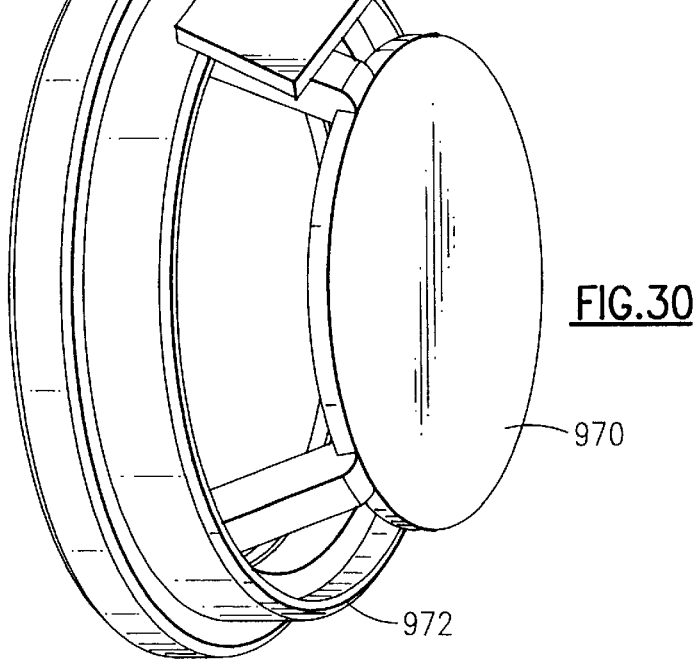
FIG. 30 is a side perspective view of the polarizing lens assembly of the instrument head of FIGS. 27–29.

Referring to FIGS. 29 and 30, a pair of crossed, linear polarizer elements 968, 970 are disposed on a support assembly 972, aligning a first polarizer element 968 with the illuminating end of the halogen lamp 948, and angled thereto. The support assembly 972 includes a three point mount fitted within the center opening defined by the lens holder 964 and having a second polarizing lens or element 970 disposed proximally from the skin contacting window 966. The support assembly 972 is preferably rotatable relative to the skin contacting window 966 (the viewing axis) to polarize incoming light as needed in order to minimize glare. In current practice, glare from the skin surface is removed by applying a layer of oil to eliminate the air/tissue interface. Oil could still be applied, but the crossed linear polarizers eliminate much of the specular glare from the surface.

Still referring to FIG. 29 and 30, the first polarizer element 968, being angled relative to the viewing axis 753, FIG. 16(*a*), causes light to indirectly strike the viewing window 966 in order to minimize reflective glare from the inside surface thereof, and to prevent an image of the miniature lamp 948 to be reflected optically through. The support assembly 972 is preferably attached to the lens holder 964 by known means.

In use, the instrument head 740 is mounted to the front interface 736 of the diagnostic instrument 732 in the manner previously described such that the latching member 952 inwardly deflects when engaged therewith. This deflection causes the cylindrical contact members 964 to bear against the respective depending spring ends 963 of the supporting plates 958, 960. Subsequent twisting of the instrument head 740, as described above, also aligns the projecting ends of each of the contact members 964 with the contacts 812, FIG. 16(*b*), located in the front interface 736 of the instrument 732. This alignment completes an electrical connection, causing the lamp 948 to automatically illuminate, upon locking of the instrument head 740 in place.

When assembled, the skin-contacting window 966 and the second polarizing element 970, are each aligned with the viewing axis 753 to allow a focused optical image to be transmitted to the electronic sensor 750. In use, a target (such as a wart, lesion, or other skin disorder) is viewed when the skin-contacting window 966 is placed in direct contact therewith.

Alternately, the reticle (not shown) can be spaced from the target of interest by recessing the optical window using an adapter. This allows the image to be viewed, such as a lesion or wart, without compression thereof.

MAGNIFYING INSTRUMENT HEAD

Referring to FIGS. 14 and 31–33, the magnifying instrument head 742 is defined by a two part housing 974 defining an interior sized for supporting an illumination assembly 976 and adjacent supporting fixture 978 including a rear support 980.

Figure 33:
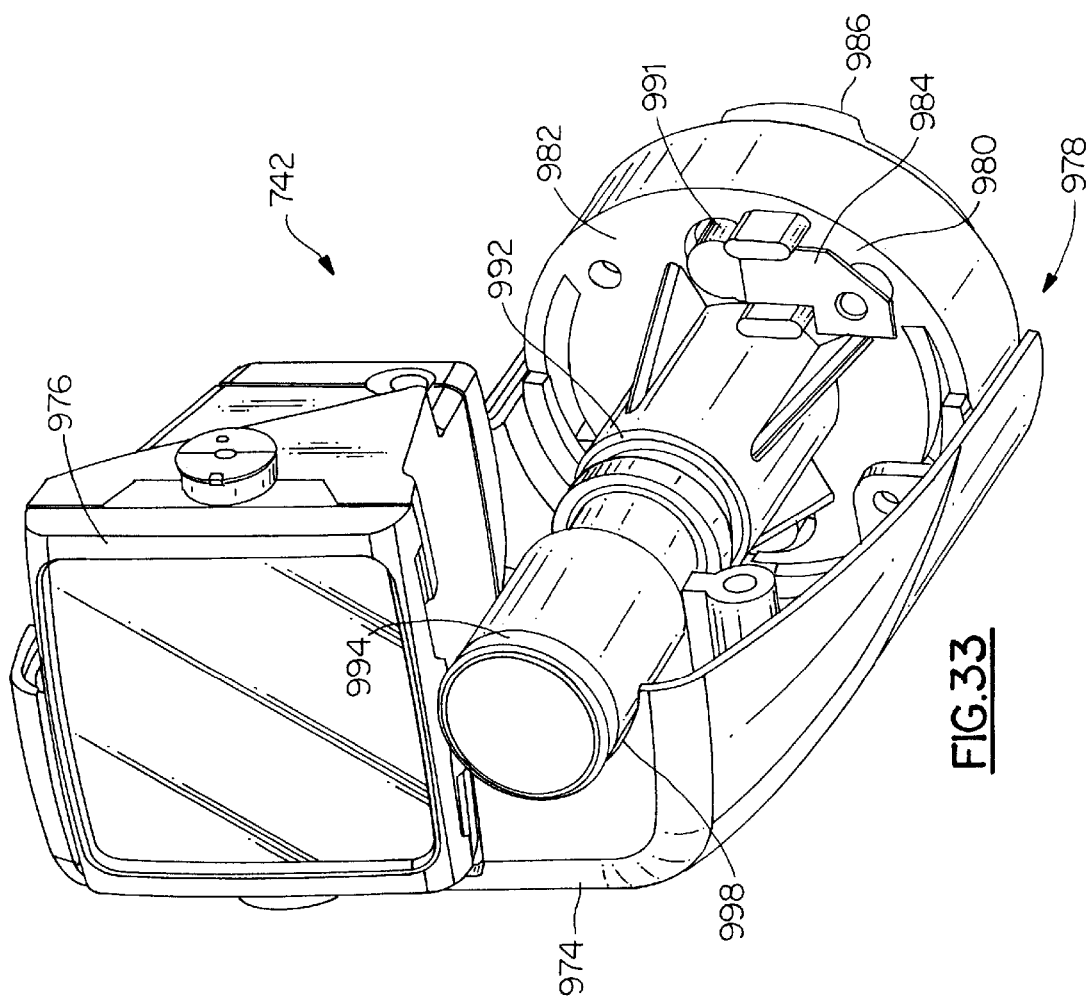
FIG. 33 is a partially cutaway front isometric view of the instrument head of FIGS. 31 and 32.
Figure 31:
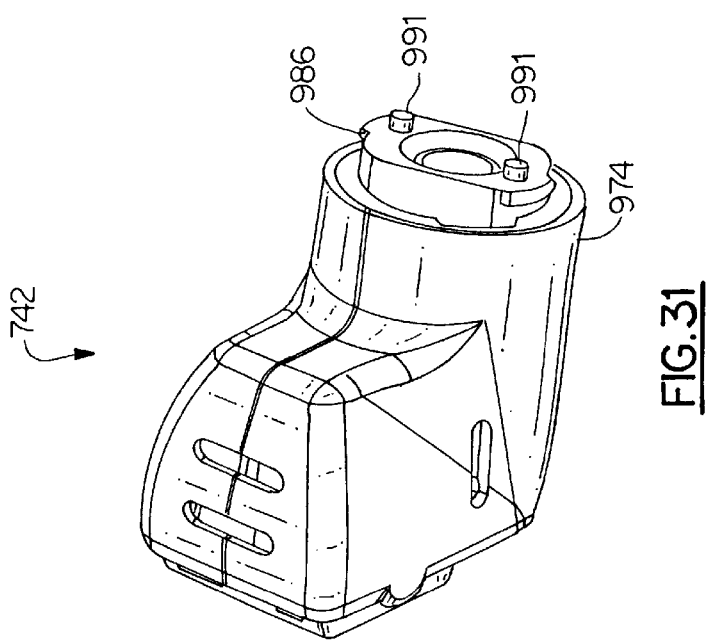
FIG. 31 is a side perspective view of the magnifying instrument head of FIG. 14.

In brief, the illumination assembly 976 includes a halogen lamp (not shown) or other suitable light source which is supported therein as described in greater detail above in the preceding embodiment. The lamp is supported by a set of spring fingers retaining the back end of the lamp and providing electrical contact. A pair of supporting plates (not shown) made from a spring material extend therefrom, at least one of the plates having a portion engaged with the lamp's electrical contacts (not shown). The plates extend therefrom and are supported at the interior side 982 of the rear support 980, each of the plates having a depending spring end 984 (only one of which is shown in FIG. 33).

As noted, the supporting fixture 978 includes a rear support 980 including a latching member 986 supported in a cavity 988 of a flat floating ring 990. The latching member 986 is biased by the depending spring ends 984 (one shown in FIG. 33), attached to the interior side 982 of the rear support 980 (partially shown), also in the manner previously described. The latching member 986 includes a center opening 988 extending into the interior of the housing 974 of the instrument head 742. As in the preceding, the latching member 986 is similar to that described above and having a depending spring ends which bias a pair of fixedly attached electrical contact members 991 having ends extending through openings in the rear portion 980. Hence, and when the latching member 986 is engaged with the front interface 736, FIG. 15, of the instrument 732, FIG. 15, an electrical connection is completed and the halogen lamp of the illumination assembly 976 is automatically illuminated.

A focusing lens assembly 992 defined by a cylindrical lens housing 994 is fixedly supported by the interior wall 982 of the rear support 980. The proximal end of the lens assembly 992 is coaxial with the center openings defined by the rear support 980 and the latching member 986. A distal portion 996, FIG. 14, of the lens housing 984, extends through an opening 998 in the front or distal side of the assembled housing 974. At least one objective lens assembly (not shown) and an adjacent aperture plate (not shown) are contained therein, the details being provided in the preceding embodiment with reference to FIGS. 7(a)–7(c). The lens assembly 992 is preferably rotatably and axially movable therein to permit focal adjustment.

In use, and when the instrument head 742 is assembled to the instrument body 732, FIG. 15, an image perceived by the optics contained in the adjustable lens assembly 992 is transmitted along an axis aligned with the viewing axis 753, FIG. 16(a), to direct an incoming optical signal to the electronic imaging element 750, FIG. 16(a). The lamp is oriented such that a defined illumination axis is angled relative to the viewing axis 753, FIG. 16(a).

The arrangement of the reflectorized lamp system gives a substantially coaxial illumination to the viewing path, such as for imaging anatomy within a cavity.

Figure 36A:
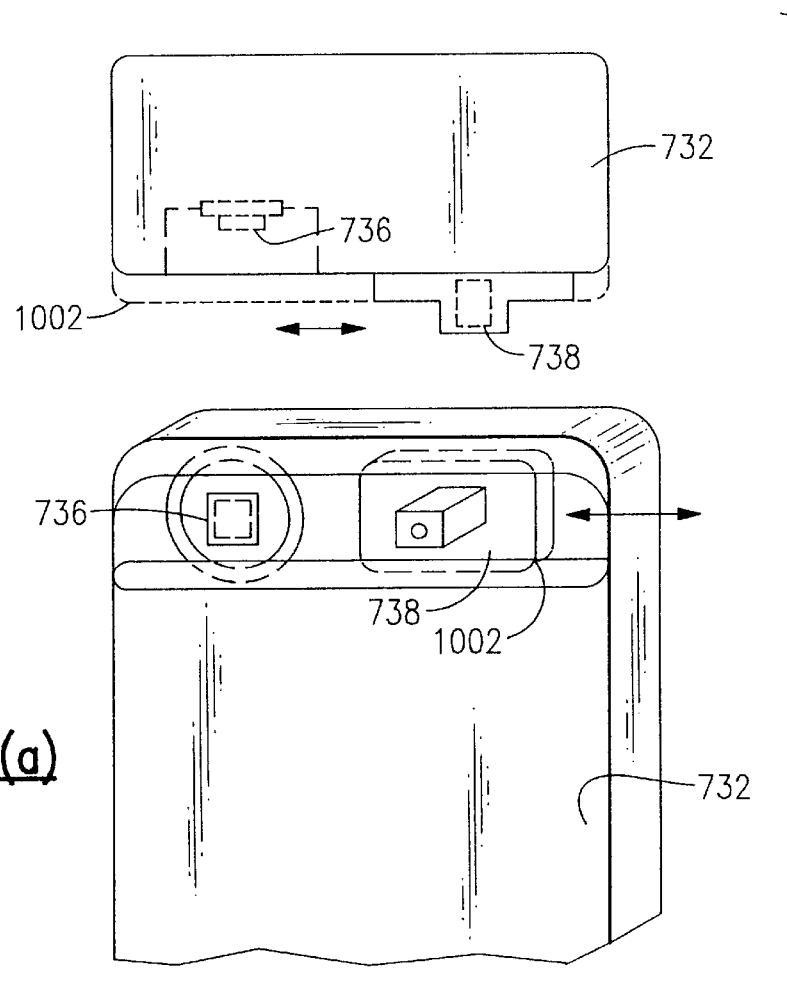
FIG. 36(a) illustrates respective top and front partial views of a multimedia instrument according to a second embodiment of the present invention.

The described embodiment does not provide an optical system for the electronic imaging element 750, FIG. 16(a), when an instrument head is not attached to the front interface 736, FIG. 16(a). In an alternate modification, shown in FIG. 36(a), one of the instrument heads, in this case, the general view instrument head 738, can slide relative to the front side of the instrument body 732 adjacent the front interface 736. Each of the remaining instrument heads (not shown in this view) can be attached selectively to the front interface 736, as needed using the afore mentioned latching mechanism in the manner previously described. The general view instrument head 738, on the other hand, can translate into and out of position with the viewing axis 753 (not shown in this FIG.) of the instrument 732 by sliding the head 738 laterally along a pair of parallel rails 1002. When moved into alignment, the general view instrument head 738, having the latching member 820 (not shown in this FIG.), can engage the front interface 736, also in the manner previously described. Alternately, a single lens element (not shown) can be supplied in the pilot section adjacent the electronic imaging element to provide a general view with a limited field of view.

Figure 36B:
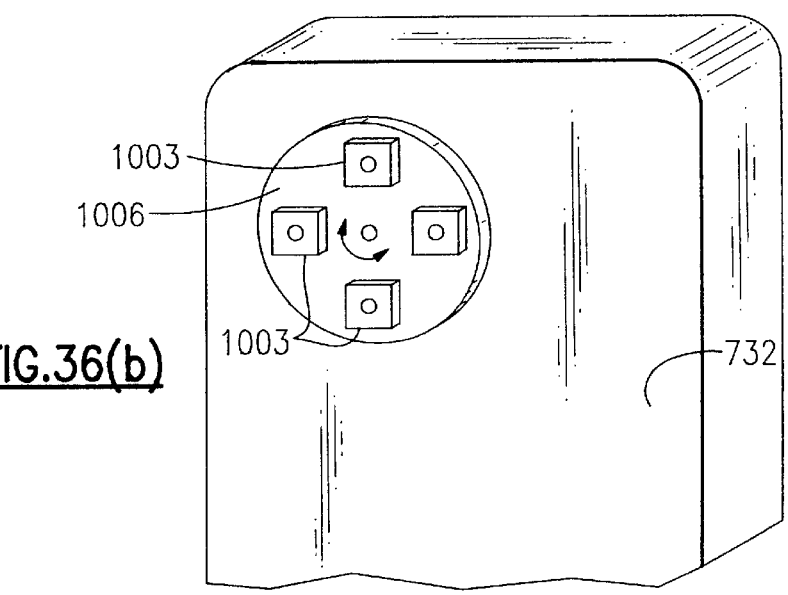
FIG. 36(b) is a partial front view of an instrument in accordance with a third embodiment of the present invention.

According to another alternate arrangement, FIG. 36(b), each of the above described or other instrument heads 1003 can be circumferentially disposed on a rotatable turret assembly 1006, which can be fixedly or removably mounted to the front side of the diagnostic instrument 732. The turret assembly 1006 allows each of the instrument heads to be selectively rotated into position relative to the front interface 736 and into alignment with the electronic imaging element 750, FIG. 16(a). Preferably, the turret assembly 1006 includes detent means (not shown) based, according to this embodiment, on a 90 degree rotation thereof The turret assembly 1006 provides a means for storing those instrument heads that are currently not in use.

The above diagnostic instrument can contain other salient features, including an audible or vibratory alarm (not shown), which can be preset for a predetermined period of time (e.g. 10–15 minutes) to assist the physician to stay on schedule.

DATA MANAGEMENT SYSTEM

A description of a preferred medical data management program is herein described in accordance with the previously described instrument 732 of the preceding embodiment and with reference to FIGS. 34, 35 and 38–43.

Figure 38:
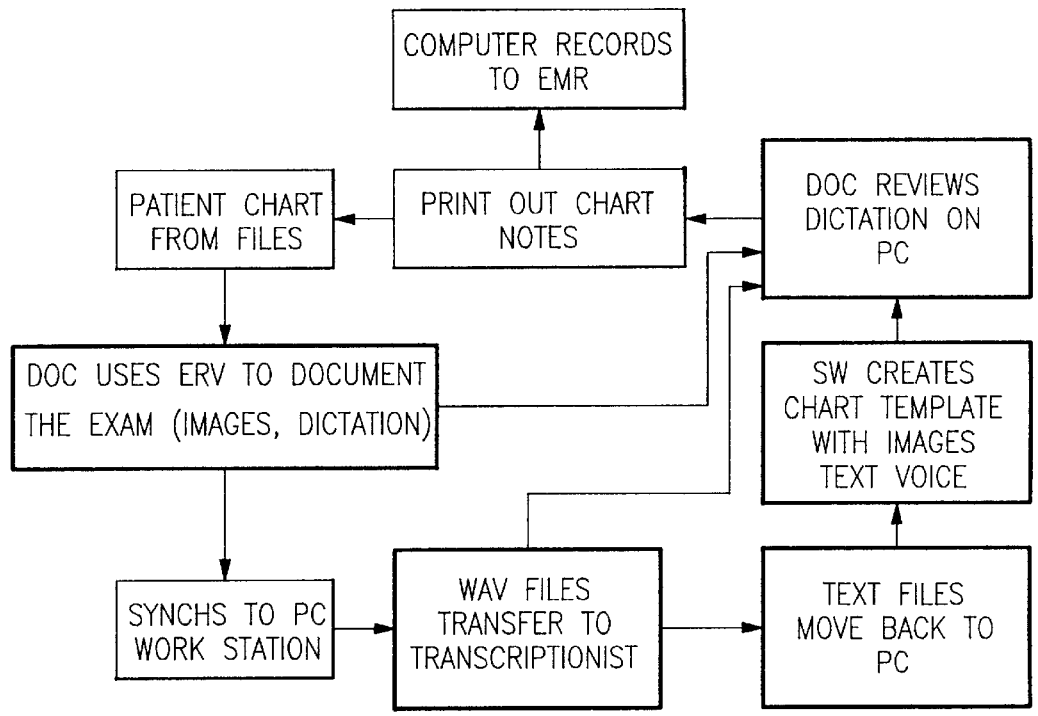
FIG. 38 is a flow chart according to a data management system using the mulitmedia instrument system of FIGS. 14–34.
Figure 42:
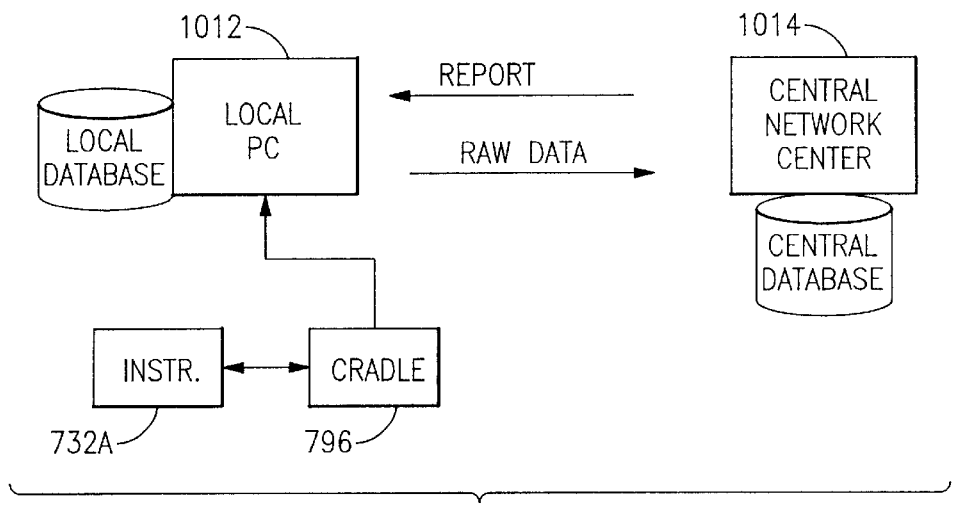
FIG. 42 is a generalized diagram illustrating the transfer of data between a multimedia instrument, a local computer and a data network.
Figure 39:
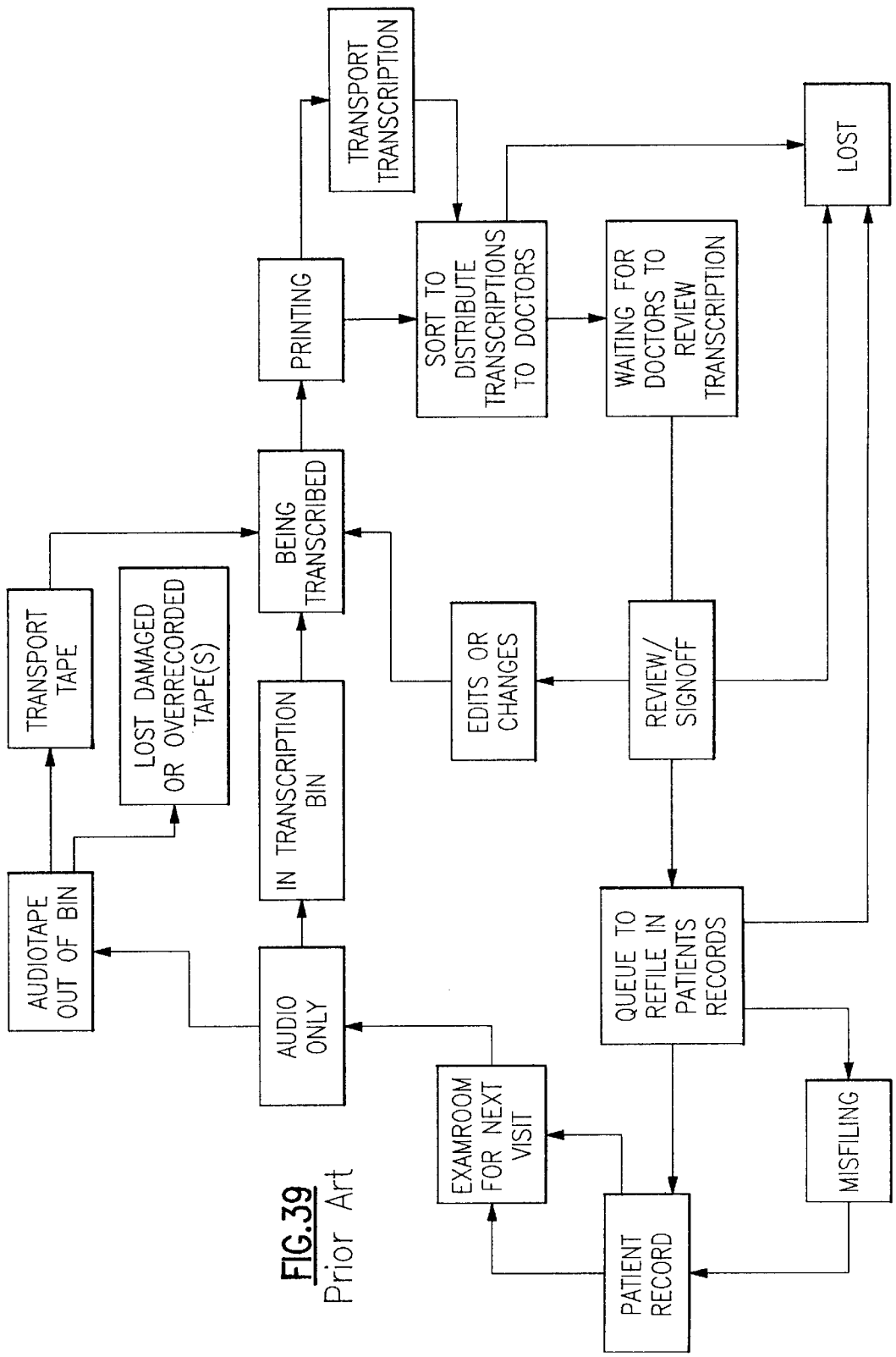
FIG. 39 is a second flow chart of transcription procedure in accordance with the prior art.

Prior to a discussion of the present embodiment, reference is first made to FIG. 38 and 39, which broadly describes a transcription procedure in accordance with the prior art.

Initially and prior to an examination, a patient chart is taken from the office files and given to the physician. The physician then examines the patient, adding his or her notes to the file and dictating as needed during the course of examination, typically using a hand-held tape recorder. The physician identifies the patient and adds a time and date stamp at the start of each dictation session. Usually, a single tape will contain dictation relating to a plurality of patients seen over the course of a typical working day or shift. Often the dictation will be done at the end of the day, when details of the patient visit are sketchy. The doctor must usually rely upon memory, and whatever notes made during the course of examination. As noted, however, a doctor will often see many patients during the day, obscuring the details of a specific visit.

The tape is then sent to a transcriptionist, who listens to the tape, as best understood, and manually types the chart notes. The notes are either into typed into a computer record or onto paper for each patient record on the tape. In any event, a copy of the chart notes are then printed and forwarded to the physician for review. The physician fills in any data which could not be successfully interpreted by the transcriptionist, and otherwise edits the chart notes which are then typed in accordance with the corrections. After again reviewing the chart notes, as necessary, the physician signs off the transcribed record. The record is then added to the patient's file.

A number of potential problems can occur from the above procedure. First, if the tape(s) is faulty or lost, the physician will be required to create the chart records from memory and/or consultation of any written notes which may have been taken during the examination. A similar problem occurs if the tape is prematurely and accidentally erased. The audio tape is the primary source of information, which both the transcriptionist and the physician must rely upon for both creating the draft chart notes and for reviewing purposes. The end result is a heightened probability that the records will be incomplete or inaccurate.

In a similar vein, the printed notes could also be lost or misplaced, potentially delaying the reviewing process. Delays obviously will increase the probability that incorrect or incomplete records will be generated. If video diagnostic instruments of the type previously referred to as being typical of the prior art, FIG. 13, are used, the data obtained from each must also be labeled and separately attached to the file. Based on the amount of time taken, it could be difficult to correctly place this data correctly with the transcribed data, if any. As should be apparent, a myriad of different combinations using various types of data are possible.

Figure 35:
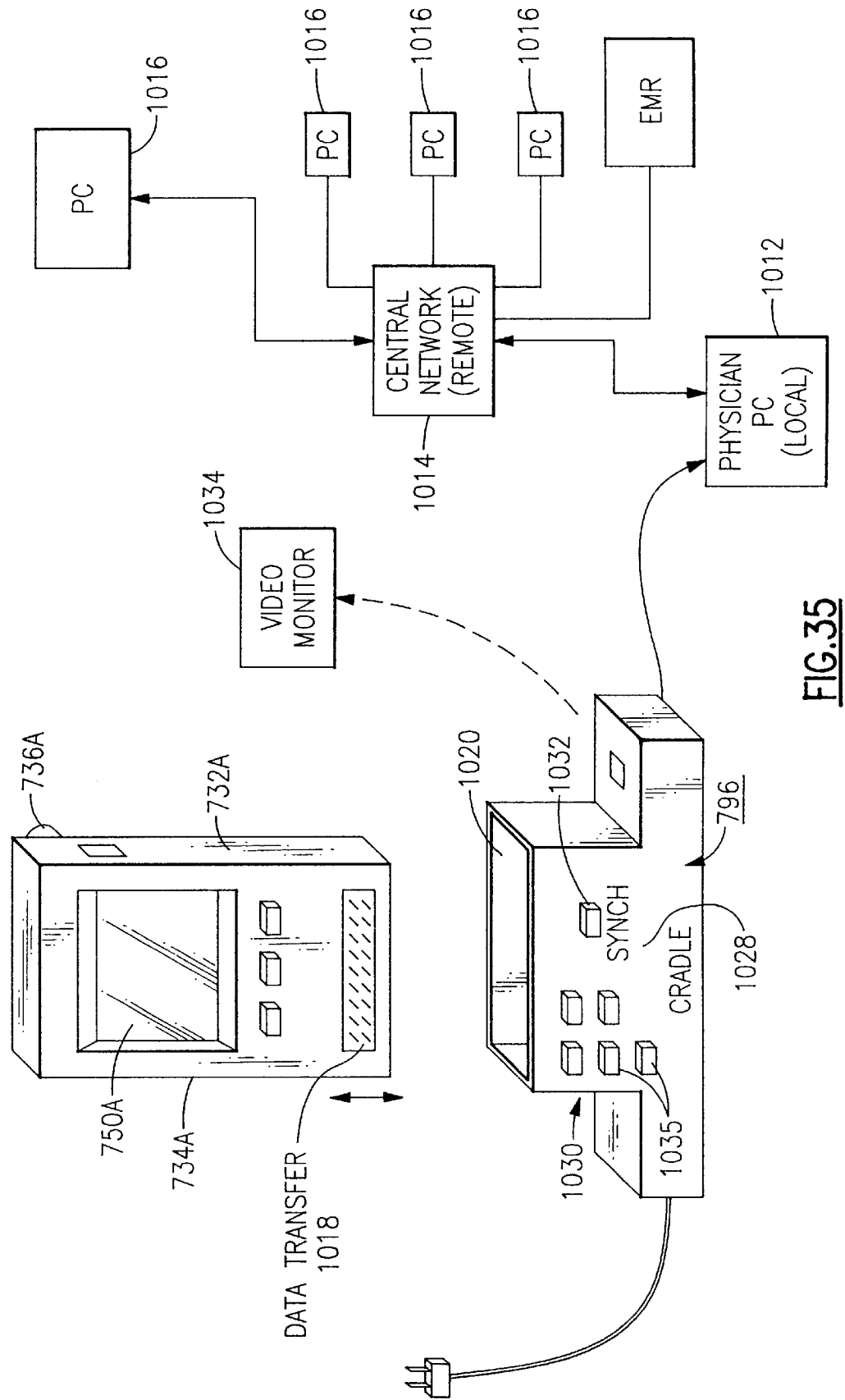
FIG. 35 is a systematic diagram of the instrument of FIG. 14 in connection with a receiving cradle capable of transferring data between the diagnostic instrument and a central data network.

A number of the above problems are minimized by the record management system, having the major features which are illustrated in FIG. 35. For purposes of the discussion, similar features will be described using the same reference numerals. In brief, a diagnostic instrument 732A, similar to the instrument 732 described above, with a different body 734A is used in conjunction with a cradle 796 which provides a data transfer function to allow downloading of stored audio and video data from the internal memory of the instrument 732A. The cradle 796 is interconnected to a local computer station 1012 which incorporates the downloaded data into a local database. In the described embodiment, audio (WAV) files are arranged with corresponding video data in a template which forms the basis for a patient record data sheet, the files being separated by identifiers (for example, patient and doctor names) as described in greater detail below.

The audio data files are transmitted to a central network server 1014 which includes a number of computer stations 1016 which utilize human transcriptionists and voice recognition software, as described below, to create a transcription record which is downloaded back to the local computer in the generated template format. Reports can then be generated which can be stored in the local database, and can be printed for creating, maintaining and updating of patient files.

As noted, the diagnostic instrument 732A includes those features as the instrument 732A described above. That is, the instrument 732A is a compact digital camera which has been configured for use with a plurality of selectively interchangeable instrument heads. Each of the instrument heads includes a specific optical system which allows an optical image of interest to be focused onto an electronic imaging element. The instrument 732A includes an instrument housing 734A having an integral display 754, and support electronics (not shown) for converting the optical signal into a video signal which is captured and displayed. A microprocessor within the instrument 732A contains programmable logic which allows a real-time image to be continuously displayed and also allows a predetermined number of images to be captured and stored into memory, selectively or otherwise, along with corresponding audio and/or annotation data added using an integral microphone and the display, which is preferably touch-sensitive and includes a number of controls on the instrument housing 734A and keys located on the TFT display 754, as previously described. In another embodiment, the instrument can selectively utilize data, such as to combine audio and annotative data, without reliance on video data for those applications which do not necessarily require this form of input.

Still referring to FIG. 35, and according to this specific embodiment, the instrument 732A includes a pinned data exchange (SCSI) connector 1018 configured for engagement with a corresponding port (not shown) located in the receiving cavity 1020 of the cradle 796. As should be apparent, the form of data transfer is not critical, for example, the data exchange connector can also be USB or serial. The cradle 796 is linked by conventional means to a local personal computer (PC) 1012 located in the physician's office, while the physician's computer is, according to this embodiment, connected either through phone lines through dial-up networking, a LAN connection, or alternately via the Internet to a central computer network 1014 to which other individual remote PC stations 1016 are also connected.

As shown in FIG. 35, the cradle 796 includes a supporting base portion 1028 having the receiving cavity 1020 appropriately sized for retaining the diagnostic instrument 732A, shown partially. Preferably, the base portion 1028 can also include a separate storage cavity (not shown) or other means for retaining any of the loose interchangeable instrument heads.

A control section 1030 of the cradle 796 includes a number of controls including an actuatable synch button or switch 1032, which when activated automatically downloads the stored digital video, audio and annotation (if any) data contained within the internal memory of the supported diagnostic instrument 732A into the local PC 1012.

The control section 1030 further includes a plurality of indicator lamps 1035 which indicate specific operational features of the cradle 796, such as to indicate the extent of charging of the instrument batteries, the status of data transfer, and overall powering of the station. For purposes of the present discussion, and upon proper attachment, activation of the synch button 1032 causes all audio, annotated and video data to be automatically downloaded to the local PC 1012.

The cradle 796 according to the present embodiment is capable of performing additional functions. For example, means are provided for recharging the batteries contained in the compartment 794, FIG. 17, of the instrument 732A while nested. Additionally, the instrument 732A can also be powered (for example, when battery power is low) while attached to the cradle 796, through interconnection to a wall outlet or other source of electrical power. The control section 1030 can also be configured with additional switches (not shown) which interconnect with the controller through the data transfer connector of the instrument 732A to allow the instrument to be operated directly from the cradle 796. An advantage realized by this from of control is that the instrument 732A can be made capable of receiving data from other instruments, such as a clinical vital signs monitor, for storage as part of a patient protocol.

Still referring to FIG. 35, the cradle 796 also preferably allows connection to a separate video monitor 1034 or other peripheral device for viewing of the captured images, such as with other doctors, patients or interested parties. Alternately, the instrument 732A, such as the above described Nikon COOLPIX E300 digital camera, also allows direct connection to a video monitor without requiring direct use of a cradle 796, if desired. Corresponding audio and annotation data can be similarly transferred with the video data in a manner known in the field. Techniques for transferring of this data is already known in the art and does not form a part of the present invention, therefore no further discussion is required.

Figure 37:
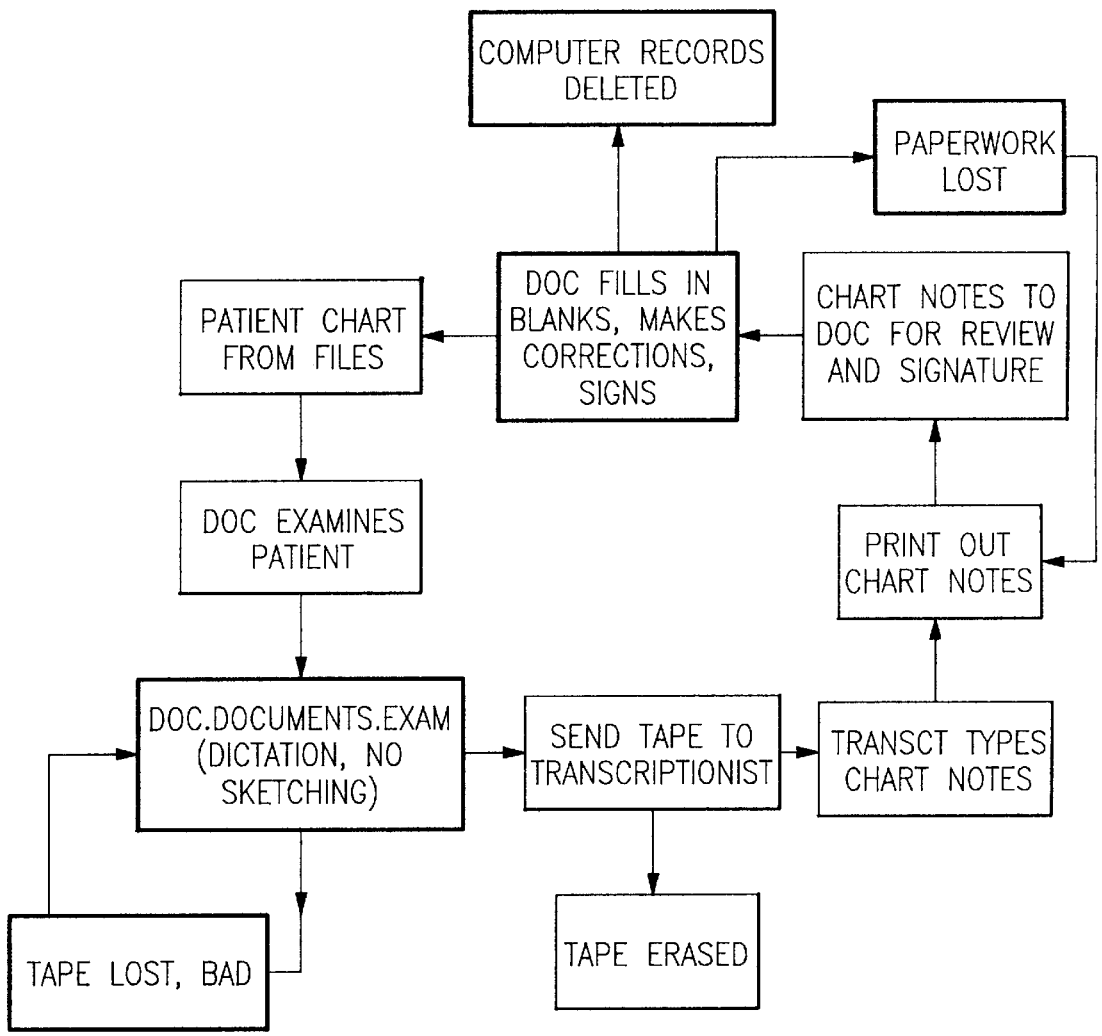
FIG. 37 is a flow chart representative of the prior art for transcription methodology relating to audio medical records.
Figure 40:
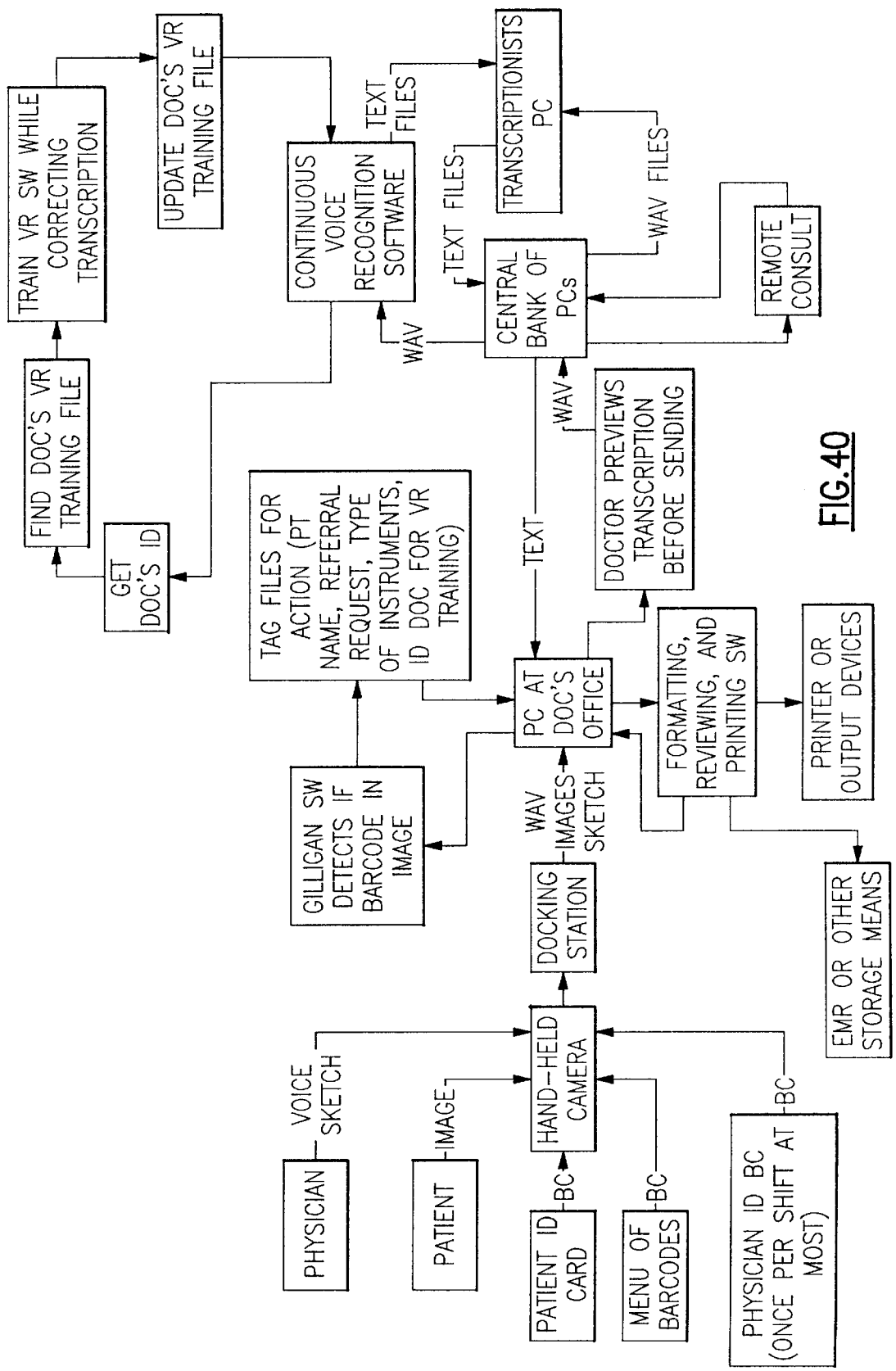
FIG. 40 is a flow chart illustrating the flow of image and audio data in connection with the data management system of FIG. 38.
Figures 41, 41A:
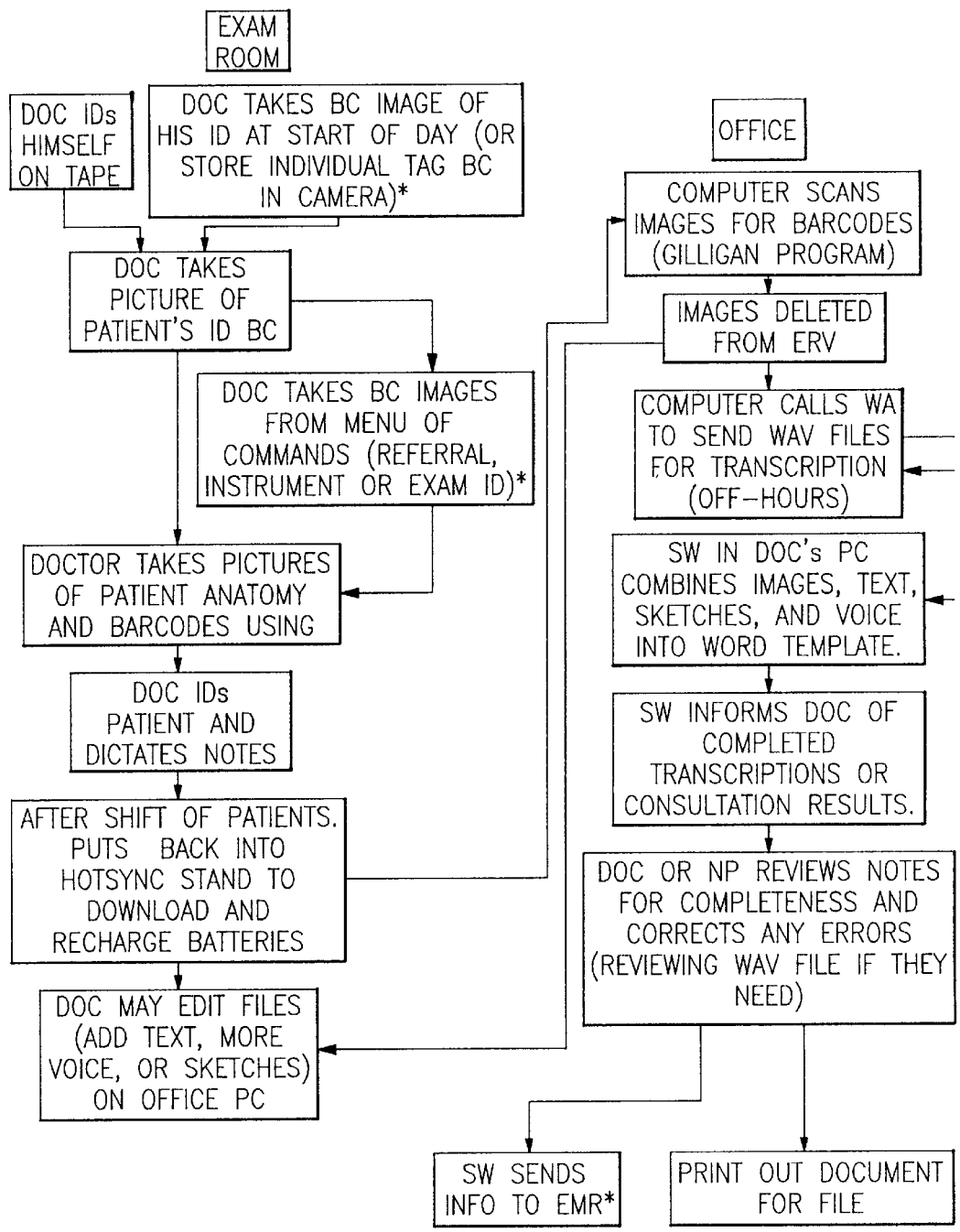
FIG. 41 is a detailed flow chart of the transcription process using the data management system of FIG. 38.
Figure 41B:
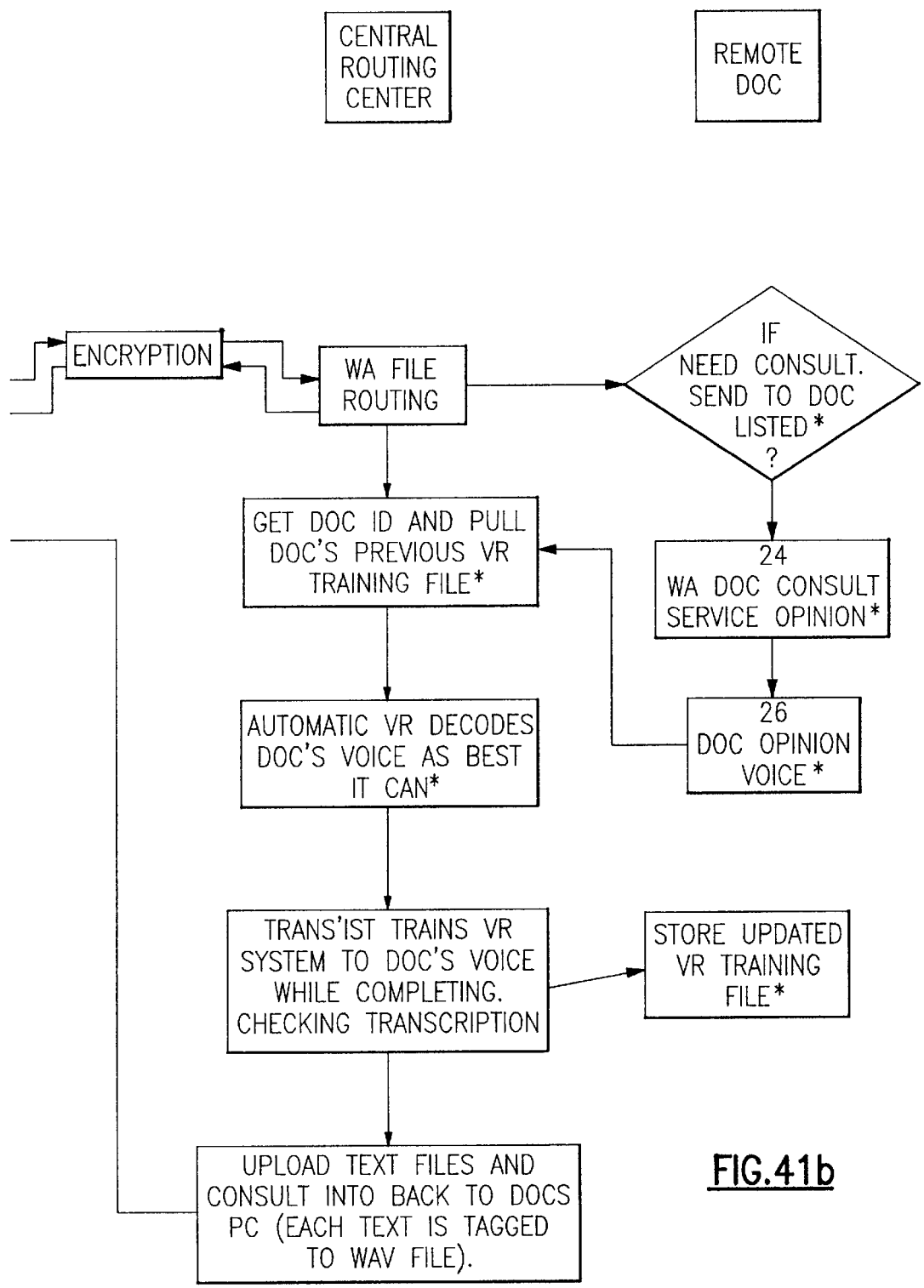

Referring to the flowcharts of FIGS. 37 and 40–41, the preferred record management system is herein described. The description relates specifically to an office visit by a patient, though it will be readily apparent that the above could also apply to a typical round or hospital shift or other suitable setting in which a single patient or plurality of patients are to be examined.

First, the patient chart is pulled from the files for the physician. The physician then initiates the examination by utilizing the diagnostic instrument 732A by removing the instrument from the cradle 796 and attaching the general purpose instrument head 738 to the front interface 46 of the instrument in the manner described previously. Preferably, the cradle 796 recharges the batteries of the instrument 732A sufficiently to allow several hours of typical use.

Depending on the particular protocol of the local database (that is, the template of the patient data folder created by the database), a patient ID and doctor ID are first captured. One way of obtaining either ID is by capturing and storing video image(s) of the printed patient chart. The ID may or may not include barcode information. Alternately, a video image of the patient can be taken and the appropriate data can be added via annotation, using the TFT display 754. Alternately, doctor and patient information can be captured via a menu in the controller software. As in the preceding, images are captured and stored by first activating the instrument 732A using switch 768, FIG. 18, and framing the image to be captured into memory in the integral display 754. Actuation of the shutter control button (not shown) of the instrument 732A allows each digital image of interest to be stored into the internal memory of the contained controller. Vital sign and other pertinent patient data would also be added, either as a captured video image or be entering the data directly into the internal memory of the instrument. Data from other instruments or from other measurements can be entered into the instrument 732A by a number of known methods. For example, data could be sent using RF or other wireless technologies. Data could also be entered using the keyboard of the local PC 1012, through buttons, or other known input devices on the instrument itself.

The physician is then ready to begin examinations, such as done on a daily basis in the office, for example. As described above, each patient visit is initialized by capturing a video image of the patient ID and storing the image into the internal memory of the microprocessor. Additional patient data can then be captured using the instrument and selectively any of the interchangeable instrument heads which may be required. The physician can also capture audio data pertaining to each captured video image of interest using the microphone 764, FIG. 18, through activation of the switch 770, FIG. 18, the video and audio data being available for playback using speaker 766, FIG. 18, also using switch 770, FIG. 18, at any point during the examination. The instrument according to the present embodiment utilizes an internal calendar with date stamping to identify the date and time of each captured image. Alternately, this data could be entered separately or other data could be entered, such as from an external source, including operating instructions, protocol, height and weight data, as well as other pertinent information which can be added using the local computer or the network, for example. Each new patient requires identification of the new patient ID, as described above. During the exam, after the exam, after examining several patients, or at the end of the day, the physician can perform his dictation in the usual manner. At the end of the day, or after a determinate number of examinations, the instrument 732A is loaded into the receiving cavity 1020 of the cradle 796. The software contained within the instrument 732A further preferably allows additional data entry for an earlier patient, if desired, such as to include later obtained data from another external source, etc.

Upon loading the diagnostic instrument 732A into the receiving cavity 1020 of the cradle 796, the synch button 1032 is actuated, automatically transferring the stored audio (WAV), video, and annotation data files (if any) to the physician's local PC 1012. The software provided in the local PC loads the raw data into a specific template, an example of which is shown in FIG. 43. Preferably, a confirmation indication is provided on the display of the local PC 1012 to indicate that all images and audio clips have been removed from the instrument 732A.

During the data transfer to the local database, the doctor and patient IDs are first located and identified. In the case of use of bar codes, the local PC 1012 preferably includes recognition software which allows identification of the doctor and patient IDs and loads the data into an already existing or newly created patient file. Most preferably, the software includes pattern recognition or bar code recognition programs which can detect the existence of a barcode or other pattern from an existing and captured video image and then decode the bar code or pattern if such information is present. In the present embodiment, the doctor ID or the patient ID may contain a 1D or 2D bar code pattern, the determination of which engages the following transcription routine. Details relating to the software for detecting barcode from a digitally captured video image is described in greater detail in U.S. application Ser. No. 60/030,360 [Attorney Docket 283-213, filed Nov. 5, 1996], the entire contents of which is herein incorporated by reference. The barcode recognition software can also be used to control the instrument 732A. For example, the software can be used to indicate the type of instrument head being used or which anatomy type a physician is examining or imaging.

Upon identifying the doctor and patient, the software creates a new data folder in the event of a previously unlisted patient, or accesses an already existing patient folder by comparison to a list stored in memory. Preferably, a security feature is loaded into the logic of the local computer 1012 prompting a user identification window and requiring a password be entered prior to allowing access to the raw data for review or prior to transferring the data to the central data network 1014. The software automatically stores images and other associated data input to a tagged file having the ID number or name attributed to it. As such, the files can be automatically stored without requiring human intervention or assistance. In addition, the files can also be tagged for action, such as additional tests, follow-up visits, inoculations, prescriptions, or other procedures.

After all of the stored data (video, audio, etc.) has been downloaded onto the local database and reviewed, an election is made to send all or part of the data, in this embodiment the digital audio files (WAV) files, such as through phone lines as part of a LAN connection , by dial-up networking, e-mail transfer or alternately over the Internet by known means to the central data network 1014. Prior to transmitting this data, the WAV files are first previewed, such as by the physician at the local PC 1012, if desired by selection of the appropriate entry queued at the patient template. Alternately, other image data can be archived to the central network location 1014 while the audio data is being transmitted.

Preferably, the local PC 1012 encrypts the data prior to transferring the data to the central data network 1014, where the data will be decrypted using techniques known in the field. The details of encryption/decryption do not form an essential part of the present invention and therefore require no further discussion. The data is transferred between the local PC 1012 and the central data network 1014 using the template originally created at the local PC. Because the data is transferred in this format, it is not necessary to sent the corresponding video data to the central data network 1014. However, image files may be transferred for data storage (warehousing) or for sending referring letters via e-mail or other purposes.

At the central data network 1014, the audio digital (WAV) files can be transcribed after being loaded into a server or other hardware, the center having a plurality of linked computer stations 1016 using human transcriptionists in combination with an automatic voice recognition (hereinafter referred to as VR) software system, such as Dragon Systems Naturally Speaking to develop a database of a doctor's vocabulary. Preferably, the VR software contains an adaptation or learning mode which improves the general efficiency of transcription as related to specific physician(s). That is, as the number of transcriptions using the dedicated physician necessarily improves more efficiently over time by updating of a specific dedicated physician file. However, unlike traditional uses of voice recognition software, the training would be done by transcriptionists rather than the physicians themselves.

According to the flowchart of FIGS. 40 and 41, and upon receipt of the raw audio data from the local PC 1012, the physician's ID is retrieved from memory at the central database and the training file (if existing) is accessed. Otherwise, a new doctor's training file is created. An original version of the transcription is then automatically created, the results of which are then subsequently transmitted, also automatically, to a separate PC station 1016 for review by a human transcriptionist.

Using the WAV files obtained from memory by accessing the training folder, the transcriptionist can effect any changes which may be required based on a review of the created transcription, the changes being directly inputted into the record and also into the VR software into the training file. The above procedure can then be iterated until the training using the VR software has progressed to a given level and a suitable transcription is produced. The number of iterations (edits) will significantly decrease with an increasing number of transcription files, based on the learning mode, and assuming the physician performs an initial vocabulary building exercise typically required of presently known VR software. This improvement creates an increase in efficiency and accuracy after an initial learning curve for each physician. At the PC station 1016, the transcriptionist can also access the video and annotation files, if transmitted and as needed, to further improve the reviewing process. The chief benefit of this sort of training method is that the difficult job of training VR software is done by lower paid personnel which is more efficient, thereby freeing the physicians to perform the jobs they were trained for.

Following the transcription procedure at the central network center, a copy of the transcription is removed from the training file and is attached to the specific patient data file in the appropriate location prompted by the incoming template. The data file is then transferred to the local PC 1012 in the template format having the transcribed information added as shown in FIG. 43 in the vicinity of the corresponding video image. Data transfer is performed either through a LAN connection, dial-up networking, or other suitable means either through telephone lines or via the Internet (http/ftp) . At the local PC 1012, the transcription can then be reviewed by the physician where the information can be reviewed for accuracy and additional editing, if needed. At the physician's local PC 1012, the physician can also access the image and audio portions of the patient chart while reviewing the transcription. A finalized copy can be approved or signed off by the physician prior to adding a hardcopy of the file to the patient record.

The appropriate files are originally combined using a data file accumulated prior to transcription which is presented using a script template. The template can be reviewed and the audio information can be accessed by cursor, mouse or keyboard control to icons presented adjacent to the video images. The icons access the audio files with the annotation files being presented along with the video files. After the transcription has been completed, a hardcopy with the transcription record added appropriately with the images in place of the icons can be printed for placing in the patient file.

The video images, once received into the system are scanned. Subsequent changes, such as cropping or airbrushing, etc may be detected to prevent distortion or falsification of records. Further, the system preferably contains appropriate encryption programs for preventing access to the records by unauthorized persons.

The data can also be transmitted over the telephone lines in any known manner or via the Internet to an EMR or other remote site, with the central network station 1014 also allowing receipt of information therefrom from other sources, etc. to aid in networking. For example, information from an instrument at a remote site relative to the local PC 1012 can be transmitted into the local database or be unlinked by known means through the cradle 796 to the instrument 732A.

Though the preceding data management system described in detail, a technique of remotely transcribing using a central bank of computers, it should be realized that the transcription could certainly be done locally. That is to say, the immediate benefit is the ability of the instrument of the present invention to incorporate multiple forms of data which can be linked, including audio, video, annotation, etc., to allow data management to be better coordinated. The features, though pertaining to the medical profession in the preceding embodiment, are clearly applicable to other service providers, including attorneys, insurance agents, and the like, as well as a myriad of other suitable applications.

We claim:

1. A compact imaging instrument capable of performing multiple examination tasks, said instrument comprising:
   a hand-gripable housing including an interior;
   a plurality of instrument heads, at least one of said instrument heads having a contained illumination assembly;
   mounting means for interchangeably and releasably mounting each of said plurality of instrument heads to said housing;
   an electronic image sensor disposed in one of said housing and said plurality of instrument heads;
   at least one optical element disposed in the interior of at least one of said housing and said plurality of instrument heads, said at least one optical element being aligned to focus an optical image onto said electronic image sensor along a defined optical axis; and
   transmission means including at least one first electrical contact disposed in said housing and connected to a contained power source, each of said instrument heads including at least one second electrical contact for engaging said at least one first electrical contact when an instrument head is attached to said housing.

2. An imaging instrument as recited in claim 1, in which said mounting means includes a latching member provided on one of said plurality of instrument heads and said housing and engagement means provided on the other of said housing and said plurality of instrument heads for receiving said latching member.

3. An imaging instrument as recited in claim 2, wherein said housing includes at least one facing surface, said latching member depending from one end of each of said plurality of instrument heads and said engagement means disposed on said at least one facing surface.

4. An imaging instrument as recited in claim 3, wherein said latching member is rotatably mounted to said engagement means between an open unlocked position and a closed locked position.

5. An imaging instrument as recited in claim 4, wherein said latching member includes a pair of diametrically opposed ear portions, said engagement means including a cavity sized for receiving said latching member and having radially disposed slots for engaging said ear portions.

6. An imaging instrument as recited in claim 5, wherein said radially disposed slots each include a stop defining the closed locked position for an attached instrument head.

7. An imaging instrument as recited in claim 6, wherein said transmission means engages said electrical contacts only after said latching member has been rotated to said locked position.

8. An imaging instrument as recited in claim 1, wherein said illumination assembly includes at least one light source having said at least one second electrical contact extending therefrom.

9. An imaging instrument as recited in claim 8, wherein said at least one second electrical contact of said illumination assembly contacts said at least one first electrical contact of said transmission means when an instrument head having said illumination assembly is attached thereto.

10. An imaging instrument as recited in claim 8, including means for adjusting the position of said illumination assembly relative to said viewing axis and said optical viewing means.

11. An imaging instrument as recited in claim 1, wherein at least one of said plurality of instrument heads includes said electronic image sensor, said transmission means including electrical contact members in each of said at least one of said plurality of instrument heads and said housing for enabling said image sensor when an instrument head having said electronic image sensor is attached to said housing.

12. An imaging instrument as recited in claim 1, wherein said power source includes at least one battery disposed in said housing.

13. An imaging instrument as recited in claim 12, wherein said at least one battery is rechargeable.

14. An imaging instrument as recited in claim 13, including means for recharging said at least one battery without removal from said instrument body.

15. An imaging instrument as recited in claim 12, wherein said at least one battery is removable from said housing.

16. An imaging instrument as recited in claim 1, including image transmission means for transmitting an image signal from said electronic image sensor to a video peripheral device.

17. An imaging instrument as recited in claim 16, wherein said image transmission means includes an RF circuit board and antenna attached to said electronic image sensor for wireless transmission of said image signals to a video peripheral device.

18. An imaging instrument as recited in claim 16, wherein said video peripheral device is a video processor.

19. An imaging instrument as recited in claim 16, wherein said video peripheral device is a video processor.

20. An imaging instrument as recited in claim 16, wherein said video peripheral device is a monitor.

21. An imaging instrument as recited in claim 1, wherein at least one of said instrument heads is an otoscopic instrument head.

22. An imaging instrument as recited in claim 21, wherein said otoscopic instrument head includes an illumination assembly and an insufflation port.

23. An imaging instrument as recited in claim 1, wherein at least one of said instrument heads is a surface microscope head.

24. An imaging instrument as recited in claim 23, wherein said surface microscope head includes a housing having a distal surface contacting window and an illumination assembly disposed adjacent said window, said illumination assembly further including at least one light source and anti-glare means for transmitting light from said at least one light source to said window without substantial glare.

25. An imaging instrument as recited in claim 24, including a cylindrical light pipe extending from said illumination assembly to said distal window.

26. An imaging instrument as recited in claim 24, wherein said anti-glare means includes at least one polarizer element disposed in proximity to one of said optical viewing means and said at least one light source.

27. An imaging instrument as recited in claim 1, including an adjustable lens cell disposed within at least one of said instrument heads along said optical axis and aligned with said electronic image sensor, said lens cell being axially adjustable for focusing an optical image onto said sensor.

28. An imaging instrument as recited in claim 1, wherein said housing comprises a hand-held digital camera having an integral display for displaying at least one image from said electronic image sensor.

29. An imaging instrument as recited in claim 28, including a controller disposed in said housing and having memory means capable of storing image data obtained from said electronic image sensor.

30. An imaging instrument as recited in claim 29, including data capture means for capturing data other than imaging data from said electronic image sensor.

31. An imaging instrument as recited in claim 30, wherein said data capture means includes audio recording means for recording audio data.

32. An imaging instrument as recited in claim 31, including audio playback means for playing back audio data stored by said data capture means.

33. An imaging instrument as recited in claim 30, wherein said memory means can store data captured by said data capture means and said electronic image sensor.

34. An imaging instrument as recited in claim 33, wherein said memory means is removable from said housing.

35. An imaging instrument as recited in claim 30, including means for editing data stored in said memory means.

36. An imaging instrument as recited in claim 33, including control means for transferring stored data between at least one external device and said memory means.

37. An imaging instrument as recited in claim 36, including a medical instrument provided as an external device which is connectable to said housing and said control means to permit transfer of data therebetween.

38. An imaging instrument as recited in claim 36, including a computer provided as an external device which is connectable to said housing and said control means for allowing transfer of data therebetween.

39. An imaging instrument as recited in claim 38, wherein said control means includes for receiving operating instructions from said computer.

40. An imaging instrument as recited in claim 36, wherein said control means includes a receiving cradle having means for retaining said housing, said cradle including data transfer means for transferring stored data from said memory means to at least one external device.

41. An imaging instrument as recited in claim 40, wherein said instrument includes at least one rechargeable battery, said cradle having means for selectively recharging said at least one rechargeable battery when said instrument is attached thereto.

42. An imaging instrument as recited in claim 36, wherein said control means includes means for allowing two or more images stored in said memory means to be displayed simultaneously.

43. An imaging instrument as recited in claim 40, wherein said cradle includes means for separately powering said instrument.

44. An imaging instrument as recited in claim 36, wherein said at least one external device includes means for selectively separating identified data stored in said memory means of said instrument.

45. An imaging instrument as recited in claim 33, wherein said memory means includes means for storing captured data into identifiable folders.

46. An imaging instrument as recited in claim 30, wherein said data capture means includes means for annotating notes relating to at least one displayed image.

47. An imaging instrument as recited in claim 46, wherein said integral display means is touch-sensitive, allowing annotation data to directly added thereon.

48. An imaging instrument as recited in claim 29, including means for identifying and decoding patterns from a video image stored in said memory means.

49. An imaging instrument as recited in claim 48, wherein said patterns include 1D and 2D bar-code symbols contained in an image captured by said electronic image sensor.

50. An imaging instrument as recited in claim 28, wherein said display includes a number of image fields, said instrument including means for selectively displaying a plurality of stored images in said image fields.

51. An imaging instrument as recited in claim 1, including means for interconnecting said housing with a video remote peripheral device.

52. An imaging instrument as recited in claim 1, wherein at least one of said plurality of instrument heads is a general viewing instrument head.

53. An imaging instrument as recited in claim 52, in which said general viewing instrument head includes focusing optics for varying the focus distance.

54. An imaging instrument as recited in claim 1, wherein at least one of said plurality of instrument heads is a magnifying instrument head having optical viewing means for focusing a magnified image onto said electronic image sensor.

55. A compact imaging instrument capable of performing multiple types of examination, said instrument comprising:
  an instrument housing comprising a photographic digital camera; and
  a plurality of instrument heads interchangeably attachable to the exterior of said housing, each of said instrument heads having a different optical system having at least one optical element for directing a substantially focused optical image onto an electronic image sensor said electronic image sensor being disposed in one of said instrument housing and said plurality of instrument head.

56. An imaging instrument as recited in claim 55, wherein said plurality of instrument heads includes at least one of a general viewing head, an otoscopic head, a surface microscopic head, and a magnifying head.

57. An imaging instrument as recited in claim 55, wherein said electronic image sensor is disposed in said photographic digital camera.

58. An imaging instrument as recited in claim 57, wherein said photographic digital camera includes a display integral with said housing for displaying at least one image captured by said electronic image sensor, and multi-media data capture means for capturing data other than image data.

59. An imaging instrument as recited in claim 58, wherein said photographic digital camera further includes a controller having memory means for digitally storing image data as well as data captured by said data capture means.

60. An imaging instrument as recited in claim 59, wherein said controller includes means for identifying data captured by said image sensor and said multi-media data capture means and for storing the identified data into specified portions of memory as a folder file.

61. An imaging instrument as recited in claim 58, wherein said display is a touch-sensitive LCD, having means for annotating onto at least one displayed image.

62. A compact medical diagnostic instrument comprising:
  a modified hand-held photographic digital camera having a compact housing;
  at least one diagnostic instrument head releasably attachable to the exterior of said housing of said camera, which has been retrofitted to allow selective attachment of said at least one instrument head, said at least one instrument head containing an optical system;
  an electronic image sensor disposed within one of said camera housing and said at least one instrument head for capturing at least one image of interest which has been directed to said electronic image sensor by said optical system;
  a display integral with said camera housing for displaying at least one image captured by said electronic image sensor;
  multi-media data storage means within said hand-held digital camera for storing multiple forms of data other than image data selectively with said captured image data and
  transmitting means including at least one first electrical contact disposed in said instrument housing connected to a contained power source, said at least one instrument head including at least one second electrical contact for engaging said first electrical contact when said at least one instrument head selectively attached in locking engagement to the exterior of said housing.

63. An imaging instrument as recited in claim 62, wherein said multiple forms of data include at least one of annotation and audio data.

64. An imaging instrument as recited in claim 62, including a plurality of instrument heads selectively and interchangeably attachable to said modified hand-held digital camera housing, each of said instrument heads having an optical viewing system capable of effectively viewing a different target of interest and for directing an image of said target to said electronic image sensor.

65. A record management system comprising:
  a hand-held digital camera defined by a single unitary camera housing which has been modified to selectively accommodate one of a plurality of interchangeable instrument heads attachable to an exterior side of said camera housing, each of said instrument heads having an optical system for directing an image onto an electronic image sensor disposed in one of said camera housing and said plurality of interchangeable instrument heads, said hand-held digital camera having multi-media data capture and data storage means for electronically capturing and storing video data captured by said electronic image sensor and at least one other form of data either separately or in conjunction with captured video data and an integral display for displaying captured video data; and
  means for transferring stored data between said camera and at least one remote processing device, said at least one remote processing device including means for automatically converting audio data stored in said modified camera into textual data, and for organizing transferred data, including converted audio data, into a record format.

66. A record management system comprising:

a medical diagnostic instrument including a modified hand-held photographic digital camera and a plurality of interchangeable instrument heads, each of said instrument heads being releasably attachable to a(retrofitted exterior of said modified photographic digital camera and having an optical system for directing an image onto an electronic image sensor disposed in one of said digital camera and said instrument heads, said instrument heads being one of an otoscopic instrument head, a skin surface microscope head, a magnifying instrument head and a general viewing instrument head, said instrument further including an integral display for displaying at least one directed image, and data capture and storage means disposed in said housing for digitally capturing and storing audio and video data; and means for transferring digitally stored data between said diagnostic instrument to at least one processor, said at least one processor including means for converting audio data stored by said camera into text data, and for organizing data transferred from said instrument including said converted text data into a record format.

67. A compact imaging instrument capable of performing multiple examination tasks comprising:

a modified hand-held grippable photographic digital camera having contained data capturing means for capturing video data and at least one other form of data including audio data and data storage means for digitally storing captured video and audio data within a modified hand-held camera body; and a plurality of instrument heads, each of said instrument heads having a contained optical system; and in which each of said instrument heads and said modified camera body include:

mounting means for interchangeably and releasably mounting each of said plurality of instrument heads to said modified camera body so as to align the optical system of each said instrument head to the data capturing means of said camera when an instrument head is selectively attached to the modified hand-held photogaphic digital camera.

68. An instrument as recited in claim 67, wherein at least one of said instrument heads includes an illumination system alignable with said data capturing means, said mounting means including means for electrically interconnecting said illumination system with a power supply contained within said camera body when said at least one instrument head is attached thereto.

69. An instrument as recited in claim 68, wherein said electrical interconnection means includes means for activating the illumination system of a mounted instrument head only if said head is moved into a locking position relative to said camera body.

70. An instrument as recited in claim 67, wherein said digital camera includes an integral display for displaying image data captured by said data capture means.

71. An instrument as recited in claim 67, wherein said plurality of instrument heads includes at least one of an otoscopic, general viewing, magnification and skin surface microscope instrument head.

72. An instrument as recited in claim 67, wherein said data storage means includes means for creating patient data folders for storing data captured by said data capturing means in conjunction with said plurality of instrument heads.

73. An imaging instrument as recited in claim 67, including an illumination system disposed in one of said photographic digital camera and said plurality of instrument heads, said illumination system having a light source and means for optically transmitting light from said light source to a target being viewed.

* * * * *

UNITED STATES PATENT AND TRADEMARK OFFICE
CERTIFICATE OF CORRECTION

PATENT NO. : 6,106,457
DATED : August 22, 2000
INVENTOR(S) : Perkins et al.

It is certified that error appears in the above-identified patent and that said Letters Patent is hereby corrected as shown below:

Column 36,
Line 31, please delete [hand-gripable] and insert -- hand-grippable --.

Column 40,
Line 29, after the word data please insert -- ; --.

Column 41,
Lines 31 and 32, after the word capturing please delete [video data and at lease one other form of data including audio data and data storage] and insert -- at least one of audio and video data and data storage --.

Signed and Sealed this

Fourteenth Day of August, 2001

*Attest:*

*Attesting Officer*

NICHOLAS P. GODICI
*Acting Director of the United States Patent and Trademark Office*